United States Patent [19]
Jaehne et al.

[11] Patent Number: 6,159,996
[45] Date of Patent: Dec. 12, 2000

[54] POLYCYCLIC THIAZOLIDIN-2-YLIDENE AMINES, PROCESS FOR THEIR PREPARATION, AND THEIR USE AS PHARMACEUTICALS

[75] Inventors: Gerhard Jaehne; Karl Geisen, both of Frankfurt; Hans Jochen Lang, Hofheim, all of Germany

[73] Assignee: Aventis Pharma Deutschland GmbH, Frankfurt am Main, Germany

[21] Appl. No.: 09/351,621

[22] Filed: Jul. 12, 1999

[30] Foreign Application Priority Data

Jul. 17, 1998 [DE] Germany ............... 198 31 878

[51] Int. Cl.$^7$ ............... A61K 31/425; A61K 31/505; A61K 31/385; C07D 243/00; C07D 239/00
[52] U.S. Cl. ............... 514/366; 514/257; 514/439; 514/211.1; 540/555; 544/247; 548/150; 548/149
[58] Field of Search ............... 548/150, 149; 514/366, 257, 211.1, 439; 544/247; 540/555

[56] References Cited

U.S. PATENT DOCUMENTS 3,507,868   4/1970   Manning ............... 260/251
4,174,397  11/1979   Knabe et al. ............... 424/270

FOREIGN PATENT DOCUMENTS 26 40 358   3/1978   Germany .

*Primary Examiner*—John Kight
*Assistant Examiner*—Binta Robinson
*Attorney, Agent, or Firm*—Foley & Lardner

[57] ABSTRACT

Polycyclic thiazolidin-2-ylidene amines and their physiologically tolerable salts and physiologically functional derivatives of the formula I

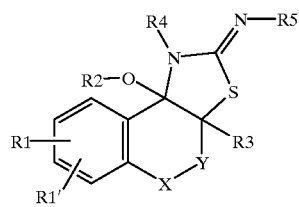

in which the radicals have the meanings indicated, and their physiologically tolerable salts and a process for their preparation are described. The compounds are suitable, for example, as anorectics.

15 Claims, No Drawings

POLYCYCLIC THIAZOLIDIN-2-YLIDENE AMINES, PROCESS FOR THEIR PREPARATION, AND THEIR USE AS PHARMACEUTICALS

BACKGROUND OF THE INVENTION

1. Field of the Invention

The invention relates to polycyclic thiazolidin-2-ylidene amines, and their physiologically tolerable salts, and physiologically functional derivatives, processes for their manufacture and process for their use.

2. Description of the Related Art

Thiazolidine derivatives having anorectic action have already been described in the prior art (Austrian Patent No. 365181).

SUMMARY OF THE INVENTION

The invention was based on the object of making further compounds available which display a therapeutically utilizable anorectic action. In this connection, the object was in particular also to find compounds in which the anorectic action is increased compared with the compounds from AT 365181.

The invention therefore relates to polycyclic thiazolidin-2-ylidene amines of the formula I in which
A)
Y is a direct bond, —$CH_2$—, or —$CH_2$—$CH_2$—;
X is $CH_2$, $CH(CH_3)$, $CH(C_2H_5)$, or $CH(C_3H_7)$;
R1 is CN, COOH, COO($C_1$–$C_6$)-alkyl, $CONH_2$, CONH ($C_1$–$C_6$)-alkyl, CON[($C_1$–$C_6$)-alkyl]$_2$, ($C_2$–$C_6$)-alkyl, ($C_2$–$C_6$)-alkenyl, ($C_2$–$C_6$)-alkynyl; O—$CH_2$—$CF_3$, O—$CH_2$—$CF_2$—$CF_3$, or O—($C_4$–$C_6$)-alkyl, where in the alkyl radicals one or more, or all hydrogen(s) can be replaced by fluorine, or one hydrogen can be replaced by OH, OC(O)$CH_3$, O—$CH_2$—Ph, $NH_2$ or N(COOCH$_2$Ph)$_2$;
S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, or $SO_2$—($CH_2$)$_n$-phenyl, where n can be =0–6 and the phenyl radical can be substituted up to two times by F, Cl, Br, OH, $CF_3$, $NO_2$, CN, $OCF_3$, O—($C_1$–$C_6$)-alkyl, ($C_1$–$C_6$)-alkyl, $NH_2$; $NH_2$, NH—($C_1$–$C_6$)-alkyl, N(($C_1$–$C_6$)-alkyl)$_2$, NH($C_1$–$C_7$)-acyl, phenyl, biphenyl, O—($CH_2$)$_n$-phenyl, where n can be =0 –6, 1- or 2-naphthyl, 2-, 3- or 4-pyridyl, 2- or 3-furanyl or 2- or 3-thienyl, where the phenyl, biphenyl, naphthyl, pyridyl, furanyl or thienyl rings in each case can be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$-$CH_3$, COOH, COO—($C_1$–$C_6$)-alkyl, $CONH_2$;
1,2,3-triazol-5-yl, where the triazole ring can be substituted in the 1-, 2- or 3-position by methyl or benzyl;
tetrazol-5-yl, where the tetrazole ring can be substituted in the 1- or 2-position by methyl or benzyl;

R1' is H, F, Cl, Br, I, $CH_3$, $CF_3$, O—($C_1$–$C_3$)-alkyl, $NO_2$, $SO_2$—$NH_2$, $SO_2NH(C_1$–$C_6)$-alkyl, $SO_2N[(C_1$–$C_6)$-alkyl]$_2$ or R1;
R2 is H, ($C_1$–$C_6$)-alkyl, ($C_3$–$C_6$)-cycloalkyl, ($CH_2$)$_n$-phenyl, ($CH_2$)$_n$thienyl, ($CH_2$)$_n$-pyridyl, ($CH_2$)$_n$-furyl, C(O)—($CH_2$)$_n$-phenyl, C(O)—($CH_2$)$_n$-thienyl, C(O)—($CH_2$)$_n$-pyridyl, C(O)—($CH_2$)$_n$-furyl, where n can be =0–5 and in which phenyl, thienyl, pyridyl, furyl in each case can be substituted up to two times by Cl, F, CN, $CF_3$, ($C_1$–$C_3$)-alkyl, OH, O—($C_1$–$C_6$)-alkyl; C(O)—($C_1$–$C_6$)-alkyl, C(O)—($C_3$–$C_6$)-cycloalkyl;
R3 is H, ($C_1$–$C_6$)-alkyl, F, CN, $N_3$, O—($C_1$–$C_6$)-alkyl, ($CH_2$)$_n$-phenyl, ($CH_2$)$_n$-thienyl, ($CH_2$)$_n$-pyridyl, ($CH_2$)$_n$-furyl, where n can be =0–5 and in which phenyl, thienyl, pyridyl, furyl in each case can be substituted up to two times by Cl, F, CN, $CF_3$, ($C_1$–$C_3$)-alkyl, OH, O—($C_1$–$C_6$)-alkyl; ($C_2$–$C_6$)-alkynyl, ($C_2$–$C_6$)-alkenyl, C(O)$OCH_3$, C(O)$OCH_2CH_3$, C(O)OH, C(O)$NH_2$, C(O)$NHCH_3$, C(O)N($CH_3$)$_2$, OC(O)$CH_3$;
R4 is ($C_1$–$C_6$)-alkyl, ($C_3$–$C_6$)-cycloalkyl, ($CH_2$)$_n$-phenyl, ($CH_2$)$_n$-thienyl, ($CH_2$)$_n$-pyridyl, ($CH_2$)$_n$-furyl, where n can be =0–5 and in which phenyl, thienyl, pyridyl, furyl in each case can be substituted up to two times by Cl, F, CN, $CF_3$, ($C_1$–$C_3$)-alkyl, OH, O—($C_1$–$C_6$)-alkyl;
R5 is ($C_1$–$C_6$)-alkyl, ($C_3$–$C_6$)-cycloalkyl, ($CH_2$)$_n$-phenyl, ($CH_2$)$_n$-thienyl, ($CH_2$)$_n$-pyridyl, ($CH_2$)$_n$-furyl, where n can be =0–5 and in which phenyl, thienyl, pyridyl, furyl in each case can be substituted up to two times by Cl, F, CN, $CF_3$, ($C_1$–$C_3$)-alkyl, OH, O—($C_1$–$C_6$)-alkyl;
or
R4 and R5 together form a —$CH_2$—$CH_2$—, —$CH_2$—C($CH_3$)$_2$—, —$CH_2$—$CH_2$—$CH_2$—, or —$CH_2$—$CH_2$—$CH_2$— group;
or
B)
Y is a direct bond, —$CH_2$— or —$CH_2$—$CH_2$—;
X is $CH_2$, $CH(CH_3)$, $CH(C_2H_5)$, $CH(C_3H_7)$;
R1 and R1' independently of one another are H, F, Cl, Br, I, $NO_2$, CN, COOH, COO($C_1$–$C_6$)-alkyl, $CONH_2$, CONH ($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-alkynyl, O—($C_1$–$C_6$)-alkyl, O—$CH_2$—$CF_3$, O—$CH_2$—$CF_2$—$CF_3$, O—($C_4$–$C_6$)-alkyl, where in the alkyl radicals one or more, or all hydrogen(s) can be replaced by fluorine, or one hydrogen can be replaced by OH, OC(O)$CH_3$, O—$CH_2$—Ph, $NH_2$ or N(COOCH$_2$Ph)$_2$;
S—($C_1$–$C_6$)-alkyl, S—($CH_2$)$_n$-phenyl, SO—($C_1$–$C_6$)-alkyl, SO—($CH_2$)$_n$-phenyl, $SO_2$—($C_1$–$C_6$)-alkyl, $SO_2$—($CH_2$)$_n$-phenyl, where n can be =0–6 and the phenyl radical can be substituted up to two times by F, Cl, Br, OH, $CF_3$, $NO_2$, CN, $OCF_3$, O—($C_1$–$C_6$)-alkyl, ($C_1$–$C_6$)-alkyl, $NH_2$; $SO_2$—$NH_2$, $SO_2NH(C_1$–$C_6)$-alkyl, $SO_2N$ [($C_1$–$C_6$)-alkyl]$_2$, $NH_2$, NH—($C_1$–$C_6$)-alkyl, N(($C_1$–$C_6$)-alkyl)$_2$, NH($C_1$–$C_7$)-acyl, phenyl, biphenyl, O—($CH_2$)$_n$-phenyl, where n can be =0 –6, 1- or 2-naphthyl, 2-, 3- or 4-pyridyl, 2- or 3-furanyl or 2- or 3-thienyl, where the phenyl, biphenyl, naphthyl, pyridyl, furanyl or thienyl rings in each case can be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl, $CONH_2$;
1,2,3-triazol-5-yl, where the triazole ring can be substituted in the 1-, 2- or 3-position by methyl or benzyl;
tetrazol-5-yl, where the tetrazole ring can be substituted in the 1- or 2-position by methyl or benzyl;
R2 is H, ($C_1$–$C_6$)-alkyl, ($C_3$–$C_6$)-cycloalkyl, ($CH_2$)$_n$-phenyl, ($CH_2$)$_n$-thienyl, ($CH_2$)$_n$-pyridyl, ($CH_2$)$_n$-furyl, C(O)—($CH_2$)$_n$-phenyl, C(O)—($CH_2$)$_n$thienyl, C(O)—($CH_2$)$_n$-pyridyl, C(O)—($CH_2$)$_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl; $C(O)-(C_1-C_6)$-alkyl, $C(O)-(C_3-C_6)$-cycloalkyl;

R3 is $(C_4-C_6)$-alkyl, F, CN, $N_3$, $O-(C_1-C_6)$-alkyl, $(CH_2)_n$-phenyl, $(CH_2)_n$-thienyl, $(CH_2)_n$-pyridyl, $(CH_2)_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl; $(C_2-C_6)$-alkynyl, $(C_2-C_6)$-alkenyl, $C(O)OCH_3$, $C(O)OCH_2CH_3$, $C(O)OH$, $C(O)NH_2$, $C(O)NHCH_3$, $C(O)N(CH_3)_2$, $OC(O)CH_3$;

R4 is $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl;

R5 is $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl;

or

R4 and R5 together form a $-CH_2-CH_2-$, $-CH_2-C(CH_3)_2-$, $-CH_2-CH_2-CH_2-$, or $-CH_2-CH_2-CH_2-CH_2-$ group;

or

C)

Y is a direct bond, $-CH_2-$ or $-CH_2-CH_2-$;

X is $CH_2$, $CH(CH_3)$, $CH(C_2H_5)$, $CH(C_3H_7)$;

R1 and R1' independently of one another are H, F, Cl, Br, I, $NO_2$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, $O-(C_1-C_6)$-alkyl, $O-CH_2-CF_3$, $O-CH_2-CF_2-CF_3$, $O-(C_4-C_6)$-alkyl, where in the alkyl radicals one or more, or all hydrogen(s) can be replaced by fluorine, or one hydrogen can be replaced by OH, $OC(O)CH_3$, $O-CH_2-Ph$, $NH_2$ or $N(COOCH_2Ph)_2$;
$S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, $SO_2-(CH_2)_n$-phenyl, where n can be =0–6 and the phenyl radical can be substituted up to two times by F, Cl, Br, OH, $CF_3$, $NO_2$, CN, $OCF_3$, $O-(C_1-C_6)$-alkyl, $(C_1-C_6)$-alkyl, $NH_2$; $SO_2-NH_2$, $SO_2NH(C_1-C_6)$-alkyl, $SO_2N[(C_1-C_6)$-alkyl$]_2$, $NH_2$, $NH-(C_1-C_6)$-alkyl, $N((C_1-C_6)$-alkyl$)_2$, $NH(C_1-C_7)$-acyl, phenyl, biphenyl, $O-(CH_2)_n$-phenyl, where n can be =0–6, 1- or 2-naphthyl, 2-, 3- or 4-pyridyl, 2- or 3-furanyl or 2- or 3-thienyl, where the phenyl, biphenyl, naphthyl, pyridyl, furanyl or thienyl rings in each case can be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, $CONH_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R2 is $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, $C(O)-(CH_2)_n$-phenyl, $C(O)-(CH_2)_n$-thienyl, $C(O)-(CH_2)_n$-pyridyl, $C(O)-(CH_2)_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl; $C(O)-(C_1-C_6)$-alkyl, $C(O)-(C_3-C_6)$-cycloalkyl;

R3 is H, $(C_1-C_6)$-alkyl, F, CN, $N_3$, $O-(C_1-C_6)$-alkyl, $(CH_2)_n$-phenyl, $(CH_2)_n$-thienyl, $(CH_2)_n$-pyridyl, $(CH_2)_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl; $(C_2-C_6)$-alkynyl, $(C_2-C_6)$-alkenyl, $C(O)OCH_3$, $C(O)OCH_2CH_3$, $C(O)OH$, $C(O)NH_2$, $C(O)NHCH_3$, $C(O)N(CH_3)_2$, $OC(O)CH_3$;

R4 is $(C_1-C_6)$-alkyl, $(C_3-C_6)$-cycloalkyl, $(CH_2)_n$-phenyl, $(CH_2)_n$-thienyl $(CH_2)_n$-pyridyl, $(CH_2)_n$-furyl, where n can be =0–5 and in which phenyl, thienyl, pyridyl, furyl in each case can be substituted up to two times by Cl, F, CN, $CF_3$, $(C_1-C_6)$-alkyl, OH, $O-(C_1-C_6)$-alkyl;

R5 is $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl;

or

R4 and R5 together form a $-CH_2-CH_2-$, $-CH_2-C(CH_3)_2-$, $-CH_2-CH_2-CH_2-$, or $-CH_2-CH_2-CH_2-CH_2-$ group;

or

D)

Y is a direct bond, $-CH_2-$ or $-CH_2-CH_2-$;

X is CH(phenyl), where the phenyl radical can be substituted by F, Cl, Br or I, O, S, SO, $S_2$ or $N-R_6$;

R1 and R1' independently of one another are H, F, Cl, Br, I, $NO_2$, CN, COOH, $COO(C_1-C_6)$-alkyl, $CONH_2$, $CONH(C_1-C_6)$-alkyl, $CON[(C_1-C_6)$-alkyl$]_2$, $(C_1-C_6)$-alkyl, $(C_2-C_6)$-alkenyl, $(C_2-C_6)$-alkynyl, $O-(C_1-C_6)$-alkyl, $O-CH_2-CF_3$, $O-CH_2-CF_2-CF_3$, $O-(C_4-C_6)$-alkyl, where in the alkyl radicals one or more, or all hydrogen(s) can be replaced by fluorine, or one hydrogen can be replaced by OH, $OC(O)CH_3$, $O-CH_2-Ph$, $NH_2$ or $N(COOCH_2Ph)_2$;
$S-(C_1-C_6)$-alkyl, $S-(CH_2)_n$-phenyl, $SO-(C_1-C_6)$-alkyl, $SO-(CH_2)_n$-phenyl, $SO_2-(C_1-C_6)$-alkyl, $SO_2-(CH_2)_n$-phenyl, where n can be =0–6 and the phenyl radical can be substituted up to two times by F, Cl, Br, OH, $CF_3$, $NO_2$, CN, $OCF_3$, $O-(C_1-C_6)$-alkyl, $(C_1-C_6)$-alkyl, $NH_2$; $SO_2-NH_2$, $SO_2NH(C_1-C_6)$-alkyl, $SO_2N[(C_1-C_6)$-alkyl$]_2$, $NH_2$, $NH-(C_1-C_6)$-alkyl, $N((C_1-C_6)$-alkyl$)_2$, $NH(C_1-C_7)$-acyl, phenyl, biphenyl, $O-(CH_2)_n$-phenyl, where n can be =0–6, 1- or 2-naphthyl, 2-, 3- or 4-pyridyl, 2- or 3-furanyl or 2- or 3-thienyl, where the phenyl, biphenyl, naphthyl, pyridyl, furanyl or thienyl rings in each case can be substituted one to 3 times by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, COOH, $COO-(C_1-C_6)$-alkyl, $CONH_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R2 is H, $(C_1-C_6)$-alkyl, $(C_3-C_6)$-cycloalkyl, $(CH_2)$-phenyl, $(CH_2)_n$-thienyl, $(CH_2)_n$-pyridyl, $(CH_2)_n$-furyl, $C(O)-(CH_2)_n$-phenyl, $C(O)-(CH_2)_n$-thienyl, $C(O)-(CH_2)_n$-pyridyl, $C(O)-(CH_2)_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl; $C(O)-(C_1-C_6)$-alkyl, $C(O)-(C_3-C_6)$-cycloalkyl;

R3 is H, $(C_1-C_6)$-alkyl, F, CN, $N_3$, $O-(C_1-C_6)$-alkyl, $(CH_2)_n$-phenyl, $(CH_2)_n$-thienyl, $(CH_2)_n$-pyridyl, $(CH_2)_n$-furyl, where n can be =0–5 and in which phenyl, thienyl, pyridyl, furyl in each case can be substituted up to two times by Cl, F, CN, $CF_3$, $(C_1-C_3)$-alkyl, OH, $O-(C_1-C_6)$-alkyl; $(C_2-C_6)$-alkynyl, $(C_2-C_6)$-alkenyl, C(O)OCH$_3$, C(O)OCH$_2$CH$_3$, C(O)OH, C(O)NH$_2$, C(O)NHCH$_3$, C(O)N(CH$_3$)$_2$, OC(O)CH$_3$;

R4 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, where n can be =0–5 and in which phenyl, thienyl, pyridyl, furyl in each case can be substituted up to two times by Cl, F, CN, CF$_3$, (C$_1$–C$_3$)-alkyl, OH, O—(C$_1$–C$_6$)-alkyl;

R5 is (C$_1$–C$_6$)-alkyl, (C$_3$–C$_6$)-cycloalkyl, (CH$_2$)$_n$-phenyl, (CH$_2$)$_n$-thienyl, (CH$_2$)-pyridyl, (CH$_2$)$_n$-furyl, where n can be =0–5 and in which phenyl, thienyl, pyridyl, furyl in each case can be substituted up to two times by Cl, F, CN, CF$_3$, (C$_1$–C$_3$)-alkyl, OH, O—(C$_1$–C$_6$)-alkyl;

or

R4 and R5 together form a —CH$_2$—CH$_2$—, —CH$_2$—C(CH$_3$)$_2$—, —CH$_2$—CH$_2$—CH$_2$—, or —CH$_2$—CH$_2$—CH$_2$—CH$_2$-group;

R6 is SO$_2$—(C$_6$H$_4$-4-CH$_3$)

or

E)

Y is a direct bond, —CH$_2$— or —CH$_2$—CH$_2$—;

X is CH$_2$, CH(CH$_3$), CH(C$_2$H$_5$), CH(C$_3$H$_7$);

R1 is H, F, Cl, Br, I, CH$_3$, CF$_3$, O—(C$_1$–C$_3$)-alkyl;

R1' is H, F, Cl, Br, I, NO$_2$;

R2 is H;

R3 is H, (C$_1$–C$_3$)-alkyl;

R4 is phenyl, where the phenyl radical can be substituted up to two times by F, Cl, Br, I, (C$_1$–C$_6$)-alkyl, (C$_3$–C$_6$)-cycloalkyl, O—(C$_1$–C$_3$)-alkyl, CF$_3$, OCF$_3$, O—CH$_2$-phenyl, COOH, COO(C$_1$–C$_6$)-alkyl, COO(C$_3$–C$_6$)-cycloalkyl, CONH$_2$;

R5 is phenyl, where the phenyl radical can be substituted up to two times by F, Cl, Br, I, (C$_1$–C$_6$)-alkyl, (C$_3$–C$_6$)-cycloalkyl, O—(C$_1$–C$_3$)-alkyl, CF$_3$, OCF$_3$, O—CH$_2$-phenyl, COOH, COO(C$_1$–C$_6$)-alkyl, COO(C$_3$–C$_6$)-cycloalkyl, CONH$_2$;

and their physiologically tolerable salts and physiologically functional derivatives.

The invention also relates to pharmaceutical compositions including such compounds, and to method of treating obesity and diabetes using such compounds.

Further objects, features and advantages of the inventions will become apparent from the detailed description of preferred embodiments that follows.

DETAILED DESCRIPTION OF THE PREFERRED EMBODIMENTS

Preferred compounds of the formula I are those in which

A)

Y is a direct bond, or —CH$_2$;

X is CH$_2$, CH(CH$_3$), CH(C$_2$H$_5$), or CH(C$_3$H$_7$);

R1 is CN, COOH, COO(C$_1$–C$_6$)-alkyl, CONH$_2$, CONH(C$_1$–C$_6$)-alkyl, CON[(C$_1$–C$_6$)-alkyl]$_2$, (C$_2$–C$_6$)-alkyl, (C$_2$–C$_6$)-alkenyl, (C$_2$–C$_6$)-alkynyl, O—CH$_2$—CF$_3$, O—CH$_2$—CF$_2$—CF$_3$, O—(C$_4$–C$_6$)-alkyl, where in the alkyl radicals one or more, or all hydrogen(s) can be replaced by fluorine, or one hydrogen can be replaced by OH, OC(O)CH$_3$, O—CH$_2$—Ph, NH$_2$ or N(COOCH$_2$Ph)$_2$; S—(C$_1$–C$_6$)-alkyl, S—(CH$_2$)$_n$-phenyl, SO—(C$_1$–C$_6$)-alkyl, SO—(CH$_2$)$_n$-phenyl, where the phenyl radical can be substituted up to two times by F, Cl, Br, OH, CF$_3$, NO$_2$, CN, OCF$_3$, O—(C$_1$–C$_6$)-alkyl, (C$_1$–C$_6$)-alkyl; NH—(C$_1$–C$_6$)-alkyl, N((C$_1$–C$_6$)-alkyl)$_2$, NH(C$_1$–C$_7$)-acyl, phenyl, O—(CH$_2$)$_n$-phenyl, where n can be =0–6, 1- or 2-naphthyl, 2—, 3- or 4-pyridyl, 2- or 3-furanyl or 2- or 3-thienyl, where the phenyl, biphenyl, naphthyl, pyridyl, furanyl or thienyl rings in each case can be substituted one to 3 times by F, Cl, I, OH, CF$_3$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, COOH, COO—(C$_1$–C$_6$)-alkyl, CONH$_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R1' is H, F, Cl, Br, I, CH$_3$, CF$_3$, O—(C$_1$–C$_3$)-alkyl, SO$_2$–NH$_2$, SO$_2$NH(C$_1$–C$_6$)-alkyl, SO$_2$N[(C$_1$–C$_6$)-alkyl]$_2$ or R1;

R2 is H, (C$_1$–C$_6$)-alkyl, (CH$_2$)-phenyl, (CH$_2$)$_n$-thienyl, (CH$_2$)$_n$-pyridyl, C(O)—(CH$_2$)$_n$-phenyl, C(O)—(CH$_2$)$_n$-thienyl, C(O)—(CH$_2$)$_n$-pyridyl, where n can be =0–3 and in which phenyl, thienyl, pyridyl, furyl in each case can be substituted up to two times by Cl, F, CN, CF$_3$, (C$_1$–C$_3$)-alkyl, OH, O—(C$_1$–C$_6$)-alkyl;

R3 is H, (C$_1$–C$_6$)-alkyl, F, CN, O—(C$_1$–C$_6$)-alkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl; (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)N(CH$_3$)$_2$, OC(O)CH$_3$;

R4 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl;

R5 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl;

or

R4 and R5 together form a —CH$_2$—CH$_2$—, —CH$_2$—C(CH$_3$)$_2$— or —CH$_2$—CH$_2$—CH$_2$- group;

or

B)

Y is a direct bond, —CH$_2$—;

X is CH$_2$, CH(CH$_3$), CH(C$_2$H$_5$), CH(C$_3$H$_7$);

R1 and R1' independently of one another are H, F, Cl, Br, I, CN, COOH, COO(C$_1$–C$_6$)-alkyl, CONH$_2$, CONH(C$_1$–C$_6$)-alkyl, CON[(C$_1$–C$_6$)-alkyl]$_2$, (C$_1$–C$_6$)-alkyl, (C$_2$–C$_6$)-alkenyl, (C$_2$–C$_6$)-alkynyl, O—(C$_1$–C$_6$)-alkyl, O—CH$_2$—CF$_3$, O—CH$_2$CF$_2$—CF$_3$, O—(C$_4$–C$_6$)-alkyl, where in the alkyl radicals one or more, or all hydrogen(s) can be replaced by fluorine, or one hydrogen can be replaced by OH, OC(O)CH$_3$, O—CH$_2$—Ph, NH$_2$ or N(COOCH$_2$Ph)$_2$;

S—(C$_1$–C$_6$)-alkyl, S—(CH$_2$)$_n$-phenyl, SO—(C$_1$–C$_6$)-alkyl, SO—(CH$_2$)$_n$-phenyl, where the phenyl radical can be substituted up to two times by F, Cl, Br, OH, CF$_3$, NO$_2$, CN, OCF$_3$, O—(C$_1$–C$_6$)-alkyl, (C$_1$–C$_6$)-alkyl; SO$_2$—NH$_2$, SO$_2$NH(C$_1$–C$_6$)-alkyl, SO$_2$N[(C$_1$–C$_6$)-alkyl]$_2$, NH—(C$_1$–C$_6$)-alkyl, N((C$_1$–C$_6$)-alkyl)$_2$, NH(C$_1$–C$_7$)-acyl, phenyl, O—(CH$_2$)$_n$-phenyl, where n can be =0–6, 1- or 2-naphthyl, 2, 3- or 4-pyridyl, 2- or 3-furanyl or 2- or 3-thienyl, where the phenyl, naphthyl, pyridyl, furanyl or thienyl rings in each case can be substituted one to 3 times by F, Cl, I, OH, CF$_3$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, COOH, COO-(C$_1$–C$_6$)-alkyl, CONH$_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R2 is H, (C$_1$–C$_6$)-alkyl, (CH$_2$)$_n$-phenyl, (CH$_2$)$_n$-thienyl, (CH$_2$)$_n$-pyridyl, C(O)—(CH$_2$)$_n$-phenyl, C(O)—(CH$_2$)$_n$- thienyl, C(O)—(CH$_2$)$_n$-pyridyl, where n can be =0–3 and in which phenyl, thienyl, pyridyl, furyl in each case can be substituted up to two times by Cl, F, CN, CF$_3$, (C$_1$–C$_3$)-alkyl, OH, O—(C$_1$–C$_6$)-alkyl;

R3 is (C$_4$–C$_6$)-alkyl, F, CN, N$_3$, O—(C$_1$–C$_6$)-alkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl; (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$, OC(O)CH$_3$;

R4 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl;

R5 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl;

or

R4 and R5 together form a —CH$_2$—CH$_2$—, —CH$_2$—C(CH$_3$)$_2$— —CH$_2$—CH$_2$—CH$_2$- group;

or

C)

Y is a direct bond, or —CH$_2$—;

X is CH$_2$, CH(CH$_3$), CH(C$_2$H$_5$), CH(C$_3$H$_7$);

R1 and R1' independently of one another are H, F, Cl, Br, I, CN, COOH, COO(C$_1$–C$_6$)-alkyl, CONH$_2$, CONH(C$_1$–C$_6$)-alkyl, CON[(C$_1$–C$_6$)-alkyl]$_2$, (C$_1$–C$_6$)-alkyl, (C$_2$–C$_6$)-alkenyl, (C$_2$–C$_6$)-alkynyl, O—(C$_1$–C$_6$)-alkyl, O—CH$_2$—CF$_3$, O—CH$_2$—CF$_2$—CF$_3$, O—(C$_4$–C$_6$)-alkyl, where in the alkyl radicals one or more, or all hydrogen(s) can be replaced by fluorine, or one hydrogen can be replaced by OH, OC(O)CH$_3$, O—CH$_2$—Ph, NH$_2$ or N(COOCH$_2$Ph)$_2$;

S—(C$_1$–C$_6$)-alkyl, S—(CH$_2$)$_n$-phenyl, SO$_2$—(C$_1$–C$_6$)-alkyl, SO$_2$—(CH$_2$)$_n$-phenyl, where n can be =0–6 and the phenyl radical can be substituted up to two times by F, Cl, Br, OH, CF$_3$, NO$_2$, CN, OCF$_3$, O—(C$_1$–C$_6$)-alkyl, (C$_1$–C$_6$)-alkyl; SO$_2$—NH$_2$, SO$_2$NH(C$_1$–C$_6$)-alkyl, SO$_2$N[(C$_1$–C$_6$)-alkyl]$_2$, NH—(C$_1$–C$_6$alkyl, N((C$_1$–C$_6$)-alkyl)$_2$, NH(C$_1$–C$_7$)-acyl, phenyl, O—(CH$_2$)$_n$-phenyl, where n can be =0–4, 1- or 2-naphthyl, 2-, 3- or 4-pyridyl, 2- or 3-furanyl or 2- or 3-thienyl, where the phenyl, naphthyl, pyridyl, furanyl or thienyl rings in each case can be substituted one to 3 times by F, Cl, I, OH, CF$_3$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, COOH, COO—(C$_1$–C$_6$)-alkyl, CONH$_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R2 is (C$_1$–C$_6$)-alkyl, (CH$_2$)$_n$-phenyl, (CH$_2$)$_n$-thienyl, (CH$_2$)$_n$-pyridyl, C(O)—(CH$_2$)$_n$-phenyl, C(O)—(CH$_2$)$_n$-thienyl, C(O)—(CH$_2$)$_n$-pyridyl, where n can be =0–3 and in which phenyl, thienyl, pyridyl, furyl in each case can be substituted up to two times by Cl, F, CN, CF$_3$, (C$_1$–C$_3$)-alkyl, OH, O—(C$_1$–C$_6$)-alkyl;

R3 is H, (C$_1$–C$_6$)-alkyl, F, CN, O—(C$_1$–C$_6$)-alkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl; (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)N(CH$_3$)$_2$, OC(O)CH$_3$; p0 R4 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl;

R5 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl;

or

R4 and R5 together form a —CH$_2$—CH$_2$—, —CH$_2$—C(CH$_3$)$_2$— or —CH$_2$—CH$_2$—CH$_2$- group;

or

D)

Y is a direct bond, or —CH$_2$—;

X is CH(phenyl), where the phenyl radical can be substituted by F, Cl or Br, O, S, SO, SO$_2$ or N—R$_6$;

R1 and R1' independently of one another are H, F, Cl, Br, I, CN, COOH, COO(C$_1$–C$_6$)-alkyl, CONH$_2$, CONH(C$_1$–C$_6$)-alkyl, CON[(C$_1$–C$_6$)-alkyl]$_2$, (C$_1$–C$_6$)-alkyl, (C$_2$–C$_6$)-alkenyl, (C$_2$–C$_6$)-alkynyl, O—(C$_1$–C$_6$)-alkyl, O—CH$_2$—CF$_3$, O—CH$_2$—CF$_2$—CF$_3$, O—(C$_4$–C$_6$)-alkyl, where in the alkyl radicals one or more, or all hydrogen(s) can be replaced by fluorine, or one hydrogen can be replaced by OH, OC(O)CH$_3$, O—CH$_2$—Ph, NH$_2$ or N(COOCH$_2$Ph)$_2$;

S—(C$_1$–C$_6$)-alkyl, S—(CH$_2$)$_n$-phenyl, SO$_2$—(C$_1$–C$_6$)-alkyl, SO$_2$—(CH$_2$)$_n$-phenyl, where n can be =0–6 and the phenyl radical can be substituted up to two times by F, Cl, Br, OH, CF$_3$, NO$_2$, CN, OCF$_3$, O—(C$_1$–C$_6$)-alkyl, (C$_1$–C$_6$)-alkyl; SO$_2$—NH$_2$, SO$_2$NH(C$_1$–C$_6$)-alkyl, SO$_2$N[(C$_1$–C$_6$)-alkyl]$_2$, NH$_2$, NH—(C$_1$–C$_6$)-alkyl, N((C$_1$–C$_6$)-alkyl)$_2$, NH(C$_1$–C$_7$)-acyl, phenyl, O—(CH$_2$)$_n$-phenyl, where n can be =0–6, 1- or 2-naphthyl, 2-, 3- or 4-pyridyl, 2- or 3-furanyl or 2- or 3-thienyl, where the phenyl, naphthyl, pyridyl, furanyl or thienyl rings in each case can be substituted one to 3 times by F, Cl, I, OH, CF$_3$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, COOH, COO—(C$_1$–C$_6$)-alkyl, CONH$_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R2 is H, (C$_1$–C$_6$)-alkyl, (CH$_2$)$_n$-phenyl, (CH$_2$)$_n$-thienyl, (CH$_2$)$_n$-pyridyl, C(O)—(CH$_2$)$_n$-phenyl, C(O)—(CH$_2$)$_n$-thienyl, C(O)—(CH$_2$)$_n$-pyridyl, where n can be =0–3 and in which phenyl, thienyl, pyridyl, furyl in each case can be substituted up to two times by Cl, F, CN, CF$_3$, (C$_1$–C$_3$)-alkyl, OH, O—(C$_1$–C$_6$)-alkyl;

R3 is H, (C$_1$–C$_6$)-alkyl, F, CN, O—(C$_1$–C$_6$)-alkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl; (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$, OC(O)CH$_3$;

R4 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, CF$_3$, (C$_1$–C$_3$)-alkyl, OH, O—(C$_1$–C$_6$)-alkyl;

R5 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, where n can be =0–3 and in which phenyl, thienyl, pyridyl in each case can be substituted up to two times by Cl, F, CN, $CF_3$, $(C_1-C_3)$-alkyl, OH, O—$(C_1-C_6)$-alkyl;

or

R4 and R5 together form a —$CH_2$—$CH_2$—, —$CH_2$—C$(CH_3)_2$— or —$CH_2$—$CH_2$—$CH_2$— group;

R6 is $SO_2$—$(C_6H_4$-4-$CH_3)$ or

E)

Y is a direct bond or —$CH_2$—;

X is $CH_2$, $CH(CH_3)$, $CH(C_2H_5)$, $CH(C_3H_7)$;

R1 is H, F, Cl, Br, I, $CH_3$, $CF_3$, O—$(C_1-C_3)$-alkyl;

R1' is H, F, Cl, Br, I;

R2 is H;

R3 is H, $(C_1-C_3)$-alkyl;

R4 is phenyl, where the phenyl radical can be substituted up to two times by F, Cl, Br, I, $(C_1-C_6)$-alkyl, $(C_3-C_6)$-cycloalkyl, O—$(C_1-C_3)$-alkyl, $CF_3$, $OCF_3$, O—$CH_2$-phenyl, COOH, COO$(C_1-C_6)$-alkyl, $CONH_2$;

R5 is phenyl, where the phenyl radical can be substituted up to two times by F, Cl, Br, I, $(C_1-C_6)$-alkyl, $(C_3-C_6)$-cycloalkyl, O—$(C_1-C_3)$-alkyl, $CF_3$, $OCF_3$, O—$CH_2$-phenyl, COOH, COO$(C_1-C_6)$-alkyl, $CONH_2$;

and their physiologically tolerable salts and physiologically functional derivatives.

Particularly preferred compounds of the formula I are those in which

A)

Y is a direct bond;

X is $CH_2$, $CH(CH_3)$, $CH(C_2H_5)$, $CH(C_3H_7)$;

R1 is CN, COOH, COO$(C_1-C_6)$-alkyl, $CONH_2$, CON$[(C_1-C_6)$-alkyl$]_2$, $(C_2-C_6)$-alkyl; $(C_2-C_6)$-alkenyl; $(C_2-C_6)$-alkynyl; O—$CH_2$—$CF_3$, O—$CH_2$—$CF_2$—$CF_3$, O—$(C_4-C_6)$-alkyl, where in the alkyl radicals one or more, or all hydrogen(s) can be replaced by fluorine, or one hydrogen can be replaced by OH, $OC(O)CH_3$, O—$CH_2$—Ph, $NH_2$ or N(COOCH$_2$Ph)$_2$;
S—$(C_1-C_6)$-alkyl, S—$(CH_2)_n$-phenyl, SO—$(C_1-C_6)$-alkyl, SO—$(CH_2)_n$-phenyl, where the phenyl radical can be substituted up to two times by F, Cl, Br, OH, $CF_3$, $NO_2$, CN, $OCF_3$, O—$(C_1-C_6)$-alkyl, $(C_1-C_6)$-alkyl; NH—$(C_1-C_6)$-alkyl, N$((C_1-C_6)$-alkyl$)_2$, NH$(C_1-C_7)$-acyl, phenyl, O—$(CH_2)_n$-phenyl, where n can be =0–6, 1- or 2-naphthyl, 2-, 3- or 4-pyridyl, 2- or 3-furanyl or 2- or 3-thienyl, where the phenyl, naphthyl, pyridyl, furanyl or thienyl rings in each case can be substituted one to 2 times by F, Cl, OH, $CF_3$, CN, $OCF_3$, O—$(C_1-C_6)$-alkyl, $(C_1-C_6)$-alkyl, COOH, COO—$(C_1-C_6)$-alkyl, $CONH_2$;
1,2,3-triazol-5-yl, where the triazole ring can be substituted in the 1-, 2- or 3-position by methyl or benzyl;
tetrazol-5-yl, where the tetrazole ring can be substituted in the 1- or 2-position by methyl or benzyl;

R1' is H, F, Cl, $CH_3$, $CF_3$, O—$(C_1-C_3)$-alkyl, $SO_2$-$NH_2$, $SO_2NH(C_1-C_6)$-alkyl, $SO_2N[(C_1-C_6)$-alkyl$]_2$ or R1;

R2 is H, $(C_1-C_6)$-alkyl, $(CH_2)_n$-phenyl, $(CH_2)_n$-pyridyl, C(O)—$(CH_2)_n$-phenyl, C(O)—$(CH_2)_n$-pyridyl, where n can be =0–3 and in which phenyl, pyridyl in each case can be substituted up to two times by Cl, F, CN, $CF_3$, $(C_1-C_3)$-alkyl, O—$(C_1-C_6)$-alkyl; C(O)—$(C_1-C_6)$-alkyl;

R3 is H, $(C_1-C_6)$-alkyl, F, CN, O—$(C_1-C_6)$-alkyl, $(CH_2)_n$-phenyl, $(CH_2)_n$-pyridyl, where n can be =0–3 and in which phenyl, pyridyl in each case can be substituted up to two times by Cl, F, CN, $CF_3$, $(C_1-C_3)$-alkyl, O—$(C_1-C_6)$-alkyl; $(C_2-C_6)$-alkynyl, $C(O)OCH_3$, $C(O)OCH_2CH_3$, C(O)OH, $C(O)NH_2$, $C(O)N(CH_3)_2$, $OC(O)CH_3$;

R4 is $(C_1-C_6)$-alkyl, $(C_3-C_6)$-cycloalkyl, $(CH_2)_n$-phenyl, $(CH_2)_n$-pyridyl, where n can be =0–3 and in which phenyl, pyridyl in each case can be substituted up to two times by Cl, F, CN, $CF_3$, $(C_1-C_3)$-alkyl, O—$(C_1-C_6)$-alkyl;

R5 is $(C_1-C_6)$-alkyl, $(C_3-C_6)$-cycloalkyl, $(CH_2)_n$-phenyl, $(CH_2)_n$-pyridyl, where n can be =0–3 and in which phenyl, pyridyl in each case can be substituted up to two times by Cl, F, CN, $CF_3$, $(C_1-C_3)$-alkyl, O—$(C_1-C_6)$-alkyl;

or

R4 and R5 together form a —$CH_2$—$CH_2$—, —$CH_2$—C$(CH_3)_2$— or —$CH_2$—$CH_2$—$CH_2$— group;

or

B)

Y is a direct bond, —$CH_2$—;

X is $CH_2$, $CH(CH_3)$, $CH(C_2H_5)$, $CH(C_3H_7)$;

R1 and R1' independently of one another are H, F, Cl, Br, I, CN, COOH, COO$(C_1-C_6)$-alkyl, $CONH_2$, CON$[(C_1-C_6)$-alkyl$]_2$, $(C_1-C_6)$-alkyl, $(C_2-C_6)$-alkenyl, $(C_2-C_6)$-alkynyl, O—$(C_1C_6)$-alkyl, O—$CH_2$—$CF_3$, O—$CH_2$—$CF_2$—$CF_3$, O—$(C_4-C_6)$-alkyl, where in the alkyl radicals one or more, or all hydrogen(s) can be replaced by fluorine, or one hydrogen can be replaced by OH, $OC(O)CH_3$, O—$CH_2$—Ph, $NH_2$ or N(COOCH$_2$Ph)$_2$;
S—$(C_1-C_6)$-alkyl, S—$(CH_2)_n$-phenyl, SO—$(C_1-C_6)$-alkyl, SO—$(CH_2)_n$-phenyl, where the phenyl radical can be substituted up to two times by F, Cl, OH, $CF_3$, $OCF_3$, O—$(C_{1-6})$-alkyl, $(C_1-C_6)$-alkyl; $SO_2$—$NH_2$, $SO_2NH(C_1-C_6)$-alkyl, $SO_2N[(C_1-C_6)$-alkyl$]_2$, N$((C_1-C_6)$-alkyl$)_2$, NH$(C_1-C_7)$-acyl, phenyl, O—$(CH_2)_n$-phenyl, where n can be =0–6, 1- or 2-naphthyl, 2-, 3- or 4-pyridyl, 2- or 3-furanyl or 2- or 3-thienyl, where the phenyl, naphthyl, pyridyl, furanyl or thienyl rings in each case can be substituted one to 3 times by F, Cl, I, OH, $CF_3$, CN, $OCF_3$, O—$(C_1-C_6)$-alkyl, $(C_1-C_6)$-alkyl, $NH_2$, N$((C_1-C_6)$-alkyl$)_2$, COOH, COO—$(C_1-C_6)$-alkyl, $CONH_2$;
1,2,3-triazol-5-yl, where the triazole ring can be substituted in the 1-, 2- or 3-position by methyl or benzyl;
tetrazol-5-yl, where the tetrazole ring can be substituted in the 1- or 2-position by methyl or benzyl;

R2 is H, $(C_1-C_6)$-alkyl, $(CH_2)_n$-phenyl, $(CH_2)_n$-pyridyl, C(O)—$(CH_2)_n$-phenyl, C(O)—$(CH_2)_n$-pyridyl, where n can be =0–3 and in which phenyl, pyridyl in each case can be substituted up to two times by Cl, F, CN, $CF_3$, $(C_1-C_3)$-alkyl, OH, O—$(C_1-C_6)$-alkyl; C(O)—$(C_1-C_6)$-alkyl;

R3 is $(C_4-C_6)$-alkyl, F, CN, $N_3$, O—$(C_1-C_6)$-alkyl, $(CH_2)_n$-phenyl, $(CH_2)_n$-pyridyl, where n can be =0–3 and in which phenyl, pyridyl in each case can be substituted up to two times by Cl, F, CN, $CF_3$, $(C_1-C_3)$-alkyl, O—$(C_1-C_6)$-alkyl; $(C_2-C_6)$-alkynyl, $C(O)OCH_3$, $C(O)OCH_2CH_3$, C(O)OH, $C(O)NH_2$, $C(O)NHCH_3$, $C(O)N(CH_3)_2$, $OC(O)CH_3$;

R4 is $(C_1-C_6)$-alkyl, $(C_3-C_6)$-cycloalkyl, $(CH_2)_n$-phenyl, $(CH_2)_n$-pyridyl, where n can be =0–3 and in which phenyl, pyridyl in each case can be substituted up to two times by Cl, F, CN, $CF_3$, $(C_1-C_3)$-alkyl, O—$(C_1-C_6)$-alkyl;

R5 is $(C_1-C_6)$-alkyl, $(C_3-C_6)$-cycloalkyl, $(CH_2)_n$-phenyl, $(CH_2)_n$-pyridyl, where n can be =0–3 and in which phenyl, pyridyl in each case can be substituted up to two times by Cl, F, CN, $CF_3$, $(C_1-C_3)$-alkyl, O—$(C_1-C_6)$-alkyl;

or

R4 and R5 together form a —$CH_2$—$CH_2$—, —$CH_2$—C$(CH_3)_2$— or —$CH_2$—$CH_2$—$CH_2$— group;

or

C)

Y is a direct bond or —$CH_2$—;

X is $CH_2$, $CH(CH_3)$, $CH(C_2H_5)$, $CH(C_3H_7)$;

R1 and R1' independently of one another are H, F, Cl, Br, I, CN, COOH, COO($C_1$–$C_6$)-alkyl, $CONH_2$, CON[($C_1$–$C_6$)-alkyl]$_2$, ($C_1$–$C_6$)-alkyl, ($C_2$–$C_6$)-alkenyl, ($C_2$–$C_6$)-alkynyl, O—($C_1$–$C_6$)-alkyl, O—$CH_2$—$CF_3$, O—$CH_2$—$CF_2$—$CF_3$, O—($C_4$–$C_6$)-alkyl, where in the alkyl radicals one or more, or all hydrogen(s) can be replaced by fluorine, or one hydrogen can be replaced by OH, OC(O)$CH_3$, O—$CH_2$—Ph, $NH_2$ or N(COO$CH_2$Ph)$_2$; S—($C_1$–$C_6$)-alkyl, S—($CH_2$)$_n$-phenyl, $SO_2$—($C_1$–$C_6$)-alkyl, $SO_2$—($CH_2$)$_n$-phenyl, where n can be =0–6 and the phenyl radical can be substituted up to two times by F, Cl, Br, OH, $CF_3$, $NO_2$, $OCF_3$, O—($C_1$–$C_6$)-alkyl, ($C_1$–$C_6$)-alkyl; $SO_2$—$NH_2$, $SO_2NH$($C_1$–$C_6$)-alkyl, $SO_2$N[($C_1$–$C_6$)-alkyl]$_2$, N(($C_1$–$C_6$)-alkyl)$_2$, NH($C_1$–$C_7$)-acyl, phenyl, O—($CH_2$)$_n$-phenyl, where n can be =0–4, 1- or 2-naphthyl, 2-, 3- or 4-pyridyl, 2- or 3-furanyl or 2- or 3-thienyl, where the phenyl, naphthyl, pyridyl, furanyl or thienyl rings in each case can be substituted one to 3 times by F, Cl, I, OH, $CF_3$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, COOH, COO—($C_1$–$C_6$)-alkyl, $CONH_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R2 is ($C_1$–$C_6$)-alkyl, ($CH_2$)$_n$-phenyl, ($CH_2$)$_n$-thienyl, ($CH_2$)$_n$-pyridyl, C(O)—($CH_2$)$_n$-phenyl, C(O)—($CH_2$)$_n$-thienyl, C(O)—($CH_2$)$_n$-pyridyl, where n can be =0–3 and in which phenyl, thienyl, pyridyl, furyl in each case can be substituted up to two times by Cl, F, CN, $CF_3$, ($C_1$–$C_3$)-alkyl, OH, O—($C_1$–$C_6$)-alkyl; C(O)—($C_1$–$C_6$)-alkyl;

R3 is H, ($C_1$–$C_6$)-alkyl, F, CN, O—($C_1$–$C_6$)-alkyl, ($CH_2$)$_n$-phenyl, ($CH_2$)$_n$-pyridyl, where n can be =0–3 and in which phenyl, pyridyl in each case can be substituted up to two times by Cl, F, CN, $CF_3$, ($C_1$–$C_3$)-alkyl, O—($C_1$–$C_6$)-alkyl; ($C_2$–$C_6$)-alkynyl, C(O)O$CH_3$, C(O)O$CH_2CH_3$, C(O)OH, C(O)$NH_2$, C(O)N($CH_3$)$_2$, OC(O)$CH_3$;

R4 is ($C_1$–$C_6$)-alkyl, ($C_3$–$C_6$)-cycloalkyl, ($CH_2$)$_n$-phenyl, ($CH_2$)$_n$-pyridyl, where n can be =0–3 and in which phenyl, pyridyl in each case can be substituted up to two times by Cl, F, CN, $CF_3$, ($C_1$–$C_3$)-alkyl, O—($C_1$–$C_6$)-alkyl;

R5 is ($C_1$–$C_6$)-alkyl, ($C_3$–$C_6$)-cycloalkyl, ($CH_2$)$_n$-phenyl, ($CH_2$)$_n$-pyridyl, where n can be =0–3 and in which phenyl, pyridyl in each case can be substituted up to two times by Cl, F, CN, $CF_3$, ($C_1$–$C_3$)-alkyl, O—($C_1$–$C_6$)-alkyl;

or

R4 and R5 together form a —$CH_2$—$CH_2$—, —$CH_2$—C($CH_3$)$_2$— or —$CH_2$—$CH_2$—$CH_2$— group;

or

D)

Y is a direct bond or —$CH_2$—;

X is CH(phenyl), where the phenyl radical can be substituted by F or Cl, O,S, $SO_2$ or N—R6;

R1 and R1' independently of one another are H, F, Cl, Br, I, CN, COOH, COO($C_1$–$C_6$)-alkyl, $CONH_2$, CON[($C_1$–$C_6$)-alkyl]$_2$, ($C_1$–$C_6$)-alkyl, ($C_2$–$C_6$)-alkenyl, ($C_2$–$C_6$)-alkynyl, O—($C_1$–$C_6$)-alkyl, O—$CH_2$—$CF_3$, O—$CH_2$—$CF_2$—$CF_3$, O—($C_4$–$C_6$)-alkyl, where in the alkyl radicals one or more, or all hydrogen(s) can be replaced by fluorine, or one hydrogen can be replaced by OH, OC(O)$CH_3$, O—$CH_2$—Ph, $NH_2$ or N(COO$CH_2$Ph)$_2$; S—($C_1$–$C_6$)-alkyl, S—($CH_2$)$_n$-phenyl, $SO_2$—($C_1$–$C_6$)-alkyl, $SO_2$—($CH_2$)$_n$-phenyl, where n can be =0–6 and the phenyl radical can be substituted up to two times by F, Cl, Br, OH, $CF_3$, $NO_2$, CN, $OCF_3$, O—($C_1$–$C_6$)-alkyl, ($C_1$–$C_6$)-alkyl; $SO_2$—$NH_2$, $SO_2NH$($C_1$–$C_6$)-alkyl, $SO_2$N[($C_1$–$C_6$)-alkyl]$_2$, $NH_2$, N(($C_1$–$C_6$)-alkyl)$_2$, NH($C_1$–$C_7$)-acyl, phenyl, O—($CH_2$)n-phenyl, where n can be =0–6, 1- or 2-naphthyl, 2-, 3- or 4-pyridyl, 2- or 3-furanyl or 2- or 3-thienyl, where the phenyl, naphthyl, pyridyl, furanyl or thienyl rings in each case can be substituted one to 3 times by F, Cl, I, OH, $CF_3$, CN, $OCF_3$, O—($C_1$–$C_6$)-alkyl, ($C_1$–$C_6$)-alkyl, $NH_2$, N(($C_1$–$C_6$)-alkyl)$_2$, COOH, COO—($C_1$–$C_6$)-alkyl, $CONH_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R2 is H, ($C_1$–$C_6$)-alkyl, ($CH_2$)$_n$-phenyl, ($CH_2$)$_n$-thienyl, ($CH_2$)$_n$-pyridyl, C(O)—($CH_2$)$_n$-phenyl, C(O)—($CH_2$)$_n$-thienyl, C(O)—($CH_2$)$_n$-pyridyl, where n can be =0–3 and in which phenyl, thienyl, pyridyl, furyl in each case can be substituted up to two times by Cl, F, CN, $CF_3$, ($C_1$–$C_3$)-alkyl, OH, O—($C_1$–$C_6$)-alkyl; C(O)—($C_1$–$C_6$)-alkyl;

R3 is H, ($C_1$–$C_6$)-alkyl, F, CN, O—($C_1$–$C_6$)-alkyl, ($CH_2$)$_n$-phenyl, ($CH_2$)$_n$-pyridyl, where n can be =0–3 and in which phenyl, pyridyl in each case can be substituted up to two times by Cl, F, CN, $CF_3$, ($C_1$–$C_3$)-alkyl, O—($C_1$–$C_6$)-alkyl; ($C_2$–$C_6$)-alkynyl, C(O)O$CH_3$, C(O)O$CH_2CH_3$, C(O)OH, C(O)$NH_2$, C(O)NH$CH_3$, C(O)N($CH_3$)$_2$, OC(O)$CH_3$;

R4 is ($C_1$–$C_6$)-alkyl, ($C_3$–$C_6$)-cycloalkyl, ($CH_2$)$_n$-phenyl, ($CH_2$)$_n$-pyridyl, where n can be =0–3 and in which phenyl, pyridyl in each case can be substituted up to two times by Cl, F, CN, $CF_3$, ($C_1$–$C_3$)-alkyl, O—($C_1$–$C_6$)-alkyl;

R5 is ($C_1$–$C_6$)-alkyl, ($C_3$–$C_6$)-cycloalkyl, ($CH_2$)$_n$-phenyl, ($CH_2$)$_n$-pyridyl, where n can be =0–3 and in which phenyl, pyridyl in each case can be substituted up to two times by Cl, F, CN, $CF_3$, ($C_1$–$C_3$)-alkyl, O—($C_1$–$C_6$)-alkyl;

or

R4 and R5 together form a —$CH_2$—$CH_2$—, —$CH_2$—C($CH_3$)$_2$— or —$CH_2$—$CH_2$—$CH_2$— group;

R6 is $SO_2$—($C_6H_4$-4-$CH_3$)

or

E)

Y is a direct bond or —$CH_2$—;

X is $CH_2$, $CH(CH_3)$, $CH(C_2H_5)$, $CH(C_3H_7)$;

R1 is H, F, Cl, $CH_3$, $CF_3$, O—($C_1$–$C_3$)-alkyl;

R1 ' is H, F, Cl;

R2 is H;

R3 is H, ($C_1$–$C_3$)-alkyl;

R4 is phenyl, where the phenyl radical can be substituted up to two times by F, Cl, ($C_1$–$C_6$)-alkyl, ($C_3$–$C_6$)-cycloalkyl, O—($C_1$–$C_3$)-alkyl, $CF_3$, O—$CH_2$-phenyl, COOH, COO($C_1$–$C_6$)-alkyl, $CONH_2$;

R5 is phenyl, where the phenyl radical can be substituted up to two times by F, Cl, ($C_1$–$C_6$)-alkyl, ($C_3$–$C_6$)-cycloalkyl, O—($C_1$–$C_3$)-alkyl, $CF_3$, O—$CH_2$-phenyl COOH, COO($C_1$–$C_6$)-alkyl, $CONH_2$;

and their physiologically tolerable salts and physiologically functional derivatives.

Very particularly preferred compounds of the formula I are those in which

Y is a direct bond;

X is $CH_2$

R1 and R1' independently of one another are H, F, Cl, CN, COOH, $CONH_2$, COO($C_1$–$C_3$)-alkyl, ($C_1$–$C_6$)-alkyl, ($C_2$–$C_6$)-alkenyl, ($C_2$–$C_6$)-alkynyl, where in the alkyl, alkenyl and alkynyl radicals one hydrogen can be replaced by OH, OC(O)$CH_3$, O—$CH_2$—Ph, $NH_2$ or N(COOC$H_2$Ph)$_2$;

OC$F_3$, OC$H_2$C$F_3$, O—($C_1$–$C_4$)-alkyl, where in the alkyl radicals one or more, or all hydrogen(s) can be replaced by fluorine, or one hydrogen can be replaced by OH, OC(O)$CH_3$, O—$CH_2$—Ph, $NH_2$ or N(COOC$H_2$Ph)$_2$;

$SO_2$—($C_1$–$C_6$)-alkyl, $SO_2$—($CH_2$)$_n$-phenyl, where n can be =0–3 and the phenyl radical can be substituted by F, Cl, OH, C$F_3$, O—($C_1$–$C_4$)-alkyl;

NH—(CO)—($C_1$–$C_3$)-alkyl; ($CH_2$)$_n$-phenyl, S—($CH_2$)$_n$-phenyl, O—($CH_2$)$_n$-phenyl, where n can be =0–3, 1- or 2-naphthyl, 2-, 3- or 4-pyridyl, 2- or 3-furanyl or 2- or 3-thienyl, where the phenyl, naphthyl, pyridyl, furanyl or thienyl rings in each case can be substituted by F, Cl, C$F_3$, ($C_1$–$C_6$)-alkyl, O—($C_1$–$C_6$)-alkyl and where in the alkyl radicals one hydrogen can be replaced by OH, OC(O)$CH_3$, O—$CH_2$—Ph, $NH_2$ or N(COOC$H_2$Ph)$_2$;

1,2,3-triazol-5-yl, where the triazole ring can be substituted in the 1-, 2- or 3-position by methyl or benzyl;

tetrazol-5-yl, where the tetrazole ring can be substituted in the 1- or 2-position by methyl or benzyl;

R2 is H, ($C_1$–$C_4$)-alkyl, ($C_5$–$C_6$)-cycloalkyl; ($CH_2$)$_n$-phenyl, where n can be =0-3, C(O)—($C_1$–$C_4$)-alkyl or C(O)-phenyl;

R3 is F, ($C_4$–$C_6$)-alkyl, $CH_2$-phenyl, where phenyl can be substituted up to two times by F, Cl, C$F_3$, O—($C_1$–$C_3$)-alkyl, ($C_1$–$C_3$)-alkyl, COOH, CO—O—($C_1$–$C_3$)-alkyl or CON$H_2$;

R4 is ($C_1$–$C_6$)-alkyl, ($C_3$–$C_6$)-cycloalkyl, ($CH_2$)$_n$-phenyl, where n can be =0–3 and the phenyl radical can be substituted up to two times by F, Cl, O—($C_1$–$C_4$)-alkyl or OH;

R5 is ($C_1$–$C_6$)-alkyl, ($C_3$–$C_6$)-cycloalkyl, ($CH_2$)$_n$-phenyl, where n can be =0–3 and the phenyl radical can be substituted up to two times by F, Cl, O—($C_1$–$C_4$)-alkyl or OH;

and their physiologically tolerable salts.

The invention relates to compounds of the formula I, in the form of their racemes, raceme mixtures and pure enantiomers, and to their diastereomers and mixtures thereof.

On account of their higher water solubility, compared with the starting or base compounds, pharmaceutically tolerable salts are particularly suitable for medicinal applications. These salts must have a pharmaceutically tolerable anion or cation. Suitable pharmaceutically tolerable acid addition salts of the compounds according to the invention are salts of inorganic acids, such as hydrochloric acid, hydrobromic, phosphoric, metaphosphoric, nitric, sulfonic and sulfuric acids, and of organic acids, such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. For medicinal purposes, the chlorine salt is particularly preferably used. Suitable pharmaceutically tolerable basic salts are ammonium salts, alkali metal salts (such as sodium and potassium salts) and alkaline-earth metal salts (such as magnesium and calcium salts).

Salts with a pharmaceutically intolerable anion are likewise included in the scope of the invention as useful intermediates for the preparation or purification of pharmaceutically tolerable salts and/or for use in nontherapeutic applications, for example in-vitro applications.

The term "physiologically functional derivative" used here designates any physiologically tolerable derivative of a compound according to the invention, e.g. an ester, which on administration to a mammal, such as, for example, man, is able (directly or indirectly) to form such a compound or an active metabolite thereof.

Prodrugs of the compounds according to the invention are a further aspect of this invention. Such prodrugs can be metabolized in vivo to give a compound according to the invention. These prodrugs can themselves be active or inactive.

The compounds according to the invention can also be present in various polymorphic forms, e.g. as amorphous and crystalline polymorphic forms. All polymorphic forms of the compounds according to the invention are included in the scope of the invention and are a further aspect of the invention.

Below, all references to "compound(s) according to formula (I)" refer to compound(s) of the formula (I) as described above, and their salts, solvates and physiologically functional derivatives as described herein.

The amount of a compound according to formula (I) which is necessary in order to achieve the desired biological effect is dependent on a number of factors, e.g. the specific compound selected, the intended use, the manner of administration and the clinical condition of the patient. In general, the daily dose is in the range from 0.3 mg to 100 mg (typically from 3 mg to 50 mg) per day per kilogram of body weight, e.g. 3–10 mg/kg/day. An intravenous dose can be, for example, in the range from 0.3 mg to 1.0 mg/kg, which can be suitably administered as an infusion of 10 ng to 100 ng per kilogram per minute. Suitable infusion solutions for these purposes can contain, for example, from 0.1 ng to 10 mg, typically from 1 ng to 10 mg per milliliter. Individual doses can contain, for example, from 1 mg to 10 g of the active compound. Thus, ampoules for injections can contain, for example, from 1 mg to 100 mg, and orally administrable individual dose formulations, such as, for example, tablets or capsules, can contain, for example, from 1.0 to 1000 mg, typically from 10 to 600 mg. In the case of pharmaceutically tolerable salts, the abovementioned weight details relate to the weight of the thiazolidin-2-ylidene ion derived from the salt.

For the prophylaxis or therapy of the abovementioned conditions, the compounds according to formula (I) can be used as the compound itself, but they are preferably present in the form of a pharmaceutical composition with a tolerable vehicle. The vehicle must of course be tolerable, in the sense that it is compatible with the other constituents of the composition and is not harmful to the patient's health. The vehicle can be a solid or a liquid or both and is preferably formulated with the compound as an individual dose, for example as tablets which can contain from 0.05% to 95% by weight of the active compound. Further pharmaceutically active substances can also be present, including further compounds according to formula (I). The pharmaceutical compositions according to the invention can be prepared by one of the known pharmaceutical methods, which essentially consist in mixing the constituents with pharmacologically tolerable excipients and/or auxiliaries.

Pharmaceutical compositions according to the invention are those which are suitable for oral, rectal, topical, oral (e.g. sublingual) and parenteral (e.g. subcutaneous, intramuscular, intradermal or intravenous) administration, although the most suitable manner of administration in each individual case is dependent on the nature and severity of the condition to be treated and on the nature of the compound according to formula (I) used in each case. Sugar-coated formulations and sugar-coated delayed release formulations are also included in the scope of the invention. Acid-resistant and enteric formulations are preferred. Suitable enteric coatings include cellulose acetate phthalate, polyvinyl acetate phthalate, hydroxypropyl-methylcellulose phthalate and anionic polymers of methacrylic acid and methyl methacrylate.

Suitable pharmaceutical compounds for oral administration can be present in separate units, such as, for example, capsules, cachets, lozenges or tablets which in each case contain a certain amount of the compound according to formula (I); as powders or granules; as a solution or suspension in an aqueous or nonaqueous liquid; or as an oil-in-water or water-in-oil emulsion. As already mentioned, these compositions can be prepared by any suitable pharmaceutical method which includes a step in which the active compound and the vehicle (which can consist of one or more additional constituents) are brought into contact. In general, the compositions are prepared by uniform and homogeneous mixing of the active compound with a liquid and/or finely divided solid vehicle, after which the product, if necessary, is shaped. Thus a tablet, for example, can be prepared by pressing or shaping a powder or granules of the compound, if appropriate with one or more additional constituents. Pressed tablets can be prepared in free-flowing form, such as, for example, a powder or granules, by tableting the compound, if appropriate mixed with a binder, lubricant, inert diluent and/or one (a number of) surface-active/dispersing agents in a suitable machine. Shaped tablets can be prepared by shaping the pulverulent compound moistened with an inert liquid diluent in a suitable machine.

Pharmaceutical compositions which are suitable for oral (sublingual) administration include lozenges which contain a compound according to formula (I) with a flavoring, customarily sucrose and gum arabic or tragacanth, and pastilles which include the compound in an inert base such as gelatin and glycerol or sucrose and gum arabic.

Suitable pharmaceutical compositions for parenteral administration preferably include sterile aqueous preparations of a compound according to formula (I), which are preferably isotonic with the blood of the intended recipient. These preparations are preferably administered intravenously, although the administration can also take place subcutaneously, intramuscularly or intradermally as an injection. These preparations can preferably be prepared by mixing the compound with water and rendering the obtained solution sterile and isotonic with the blood. Injectable compositions according to the invention in general contain from 0.1 to 5% by weight of the active compound.

Suitable pharmaceutical compositions for rectal administration are preferably present as individual dose suppositories. These can be prepared by mixing a compound according to formula (I) with one or more conventional solid vehicles, for example cocoa butter, and shaping the resulting mixture.

Suitable pharmaceutical compositions for topical application to the skin are preferably present as an ointment, cream, lotion, paste, spray, aerosol or oil. Vehicles which can be used are petroleum jelly, lanolin, polyethylene glycols, alcohols and combinations of two or more of these substances. The active compound is in general present in a concentration of 0.1 to 15% by weight of the composition, for example of 0.5 to 2%.

Transdermal administration is also possible. Suitable pharmaceutical compositions for transdermal administration can be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is about 1% to 35%, preferably about 3% to 15%. As a particular possibility, the active compound can be released by electrotransport or iontophoresis, as described, for example, in Pharmaceutical Research, 2(6): 318 (1986), which is incorporated by reference herein in its entirety.

The invention furthermore relates to a process for the preparation of the compounds of the formula I (R2=H), which comprises A) reacting compounds of the formula II

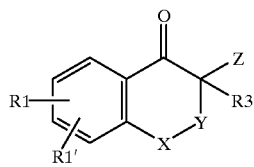

Formula II in which R1, R1', R3 and X and Y have the meaning indicated, and Z is the radical of an activated ester of an inorganic or organic acid, with thioureas of the formula III, which can be present in the tautomeric forms IIIa and IIIb and IIIc

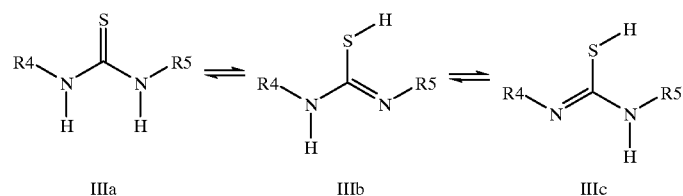

in which R4 and R5 have the meaning indicated, and

B) if appropriate converting the compounds of the formula I (R2=H) into their acid addition salts using organic or inorganic acids or converting salts of the compounds of the formula I obtained (R2=H) into the free basic compounds of the formula I (R2=H) using organic or inorganic bases.

Suitable inorganic acids are, for example:
hydrohalic acids such as hydrochloric acid and hydrobromic acid, and also sulfuric acid, phosphoric acid and amidosulfonic acid.

Organic acids which may be mentioned are, for example:
formic acid, acetic acid, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, or 1,2-benzisothiazol-3(2H)-one, 6-methyl-1,2,3-oxathiazin4(3H)-one-2,2-dioxide.

The compounds of the formula I (R2=H) can also be present in their tautomeric forms:

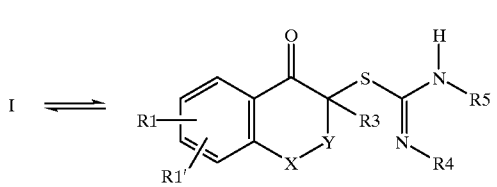

Ia

The compounds of the formula I according to the invention (R2=H) can moreover be present in their possible geometric isomeric structures.

The alkyl, alkenyl and alkynyl radicals in the substituents R1, R1', R2, R3, R4 and R5 can be either straight-chain or branched.

Via the open-chain tautomeric form Ia, the cyclic compounds of the formula I (R2=H) in which R4 and R5 are different are in equilibrium with the positional isomer compounds of the formula Ib (R2=H) and their acid addition salts

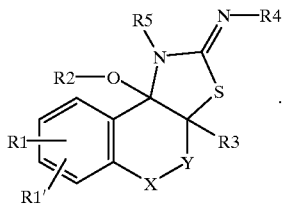

Formula Ib

Which of the two cyclic isomers I (R2=H) or Ib (R2=H) or their acid addition salts are preferably present depends to a particular extent on the different space filling of the substituents R4 and R5 in such a way that the spatially smaller substituent is preferably located in position 3 of the thiazolidine ring system.

In the compounds according to the invention, only one of the possible isomeric or tautomeric forms of a particular substance is indicated below.

The procedure described above is advantageously carried out such that the compounds II are reacted with the thioureas III in the molar ratio from 1:1 to 1:1.5. The reaction is advantageously carried out in an inert solvent, e.g. in polar organic solvents such as dimethyl sulfoxide, dimethylformamide, dimethylacetamide, N-methyl-2-pyrrolidone, dioxane, tetrahydrofuran, acetonitrile, nitromethane or diethylene glycol dimethyl ether. Particularly advantageous solvents, however, prove to be methyl acetate and ethyl acetate, short-chain alcohols such as methanol, ethanol, propanol, isopropanol, and lower dialkyl ketones, such as, for example, acetone, butan-2-one or hexan-2-one. Mixtures of the reaction media mentioned can also be used; and mixtures of the solvents mentioned can also be used with solvents which taken per se are less suitable, such as, for example, mixtures of methanol with benzene, ethanol with toluene, methanol with diethyl ether or with tert-butyl methyl ether, ethanol with tetrachloromethane, acetone with chloroform, dichloromethane or 1,2-dichloroethane, where the more polar solvent in each case should expediently be used in an excess. The reaction components can be suspended or dissolved in the respective reaction medium. Fundamentally, the reaction components can also be reacted without solvent, in particular if the respective thiourea has a melting point which is as low as possible. The reaction proceeds in an only slightly exothermic manner and can be carried out between −10° C. and 150° C., preferably between 0° C. and 50° C. A temperature range between 20° C. and 40° C. as a rule proves to be particularly favorable.

The reaction time is largely dependent on the reaction temperature and is between 2 minutes and 3 days at relatively high and relatively low temperatures respectively. In the favorable temperature range, the reaction time is in general between 5 minutes and 48 hours.

Frequently, the compounds I (R2=H) separate in the form of their poorly soluble acid addition salts in the course of the reaction, expediently a suitable precipitating agent is additionally subsequently added. Those used are, for example, hydrocarbons such as benzene, toluene, cyclohexane or heptane or tetrachloromethane; in particular, alkyl acetates such as ethyl acetate or n-butyl acetate or dialkyl ethers such as diethyl ether, diisopropyl ether, di-n-butyl ether or tert-butyl methyl ether prove particularly suitable. If the reaction mixture remains in solution after the end of the reaction, the salts of the compounds I (R2=H), can be precipitated using one of the precipitating agents mentioned, if appropriate after concentration of the reaction solution. Furthermore, the solution of the reaction mixture can also be advantageously filtered into the solution of one of the precipitating agents mentioned with stirring. Since the reaction of the compounds II with the thioureas III proceeds virtually quantitatively, the crude products obtained are usually already analytically pure. The working-up of the reaction mixture can also be carried out such that the reaction mixture is rendered alkaline with addition of an organic base, such as, for example, triethylamine or diisobutylamine, or ammonia or morpholine or piperidine or 1,8-diazabicyclo[5.4.0]undec-7-ene, and the crude reaction product is purified chromatographically, e.g. on a silica gel column, after concentration. Suitable elution media for this prove to be, for example, mixtures of ethyl acetate with methanol, mixtures of dichloromethane with methanol, mixtures of toluene with methanol or ethyl acetate or mixtures of ethyl acetate with hydrocarbons such as heptane. If the purification of the crude product is carried out in the manner last described, an acid addition product of the formula I (R2=H) can be obtained from the pure base of the formula I (R2=H) thus obtained by dissolving or suspending the base in an organic protic solvent such as methanol, ethanol, propanol or isopropanol or in an organic aprotic solvent such as ethyl acetate, diethyl ether, diisopropyl ether, tert-butyl methyl ether, dioxane, tetrahydrofuran, acetone or butan-2-one and then treating this mixture with an at least equimolar amount of an inorganic acid such as, for example, hydrochloric acid, dissolved in an inert solvent such as, for example, diethyl ether or ethanol, or another of the inorganic or organic acids mentioned further above. The compounds of the formula I (R2=H) can be recrystallized from an inert, suitable solvent such as, for example, acetone, butan-2-one, acetonitrile, nitromethane. Particularly advantageous, however, is reprecipitation from a solvent such as, for example, dimethylformamide, dimethylacetamide, nitromethane, acetonitrile, preferably methanol or ethanol.

Compounds of the formula I or Ib where R2=($C_1$–$C_6$)-alkyl, ($C_3$–$C_6$)-cycloalkyl or ($CH_2$)$_n$-aryl, where n can be =0–5 and aryl is determined as further above, can be obtained by either aa) allowing the acid addition salts of the formula I or Ib where R2=H to react in a solvent of the formula R2—OH, where R2 has the meaning described above, at a temperature of −20° C. to 120° C., preferably at −5° C. to 50° C., for 2 hours to 4 day preferably 4 hours to 2 days, or ab) reacting the free bases of the formula I or Ib where R2=H in a solvent of the formula R2—OH, where R2 has the meaning described above, with equimolar, substoichiometric or catalytic, preferably catalytic, amounts of an inorganic or organic acid, such as are described further above, or with addition of an acidic ion exchanger at a temperature of −20° C. to 120° C., preferably at −5° C. to 50° C., for 2 hours to 4 days, preferably 4 hours to 2 days, or ac) carrying out the reactions according to aa) and ab) in an inert aprotic solvent such as dichloromethane, chloroform, 1,2-dichloroethane, heptane, benzene, toluene, acetonitrile, nitromethane, dioxane, tetrahydrofuran, ethylene glycol dimethyl ether, diethyl ether, diisopropyl ether, tert-butyl methyl ether, acetone, butan-2-one or lower alkyl acetates, such as, for example, ethyl acetate, by addition of 1 to 5, preferably 1.5–2, equivalents of a compound of the formula R2-OH or ad) converting compounds of the formula I or Ib where R2=H into their alcoholate in a polar aprotic solvent, such as, for example, tetrahydrofuran, dioxane, ethylene glycol dimethyl ether, nitromethane, acetonitrile or dimethylformamide, dimethylacetamide or N-methyl-2-pyrrolidone, with the aid of a base, such as, for example, sodium hydride, lithium diisopropylamide, KOH or potassium carbonate and then allowing this to react with addition of an alkylating agent of the formula R2—X, where X=chlorine, bromine, iodine, O—C(O)—CH$_3$, O—C(O)—CF$_3$, O—C(O)—C$_6$H$_4$-4-NO$_2$, O—SO$_2$—CH$_3$, O—SO$_2$—CF$_3$, O—SO$_2$—C$_6$H$_4$-4-CH$_3$, O—SO$_2$-C$_6$H$_4$-4-NO$_2$, at −20 to 150° C., preferably at −15 to 50° C., for 10 minutes to 2 days, preferably for 20 minutes to 12 hours.

The compounds of the formula I or Ib where R≠H, which are obtained according to aa) to ad) as described above, are either precipitated as a poorly soluble acid addition salt—they are then filtered off with suction, washed with a little of the solvent employed and dried—or they remain in solution. Purification can be carried out by neutralizing the reaction mixture, after formation of the ethers of the formula I or Ib where R≠H has taken place, with an inorganic or organic base, e.g. with triethylamine, and concentrating the resulting mixture and then chromatographing it on silica gel. The pure base of the formula I or Ib where R2≠H thus obtained can be converted into an acid addition salt, as described above for compounds of the formula I or Ib where R2=H.

Compounds of the formula I or Ib where R2=C(O)—(C$_1$–C$_6$)-alkyl, C(O)—(C$_3$–C$_6$)-cycloalkyl or C(O)—(CH$_2$)$_n$-aryl, where aryl can be phenyl, thienyl, pyridyl or furyl and n is as defined further above, can be obtained by either ba) proceeding as described under aa)–ac), with the difference that instead of a compound R2—OH a compound R2—COOH is employed where R2 is (C$_1$–C$_6$)-alkyl, (C$_3$–C$_6$)-cycloalkyl or (CH$_2$)$_n$-aryl and n and aryl have the meanings described further above, and employing 1 to 2 equivalents of the compound R2—COOH, preferably 1.5 equivalents of the compound R2—COOH, and dispensing with the addition of the acidic inorganic or organic catalyst described under aa)–ac), but advantageously employing the acidic cation exchanger or bb) reacting a compound of the formula I or Ib where R2=H (free base) with a compound of the formula R2—COOH, where R2=C(O)—(C$_1$–C$_6$)-alkyl, C(O)—(C$_3$–C$_6$)-cycloalkyl or C(O)—(CH$_2$)$_n$-aryl and aryl and n are as defined further above, e.g. in the sense of a Mitsunobu reaction (O. Mitsunobu, Synthesis 1981, incorporated herein by reference, to give a compound of the formula I or Ib where R2 is not H or bc) reacting a compound of the formula R2—C(O)—Cl or R2—C(O)—Br or R2—C(O)—O—(O)—C—R2 with a compound of the formula I or Ib where R2=H in the sense of an esterification of an alcohol (See Houben-Weyl, Methoden der Organischen Chemie [Methods of Organic Chemistry], Georg Thieme Verlag Stuttgart, Volume E5, pp. 656–715, incorporated herein by reference).

The compounds of the formula I or Ib where R2≠H, which are obtained according to ba) to bc) as described above, either precipitate as a poorly soluble acid addition salt—they are then filtered off with suction, washed with a little of the solvent employed and dried—or they remain in solution. Purification can be carried out by neutralizing the reaction mixture, after formation of the esters of the formula I or Ib where R2 is not H has taken place, with an inorganic or organic base, e.g. with potassium carbonate or triethylamine, and concentrating the resulting mixture and then chromatographing it on silica gel. The pure base of the formula I or Ib where R2 is not H obtained can be converted into an acid addition salt, as described above for compounds of the formula I or Ib where R2=H.

For the most part, the starting substances of the formula III are described in the literature (cf. Houben-Weyl, Methoden der organischen Chemie [Methods of Organic Chemistry], Vol. 9, p. 384; 4th Ed.; 1955 or DOS 2640358 Mar. 3, 1978) each incorporated herein by reference).

In the compounds of the formula II, possible radicals of an activated ester Z are, for example: Cl, Br, I, O—C(O)—C$_6$H$_4$-4-NO$_2$, O—SO$_2$—CH$_3$, O—SO$_2$—CF$_3$, O—SO$_2$—C$_6$H$_4$-4-CH$_3$, O—SO$_2$—C$_6$H$_4$. They can be obtained by a number of methods:

ca) Diazoketones of the formula VIII

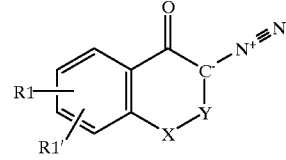

Formula VIII can be converted with hydrohalic acids into the compounds of the formula II (Z=Cl, Br, I; R3=H). This process and some compounds of the formula II are known from the literature (e.g. J. Am. Chem. Soc 80, 2255 (1958); J. Indian Chem. Soc. 42, 115 (1965), incorporated herein by reference), and the further compounds of the formula II can be prepared and reacted correspondingly. The diazoketones of the formula VIII can furthermore be converted into the corresponding compounds of the formula II (R3=H) by processes known from the literature via the hydroxy compounds of the formula IX

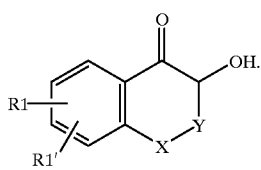

Formula IX cb) Since the processes mentioned under ca) only lead to compounds of the formula II in which R3 remains restricted to hydrogen, compounds of the formula II are advantageously prepared by reacting compounds of the formula X

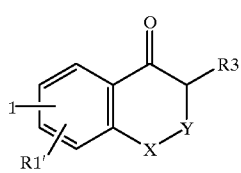

Formula X with a suitable halogenating agent, such as, for example, with elemental chlorine or bromine, sulfuryl chloride, monochlorourea, N-chlorosuccinimide, copper(II) bromide, bromine-dioxane complex, N-bromosuccinimide, under conditions known from the literature. The easily accessible compounds of the formula X are either known or can be prepared by processes known from the literature.

Suitable halogenating agents are, for example, elemental chlorine, sulfuryl chloride, monochlorourea, N-chlorosuccinimide, bromine-dioxane complex, N-bromosuccinimide, but in particular elemental bromine or copper(II) bromide. In the case of halogenation with bromine, bromine is advantageously added dropwise, if appropriate diluted in inert solvents, to a solution or suspension of the equimolar amount of the compound of the formula X in an inert solvent. Those suitable are, for example, halohydrocarbons such as di- or trichloromethane or 1,2-dichloroethane, but preferably glacial acetic acid or lower alkyl acetate, or mixtures of the solvents mentioned. The reaction temperature is between 0° and 50° C., preferably between 10° and 35° C. Halogenations of ketones are catalyzed by acids; it is therefore advantageous if the reaction mixture is treated with catalytic amounts of an acid, e.g. with hydrobromic acid, or, after dropwise addition of a little bromine, the reaction mixture is first warmed until the halogen is decolorized and then brominated further.

In the bromination of the compounds of the formula X with copper(II) bromide, it is possible to carry out the reaction analogously to the methods described in J. Org. Chem. 29, 3459 (1964) or J. Org. Chem. 40, 1990 (1975), each incorporated herein by reference.

Suitable chlorinating agents are, in particular, sulfuryl chloride, which is reacted in the customary manner with a solution or suspension of the compound of the formula X in a solvent, such as, for example, tri- or tetrachloroethane or an ether such as diethyl ether or tert-butyl methyl ether, in a temperature range between 20° and 80° C. The mixture is then treated with ice water and worked up in the customary manner. When using chlorine as a halogenating agent, HCl gas is first introduced as a catalyst, then, in a temperature range from 0° to 25° C., an equivalent amount of chlorine is introduced into the solution of a compound of the formula X in a polar solvent, e.g. glacial acetic acid or dimethylformamide or N-methyl-2-pyrrolidone. The reaction time is 2–24 hours. The mixture is then treated with ice water and worked up in the customary manner. If N-chlorosuccinimide is employed as a chlorinating agent in the chlorination reaction, the compounds of the formula X are advantageously reacted with 1–2 equivalents of N-chlorosuccinimide at about 50° C. for 2–12 hours in a polar solvent, such as, for example, glacial acetic acid, after addition of a catalytic amount of hydrochloric acid. The mixture is then treated with ice water and worked up in the customary manner.

cc) The compounds of the formula II can additionally be obtained by preparing the α-hydroxyketones of the formula XI

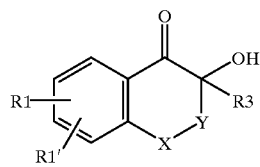

Formula XI which are either known (Chem. Ber. 83, 390, incorporated by reference herein) or can be prepared according to customary processes, in a manner known per se with the activated derivatives of organic and inorganic acids such as methanesulfonyl chloride, trifluoromethanesulfonyl chloride, ethanesulfonyl chloride, benzenesulfonyl chloride, p-toluenesulfonyl chloride, thionyl bromide, phosphorus trichloride, phosphorus tribromide, phosphorus oxychloride, p-nitrobenzoyl chloride.

The solution or suspension of the compounds of the formula II thus obtained according to the respective method is expediently concentrated under reduced pressure and the compounds of the formula II are purified by crystallization in inert solvents such as, for example, benzene, toluene, tetrachloromethane, dichloromethane, 1,2-dichloroethane, cyclohexane, hexane, heptane. Another method of purification consists in chromatographing the reaction mixtures on a silica gel column, heptane, diethyl ether, tert-butyl methyl ether, toluene, ethyl acetate or mixtures thereof expediently being used as eluents.

The compounds of the formula II obtained can also be employed in the next stage without a further purification operation.

Compounds of the formula X

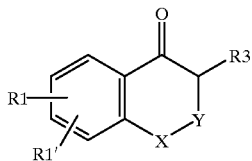

Formula X in which R3 is not hydrogen, are accessible in a different manner:

da) Compounds of the formula X in which R3=fluorine can be prepared, for example, by reacting compounds of the formula X in which R3=H with an electrophilic fluorinating reagent. Suitable electrophilic fluorinating reagents (see also: W. E. Barnette, J. Am. Chem. Soc. 106, 452–454 (1984), incorporated herein by reference) are, for example, 1-fluoro-2,4,6-trimethylpyridinium triflate, 3,5-dichloro-1-fluoropyridinium triflate, 1-fluoropyridinium triflate, 1-fluoropyridinium tetrafluoroborate, 1-fluoropyridinium pyridine heptafluorodiborate, N-fluoro-N-methyl-p-toluenesulfonamide, N-fluoro-N-propyl-p-toluenesulfonamide, N-fluorobenzene-sulfonamide, N-fluorobenzene-sulfonimide [NFSi], 1-fluoro-4-hydroxy-1,4-diazoniabicyclo[2.2.2]octane bis (tetra-fluoroborate) (NFTh). The fluorination reaction is carried out, for example such that a base, with the aid of which a compound of the formula X (R3=H) is converted into the enolate of the compound of the formula X (R3=H), is added to a solution or suspension of a compound of the formula X in which R3=H in equivalent amounts in a nonpolar aprotic solvent such as benzene, toluene, hexane or heptane or in a polar aprotic solvent such as tetrahydrofuran, dimethylformamide, acetonitrile, diethyl ether or tert-butyl methyl ether or in mixtures thereof. Suitable bases for this reaction are n-butyllithium, potassium or sodium hexamethyldisilazane, sodium hydride, potassium hydride, potassium tert-butoxide, methyllithium, tetra-n-butylammonium hydroxide. A suitable reaction temperature is −78° to 25° C. For the dissolution or suspension of the enolate of the compound of the formula X (R3=H) thus formed, 1 to 2, preferably 1.5, equivalents of one of the abovementioned fluorinating reagents, dissolved in one of the abovementioned solvents or solvent mixtures, preferably dissolved in toluene or dichloromethane, are then added dropwise at a temperature of −78° to +100° C., preferably at a temperature of −50° to +80° C. The sequence of the addition of the reaction components can also be carried out in the reverse order, i.e. by adding the solution or suspension of the enolate of the compound of the formula X (R3=H) dropwise to a solution of the fluorinating reagent at the temperatures indicated. Depending on the reaction temperature selected, the reaction is complete after 15 minutes to 48 hours.

The reaction, particularly with N-fluorobenzenesulfonimide, can advantageously also be carried out in analogy to E. Differding and H. Ofner, Synlett 187–189 (1991), incorporated herein by reference, in such a way that the trimethylsilyl enol ether of the compound of the formula X, in which R3=H, is first prepared (e.g. with trimethylsilyl bromide or trimethylsilyl trifluoromethanesulfonate in toluene at −78 to 80° C. with addition of an equivalent of a base such as, for example, triethylamine) and the fluorinating reagent, dissolved in dichloromethane or toluene, is then added at room temperature and the reaction mixture is worked up after a reaction time of about 12 hours (room temperature). The working-up of the reaction mixture can be carried out in such a way that, after neutralization of an excess of the base employed, the reaction mixture is concentrated and then treated with a solvent such as, for example, ethyl acetate or heptane and extracted by shaking with half-concentrated sodium hydrogencarbonate solution. The organic phase is concentrated after drying over magnesium sulfate and the reaction product can then be recrystallized either from a solvent such as hexane or heptane for further purification, or else alternatively subjected to a chromatographic purification on a silica gel column with elution with, for example, mixtures of dichloromethane with heptane or ethyl acetate with heptane.

The reaction with 1-fluoro-4-hydroxy-1,4-diazoniabicyclo]2.2.2]octane bis(tetra-fluoroborate) (NFTh) can also be carried out in such a way that the ketone is used as such, without conversion into an enolate or an enol silyl ether.

db) Compounds of the formula X in which R3=($C_1$–$C_6$)-alkyl or $(CH_2)_n$-aryl, and where n can be =1–5 and aryl is as defined further above, can be prepared, for example, by reacting compounds of the formula X, in which R3=H, with a strong base and with an alkylating reagent of the formula R3=X, where X can be Br, I, O—C(O)—$C_6H_4$-4-$NO_2$, O—$SO_2$—$CH_3$, O—$SO_2$—$CF_3$, O—$SO_2$—$C_6H_4$-4-$CH_3$O—$SO_2$—$C_6H_4$. In order to ensure that in this alkylation only the desired monoalkylation takes place, the compounds of the formula X (R3=H) are previously advantageously converted into compounds, for example, of the formula XII, XIII or XIV.

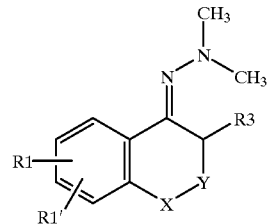

Formula XII

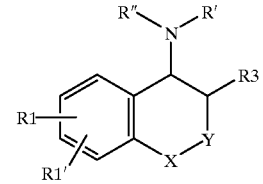

Formula XIII

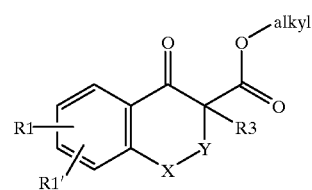

Formula XIV

Compounds of the type of formula XII (R3=H) can be prepared according to F. Henin et al., Tetrahedron, 50, 2849–2864 (1994), incorporated herein by reference. Those of the type of formula XIII (R3=H), where R'-R" can be —$(CH_2)_4$—, —$(CH_2)_5$—, —$CH_2$—$CH_2$—O—$CH_2$—$CH_2$—, can be prepared, for example, according to Stork et al., J. Am. Chem. Soc. 85, 207 (1963), incorporated herein by reference. Compounds of the formula XIV (R3=H) are accessible by methods known from the literature, e.g. P. W. Hickmott, Chem. Ind. (London), 731 (1974), incorporated herein by reference. Compounds of the type of formulae XII and XIV (R3=H) can then be reacted, after conversion into their anion by means of a strong base, with an alkylating agent of the formula R3-X, where R3 and X are defined as described further above, to give the desired compounds of the formulae XII and XIV (R3=H) and, after acidic hydrolysis of the hydrazone (XII) or hydrolysis and decarboxylation of the β-ketoesters (XIV), converted into the compounds of the formula X according to the invention, in which R3=H. Compounds of the formula XIII (R3=H) can be converted in an inert solvent such as trichloromethane or toluene, after addition of a base such as triethylamine, into compounds of the formula X in which R3=H with the aid of an alkylating agent of the formula R3-X after acidic hydrolysis of the α-alkylated enamine of the formula XIII (R3=H).

Compounds of the formula X in which R3=COOCH$_3$, COOCH$_2$CH$_3$, COOH, CONH$_2$, CONHCH$_3$, CON(CH$_3$)$_2$, can be prepared via compounds of the formula XII and of the formula XIII according to methods known from the literature by conversion with, for example, Cl—C(O)—O—CH$_2$—CH$_3$.

dd) Compounds of the formula X in which R3=CN can be prepared by methods known from the literature (M. E. Kuehne, J. Org. Chem. 81, 5400–5404 (1959), incorporated herein by reference), by reaction of a compound of the formula XIII with cyanogen chloride.

de) Compounds of the formula X in which R3=O—(C$_1$–C$_6$)-alkyl can be prepared by methods known from the literature (J. Chan Lee et al., Synth. Commun. 27, 4085–90 (1997), incorporated herein by reference) starting from compounds of the formula X where R3=H by refluxing a compound of the formula X (R3=H) with [hydroxy(p-nitrobenzenesulfonyloxy)iodo]benzene [HNIB] in acetonitrile for 2–6 hours and then reacting the resulting intermediate after removal of the solvent directly with an alcohol of the formula R3—OH where R3 has the meaning defined above, at elevated temperature.

df) Compounds of the formula X in which R3=O(O)CCH$_3$ can also be prepared analogously. In this case, the intermediate described in de) is converted into a compound of the formula X in which R3=O(O)CCH$_3$ in acetic acid with addition of catalytic amounts of silver carbonate.

dg) Compounds of the formula X in which R3=N$_3$ can either be prepared from the corresponding compounds of the formula X in which R3=Cl or Br by nucleophilic replacement with azide (K. Van Sant, M. S. South; Tetrahedron Lett. 28, 6019 (1987), incorporated herein by reference) or else better in analogy to T. Patonay and R. V. Hoffman, J. Org. Chem. 59, 2902–2905 (1994), incorporated herein by reference, from enol acetates of the compounds X (R3=H) or from enamines of the compounds X (compounds of the formula XIII (R3=H)) via an α-tosyloxyketone and subsequent reaction with sodium azide.

dh) Compounds of the formula X in which R3=(C$_2$–C$_6$)-alkynyl can be prepared via 1,3-dicarbonyl compounds of the formula XIV. In analogy to a method known from the literature (M. Ochiai, T. Ito, Y. Takaoka, Y. Masaki, M. Kunishima, S. Tani, Y. Nagao; J. Chem. Soc., Chem. Commun. 118–119 (1990), incorporated herein by reference), for this, compounds of the formula XIV (R3=H) can first be converted into their enolate anion using a strong base such as potassium tert-butoxide in tert-butanol or such as potassium tert-butoxide in tetrahydrofuran or such as sodium hydride in tetrahydrofuran and then reacted with ethynyl(phenyl)iodonium tetrafluoroborate with formation of compounds of the formula XIV in which R3=(C$_2$–C$_6$)-alkynyl.

di) Compounds of the formula X in which R3=SO$_2$—(C$_1$–C$_6$)-alkyl, SO$_2$—(CH$_2$)$_n$-phenyl, SO—(C$_1$–C$_6$)-alkyl, SO—(CH$_2$)$_n$-phenyl, S—(C$_1$–C$_6$)-alkyl, S—(CH$_2$)$_n$-phenyl, where n can be =0–3, can be prepared by reacting the enolate anion of the compounds of the formula X, in which R3=H, generated by means of a strong base such as lithium diisopropylamide in a solvent mixture such as hexane/pyridine according to methods known from the literature, with the appropriate dialkyl, di(aralkyl) or diphenyl disulfide at low temperatures. The compounds of the formula X obtained in this manner, in which R3=S—(C$_1$–C$_6$)-alkyl or S—(CH$_2$)$_n$-phenyl where n=0–3, can be processed further with perselenic acid to give the corresponding sulfoxides (R3=SO—(C$_1$–C$_6$)-alkyl, SO—(CH$_2$)$_n$-phenyl) (J. Drabowicz, M. Mikolajczyk; Synthesis 1978, 758, incorporated herein by reference) and with a solution of 30% strength hydrogen peroxide or by reaction with m-chloroperoxybenzoic acid in dichloromethane to give the corresponding sulfones (R3=SO$_2$—(C$_1$–C$_6$)-alkyl, SO$_2$—(CH$_2$)$_n$-phenyl).

Compounds of the formula X (R3=H), which serve as starting materials for the preparation of compounds of the formula II in which R3=H, F, CN, N$_3$, O—(C$_1$–C$_6$)-alkyl, (C$_1$–C$_6$)-alkyl, (CH$_2$)$_n$-aryl, where n can be =0–5 and aryl can be phenyl, thienyl, pyridyl or furyl, (C$_2$–C$_6$)-alkynyl, SO$_2$—(C$_1$–C$_6$)-alkyl, SO$_2$—(CH$_2$)$_n$-phenyl, SO—(C$_1$–C$_6$)-alkyl, SO—(CH$_2$)$_n$-phenyl, S—(C$_1$–C$_6$)-alkyl, S—(CH$_2$)n-phenyl, where n can be =0–3, C(O)OCH$_3$, C(O)OCH$_2$CH$_3$, C(O)OH, C(O) NH$_2$, C(O)NHCH$_3$, C(O)N(CH$_3$)$_2$, O(O)CCH$_3$, and Z has the meanings mentioned further above, are commercially available or accessible in a different manner in analogy to processes known from the literature (Scheme 1):

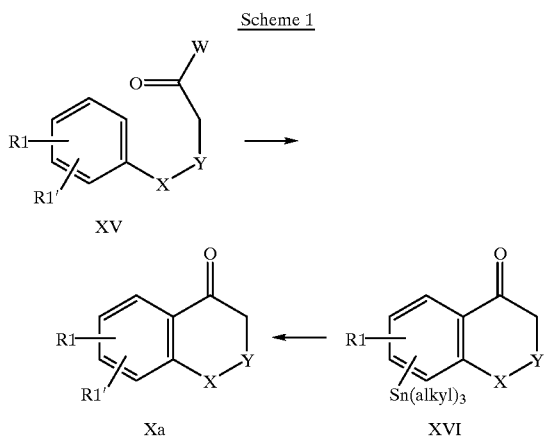

ea) Compounds of the formula XV in which R1, R1', X and Y have the meanings mentioned at the outset, and in which W is a carbonyl-activating group such as halogen, e.g. Cl or Br or O—R" or O—C(O)—R", where R"=alkyl, e.g. CH$_3$, or aryl, e.g. phenyl, can be subjected to ring closure with protonic acids or Lewis acids to give the corresponding cyclized compounds of the formula Xa according to methods known from the literature, e.g. Houben-Weyl, Methoden der Organischen Chemie [Methods of Organic Chemistry], Thieme Verlag Stuttgart, 1973, Volume VII/2a, p. 111 ff.

eb) Compounds of the formulae X and Xa, in which R1 and/or R1'=S—(C$_1$–C$_6$)-alkyl, S—phenyl, SO—(C$_1$–C$_6$)-alkyl, SO—phenyl, SO$_2$—(C$_1$–C$_6$)-alkyl, SO$_2$-phenyl, S—(CH$_2$)$_n$-phenyl SO—(CH$_2$)$_n$-phenyl, SO$_2$—(CH$_2$)$_n$-phenyl, where n can be =0–6, SO$_2$—NH$_2$, SO$_2$NH (C$_1$–C$_6$)-alkyl, SO$_2$N[(C$_1$–C$_6$)-alkyl ]$_2$, can be prepared according to methods known from the literature (Houben-Weyl, Methoden der Organischen Chemie [Methods of Organic Chemistry], Volume XI/1, p. 422 ff. and 475 ff., Thieme Verlag Stuttgart, incorporated herein by reference in its entirety) by subjecting the appropriately substituted compounds of the formula X or Xa, in which R1 and/or R1'=NO$_2$, to a reduction to the amines of the formula X or Xa, in which R1and/or R1'=NH$_2$, using, for example, Raney nickel and hydrogen in a solvent such as, for example, ethanol or glacial acetic acid, or using zinc in glacial acetic acid, or using tin or tin(II) chloride in hydrochloric acid, and then diazotizing by reaction with sodium nitrite in hydrochloric acid and converting further with $CuCl_2$ and $SO_2$ in glacial acetic acid to give the correspondingly substituted sulfonyl chloride. These can be converted reductively in the alkaline medium according to standard conditions into the corresponding sulfinic acids, which for their part are then processed further according to methods known from the literature to give compounds of the formula X or Xa, in which R1 and/or R1'=S—$(C_1$–$C_6)$-alkyl, S—phenyl, SO—$(C_1$–$C_6)$-alkyl, SO-phenyl, $SO_2$—$(C_1$–$C_6)$-alkyl, $SO_2$-phenyl, S—$(CH_2)_n$-phenyl, SO—$(CH_2)_n$-phenyl, $SO_2$—$(CH_2)_n$-phenyl, where n can be =0–6, $SO_2$—$NH_2$, $SO_2NH$ $(C_1$–$C_6)$-alkyl, $SO_2N[(C_1$–$C_6)$-alkyl$]_2$.

Compounds of the formula X or Xa, in which R1 and/or R1'=O—$(C_1$–$C_6)$-alkyl, O—$CH_2$–$CF_3$, O—$CH_2$—$CF_2$—$CF_3$, O—$(C_4$–$C_6)$-alkyl, where in the alkyl radicals one or more, or all hydrogen(s) can be replaced by fluorine, or one hydrogen can be replaced by OH, $OC(O)CH_3$, O—$CH_2$—Ph, $NH_2$ or $N(COOCH_2Ph)_2$, O—$(CH_2)_n$-phenyl, where n=0–6, S—$(C_1$–$C_6)$-alkyl, S-phenyl, S—$(CH_2)_n$-phenyl, where n can be =0–6, are accessible according to standard methods from compounds of the formula X or Xa, in which R1 and/or R1'=F or Br, by nucleophilic replacement with compounds of the formula R1-M or R1'-M, in which R1 and R1' have the meanings mentioned above and M is an alkali metal atom, such as, for example, Na, or a tetrasubstituted nitrogen atom, such as, for example, (n-Bu)$_4$N. For this, for example, a compound of the formula X or Xa, in which R1 and/or R1'=F, is advantageously reacted at 50 to 150° C. in a polar aprotic solvent such as dimethylformamide, N,N-dimethylacetamide, N-methyl-2-pyrrolidone or dimethyl sulfoxide with a compound of the formula R1-H or R1'-H, where R1 and R1' are as defined above, with addition of a base such as, for example, sodium or potassium carbonate, sodium hydride, potassium hexamethyldisilazane, potassium or sodium hydroxide, cesium carbonate or tetra-n-butylammonium hydroxide and then worked up in the customary manner.

Such compounds are also accessible by reacting compounds of the formula X or Xa, in which R1 and/or R1'=Br, under phase-transfer catalysis conditions (E. V. Dehmlow, S. S. Dehmlow, Phase Transfer Catalysis, 2nd. Ed., Verlag Chemie, Weinheim, 1983, incorporated herein by reference) with compounds of the formula R1-H and/or R1'-H with, for example, a catalyst such as Aliquat 336 in a mixture of toluene with 50% strength aqueous sodium hydroxide solution or with 15-crown-5 in toluene with 50% strength aqueous sodium hydroxide solution for about 2 h and then working up in the customary manner (A. J. Serio Duggan, E. J. J. Grabowski, W. K. Russ: Synthesis 573–5 (1980); A. Ohta, Y. Iwasaki, Y. Akita: Synthesis 828–9 (1982); W. Chin-Hsien, L. Xiang-Te, C. Xiao-Hun: Synthesis 858–61 (1982), incorporated herein by reference; H. Alsaidi, R. Gallo, J. Metzger: Synthesis 921–4 (1980), incorporated herein by reference).

After customary working up, compounds of the formula X or Xa in which R1 and/or R1'=O—$(C_1$–$C_6)$-alkyl, O—$CH_2$—$CF_3$, O—$CH_2$—$CF_2$—$CF_3$, O—$(C_4$–$C_6)$-alkyl, where in the alkyl radicals one or more, or all hydrogen(s) can be replaced by fluorine or a hydrogen can be replaced by OH, $OC(O)CH_3$, O—$CH_2$-Ph, $NH_2$ or $N(COOCH_2Ph)_2$, O—$(CH_2)_n$-phenyl, where n can be 0–6, S—$(C_1$–$C_6)$-alkyl, S-phenyl, S—$(CH_2)_n$-phenyl, where n can be =0–6, can thus be isolated.

Compounds of the formulae X and Xa, in which R1 and/or R1' is CN, can be obtained according to standard methods (L. Friedman, H. Shechter, J. Org. Chem. 26, 2522–24 (1961), incorporated herein by reference, from, for example, compounds of the formulae X and Xa, in which R1 and/or R1' is Cl or Br, by nucleophilic replacement with a metal cyanide, such as, for example, NaCN, KCN, Cu—(I)—CN. The solvent used for this is advantageously a polar, aprotic medium, such as, for example, dimethylformamide, dimethylacetamide, N-methyl-2-pyrrolidone or dimethyl sulfoxide. A suitable reaction temperature is 150 to 200° C.

ec) Compounds of the formulae XV and Xa, in which R1 and/or R1' are an optionally substituted aryl or heteroaryl radical, can be prepared from the corresponding compounds of the formulae XV and Xa, in which R1 and/or R1' is bromine, iodine or trifluoromethanesulfonyloxy, according to methods known from the literature. In analogy to N. Miyaura and A. Suzuki, Chem. Rev. 95, 2457–83 (1995) or T. Oh-e, N. Miyaura and A. Suzuki, J. Org. Chem. 58, 2201–08 (1993), incorporated herein by reference, such compounds can be obtained starting from bromo- or iodo(hetero)aryls or from (hetero)aryl triflates of the formula XV or Xa, in which R1 and/or R1' is bromine, iodine, trifluoromethanesulfonyloxy, by reaction with arylboronic acids or esters or arylborondialkyls of the formula R1-B or R1'-B, in which R1 and/or R1' can be an optionally substituted aryl radical such as, for example, phenyl, thienyl, pyridyl or furyl and B is a boron-containing radical such as $B(OH)_2$, $B(OCH_3)_2$, B(O—$(CH_2)_3$-O), $B(OC(CH_3)_2$—$C(CH_3)_2$—O) or $B(CH_2$—$CH_3)_2$, in such a way that the coupling reaction is carried out at 20 to 150° C. with addition of an organic base such as, for example, triethylamine or of an inorganic base such as, for example, sodium hydroxide, sodium carbonate, sodium hydrogencarbonate, potassium carbonate, potassium phosphate, barium hydroxide, cesium fluoride or tetrabutylammonium fluoride in a solvent mixture of, for example, toluene and water or acetone and water or dimethoxyethane and water or in solvents such as toluene, benzene, dimethoxyethane, tetrahydrofuran, dioxane, acetone or dimethylformamide with addition of a palladium catalyst. Suitable palladium catalysts are, for example: $Pd(OAc)_2$, $Pd(PPh_3)_4$, $PdCl_2(PPh_3)_2$, palladium (II)-[1,1-bis (diphenylphosphino)-ferrocene] chloride methylene chloride complex, $Pd[P(2-methoxyphenyl)_3]_4$ or $Pd(DBA)_2/[(MeO)_3C_6H_2]PPh_2$ ([DBA=dibenzylideneacetone]).

ed) Moreover, the compounds of the formulae XV and Xa, in which R1 and/or R1' are/is an optionally substituted aryl or heteroaryl radical, can also be prepared from the corresponding compounds of the formulae XV and Xa, in which R1 and/or R1' are/is a boron-containing radical such as $B(OCH_3)_2$ or $B(OC(CH_3)_2$—$C(CH_3)_2$—O). These are prepared in analogy to T. Ishiyama et al., J. Org. Chem. 60, 7508–10 (1995) or M. Murata et al., J. Org. Chem. 62, 6458–59 (1997), incorporated herein by reference, from the compounds of the formulae XV and Xa, in which R1 and/or R1' is bromine or iodine, by reaction with the pinacol ester of the diboronic acid [$(Me_4C_2O_2)BB(O_2C_2Me_4)$] or by reaction with 4,4,5,5-tetramethyl-1,3-2-dioxoborolane. Solvents employed are advantageously dimethyl sulfoxide, dimethylformamide, dioxane or toluene or mixtures thereof. The reaction temperature is about 80 to 100° C. A weak base such as, for example, potassium acetate and a palladium catalyst such as, for example, palladium(II)-[1,1'-bis (diphenylphosphino)ferrocene] chloride-methylene chloride complex or $PdCl_2(PPh_3)_2$ are further added to the reaction mixture. The compounds of the formulae XV and Xa thus obtained, in which R1 and/or R1' is a boron-containing radical such as $B(OCH_3)_2$ or $B(OC(CH_3)_2-C(CH_3)_2-O)$, can then be coupled as described under ec) with a compound R1—Br, R1—I, R1—OTf to give compounds of the formulae XV and Xa, in which R1 and/or R1' are/is an optionally substituted aryl or heteroaryl radical.

Compounds of the formulae XV and Xa, in which R1 and/or R1' are/is a boron-containing radical such as $B(OH)_2$, $B(OCH_3)_2$, $B(O-(CH_2)_3-O)$, $B(OC(CH_3)_2-C(CH_3)_2-O)$ or $B(CH_2-CH_3)_2$, can also be prepared in another manner from compounds of the formula XV or Xa in which R1 and/or R1' are/is bromine or iodine. For this, the aryl or heteroaryl halides of the formula XV or Xa, possibly after protection, as, for example, an acetal, of a carbonyl function which may be present, with butyllithium or lithium diisopropylamide in tetrahydrofuran at −78° C., are converted according to methods known from the literature (e.g. M. Ishikura et al., Chem. Pharm. Bull. 33, 4755–63 (1985), incorporated herein by reference) into the corresponding lithium compounds, which for their part are then reacted with a boric acid ester such as, for example, trimethyl borate or an alkoxydialkylborane such as, for example, methoxydiethylborane to give a boron-containing compound of the formula XV or Xa.

ee) A further method for the obtainment of compounds of the formula Xa, in which R1 and/or R1' are/is an optionally substituted aryl or heteroaryl radical, consists in reacting compounds of the formula XVI, in which R1 has the meanings mentioned at the outset, and $Sn(alkyl)_3$ is, for example, $Sn(n-butyl)_3$, in the sense of a Stille coupling according to methods known from the literature, such as are described, for example, in J. K. Stille, Angewandte Chemie, 98, 504–519 (1986), in T. N. Mitchell, Synthesis 803–815 (1992) or in T. Gan et al., Tetrahedron Lett. 38, 8453–56 (1997), incorporated herein by reference, with a compound R1'-Br or R1'-I, where R1' is an optionally substituted aryl or heteroaryl radical, under palladium catalysis with, for example, $Pd(PPh_3)_4$, $PdCl_2(PPh_3)_2$, $PdCl_2(PhCN)_2$ or $PdCl_2(CH_3CN)_2$ in a solvent such as, for example, tetrahydrofuran, toluene or dimethylformamide at temperatures between 20 and 150° C.

The organotin compounds of the formula XVI for their part are accessible, for example, from ring-brominated or -iodinated precursors by reaction with bistrialkyltin compounds, e.g. bistributyltin ($Bu_3SnSnBu_3$), according to processes known from the literature (J. K. Stille, Angewandte Chemie, 98, 504–519 (1986); T. Gan et al., Tetrahedron Lett. 38, 8453–56 (1997), incorporated herein by reference). In this process, a palladium catalyst such as, for example, $Pd(PPh_3)_4$ is added. The solvent used can be, for example, toluene; the reaction temperature is between 20 and 110° C. Moreover, the organotin compounds of the formula XVI, where $Sn(alkyl)_3$ can be, for example $Sn(CH_3)_3$, can be obtained in analogy to methods known from the literature (M. Gielen et al., Rev. Silicon Germanium Tin Lead Compd. 3, 9 (1977); M. Gielen, Rev. Silicon Germanium Tin Lead Compd. 5, 6 (1981), incorporated herein by reference) by reaction of the corresponding ring-brominated precursor with sodium trimethylstannate at about 0° C.

ef) Likewise, compounds of the formula Xa in which R1 and/or R1' are/is an optionally substituted aryl or heteroaryl radical can be obtained in such a way that compounds of the formula Xa, in which R1 and/or R1' are/is bromine or iodine, are reacted with aryl or heteroaryltintrialkyls of the formula $R1-Sn(alkyl)_3$ or $R1'-Sn(alkyl)_3$, in which R1 and R1' are an optionally substituted aryl or heteroaryl radical, under the conditions described under ee).

eg) Compounds of the formula Xa in which R1 and/or R1' are/is ($C_2-C_6$)-alkynyl or ($C_2-C_6$)-alkenyl can be obtained by methods known from the literature, as described in ec) and ee), by palladium-catalyzed reaction of, for example, trimethylsilylacetylene or alkynes (K. Sonagashira et al., Tetrahedron Lett. 4467 (1975); S. Takahashi et al., Synthesis 627 (1980)), alkynylzinc bromides (E. Negishi et al., J. Org. Chem. 62, 8957–60 (1997), incorporated herein by reference) or trialkyltinalkynes, of trialkyltinvinyl or allyl compounds, of 1-alkenylboron compounds or vinyl compounds (A. Hassner et al., J. Org. Chem. 49, 2546 (1984), incorporated herein by reference) with compounds of the formula Xa in which R1 and/or R1' are/is bromine, iodine or OTf.

The solution or suspensions of the compounds of the formula II thus obtained according to the respective method is expediently evaporated under reduced pressure and the compounds of the formula II are purified by crystallization from inert solvents such as, for example, benzene, toluene, tetrachloromethane, dichloromethane, 1,2-dichloroethane, cyclohexane, pentane, heptane. Advantageously, the compounds of the formula II thus obtained can also be reacted with 1 to 1.5 times the amount of a thiourea of the formula III in the manner described under a) above in a suitable inert solvent without further purification operations.

For the reaction of the compounds of the formula IV described in procedure b), the reaction is carried out in a solvent using the known compounds of the formula V. Particularly suitable solvents of this type are lower alcohols having 1 to 4 carbon atoms and lower alkyl esters of acetic acid having 1 to 4 carbon atoms in the alkyl moiety, such as, for example, methyl acetate and ethyl acetate. In general, the reactions are carried out in a temperature range between 0° and 60° C., preferably between 15° and 35° C., the reaction time being between 5 and 60 hours. The compounds of the formula I can be recrystallized from an inert, suitable solvent, such as, for example, acetone, methyl ethyl ketone, acetonitrile, nitromethane. However, reprecipitation from a solvent is particularly advantageous, such as, for example, in dimethylformamide, dimethylacetamide, nitromethane, acetonitrile, methanol, ethanol, isopropanol. The free bases of the formula I can also be advantageously purified by chromatography on silica gel. Suitable eluents are mixtures of dichloromethane with methanol, ethyl acetate with heptane, ethyl acetate with methanol.

The compounds of the formula I can optionally be converted into their salts using an acid of the formula H—Z. In this process, the compounds I can be introduced into the pure acids at temperatures between 0° and 40° C. if these are liquid or have a melting point which is not significantly higher than 40° C. Advantageously, however, the reaction is carried out in a solvent, such as, for example, in water or an organic solvent, such as, for example, in dioxane, tetrahydrofuran, diethyl ether, diisopropyl ether, tert-butyl methyl ether, a lower alkyl acetate having 1–4 carbon atoms in the alkyl moiety, acetonitrile, nitromethane, acetone, methyl ethyl ketone or lower alcohol having 1–4 carbon atoms. In this case, 1–1.5 mol of the acid H—Z are used per mole of the compounds I;

however, larger amounts of acid can also be used. Expediently, the reaction is carried out at temperatures between 0° and 40° C., preferably between 10° and 25° C. When working in aqueous solution, after addition of acids H—Z in general immediate dissolution of the compounds of the formula I occurs, and only rarely deposition of the corresponding acid addition compounds. Expediently, the salts according to the invention are isolated when a solution is obtained by careful evaporation of the water, preferably by freeze-drying. When working in organic solvents, the sparingly soluble acid addition salts frequently precipitate after addition of the respective acid H—Z. Otherwise, the acid addition compounds precipitate, if appropriate after prior concentration, using one of the precipitating agents mentioned.

The acid addition products are also obtained in a very high degree of purity, occasionally in the form of viscous oils or amorphous glass-like products. These amorphous products can be crystallized by treatment with an organic solvent at 40° to 80° C. Those suitable for this are, in particular, dialkyl ketones, such as acetone or methyl ethyl ketone, lower dialkyl ethers and acetonitrile, nitromethane and, if appropriate, alternatively lower alcohols.

The acid addition products can be deprotonated by treatment with bases to give the compounds of the formula I. Possible bases are, for example, solutions of inorganic hydroxides, such as lithium, sodium, potassium, calcium or barium hydroxide, carbonates or hydrogencarbonates, such as sodium or potassium carbonate, sodium or potassium hydrogencarbonate, ammonia and amines, such as triethylamine, diisopropylamine, dicyclohexylamine, piperidine, morpholine, methyldicyclo-hexylamine.

When working in an aqueous medium, the sparingly soluble free basic compounds I frequently precipitate and can be separated off by filtration or extraction with an organic solvent, preferably with ethyl acetate, and isolated. Suitable organic reaction media are particularly lower alcohols having 1–4 carbon atoms, preferably methanol, ethanol and isopropanol; however, ethyl acetate, diethyl ether, tetrahydrofuran, dioxane, ethylene glycol dimethyl ether, dimethylformamide can also be used. The reaction is carried out at −35° to 60° C., preferably between 0° and 25° C. If a water-miscible organic solvent is used, the free bases of the formula I are precipitated by addition of water, if appropriate after prior concentration of the reaction mixture.

When using a water-immiscible solvent, the reaction mixture is washed with water after the reaction and the organic solvent is evaporated.

The examples listed below serve to illustrate the invention, but without restricting it. The melting or decomposition points (m.p.) measured were not corrected and are generally dependent on the heating rate.

TABLE 1

Examples

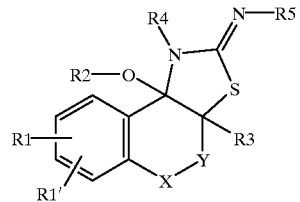

Formula I

| Example | R1; R1' | R2 | R3 | R4 | R5 | X | Y | Salt | M.p. [° C.] |
|---|---|---|---|---|---|---|---|---|---|
| A1 | 5-SO$_2$—CH$_3$; H | H | H | CH$_2$—CH$_3$ | CH$_2$—CH$_3$ | CH$_2$ | — | — | 131 |
| A2 | 5-SO$_2$—CH$_3$; H | H | H | CH$_2$—CH$_2$ | | CH$_2$ | — | — | 120 |
| A3 | 6-SO$_2$—CH$_3$; H | H | H | CH$_3$ | CH$_3$ | CH$_2$ | — | — | 153 |
| A4 | 5-SO$_2$—CH$_3$; H | H | H | C$_6$H$_5$ | C$_6$H$_5$ | CH$_2$ | — | — | 172 |
| A5 | 5-SO$_2$—CH$_3$; H | H | H | CH$_3$ | CH$_3$ | CH$_2$ | — | — | 159 |
| A6 | 5-SO$_2$—CH$_3$; H | H | H | CH$_3$ | CH$_3$ | CH$_2$ | — | HCl | >240 |
| A7 | 5-SO$_2$—CH$_2$—CH$_2$—CH$_3$; H | H | H | CH$_3$ | CH$_3$ | CH$_2$ | — | — | 109 |
| A8 | 5-SO$_2$—CH$_2$—C$_6$H$_5$; H | H | H | CH$_3$ | CH$_3$ | CH$_2$ | — | — | 164 |
| A9 | 5-SO$_2$—CH$_2$—CH$_2$—CH$_3$; H | H | H | CH$_2$—CH$_3$ | CH$_2$—CH$_3$ | CH$_2$ | — | — | 136 |
| A10 | 5-SO$_2$—CH$_2$—C$_6$H$_5$; H | H | H | CH$_2$—CH$_3$ | CH$_2$—CH$_3$ | CH$_2$ | — | — | 137 |
| A11 | 5-SO$_2$—C$_6$H$_5$; H | H | H | CH$_3$ | CH$_3$ | CH$_2$ | — | HCl | >200 |
| A12 | 5-CN; H | H | H | CH$_3$ | CH$_3$ | CH$_2$ | — | HCl | 169 |
| A13 | 5-SO$_2$(CH$_3$-2,4-di-CH$_3$); H | H | H | CH$_3$ | CH$_3$ | CH$_2$ | — | — | 115 |
| A14 | 5-S—(C$_6$H$_3$-2,4-di-CH$_3$); H | H | H | CH$_3$ | CH$_3$ | CH$_2$ | — | — | 138 |
| A15 | 5-S—(CH$_3$-2,4-di-CH$_3$); H | H | H | CH$_3$ | CH$_3$ | CH$_3$ | — | HCl | 250 |
| A16 | 7-S—CH$_2$—CH$_2$—CH$_2$—CH$_3$; H | H | H | CH$_3$ | CH$_3$ | CH$_2$ | — | HCl | 245 |
| A17 | 7-SO$_2$CH$_2$CH$_2$CH$_2$CH$_3$; H | H | H | CH$_3$ | CH$_3$ | CH$_2$ | — | — | 244 |
| A18 | 5-SO$_2$—CH$_3$; 6-S—C$_6$H$_5$ | H | H | CH$_3$ | CH$_3$ | CH$_2$ | — | — | 146 |
| A19 | 5-SO$_2$—CH$_3$; 6-SO$_2$—C$_6$H$_5$ | H | H | CH$_3$ | CH$_3$ | CH$_2$ | — | — | 160 |
| A20 | 6-C$_6$H$_5$; H | H | H | CH$_3$ | CH$_3$ | CH$_2$ | — | HBr | 280 |
| A21 | 6-C$_6$H$_5$; H | H | H | CH$_2$—CH$_3$ | CH$_2$—CH$_3$ | CH$_2$ | — | HBr | 140 |
| A22 | 6-(3-CF$_3$—C$_6$H$_4$); H | H | H | CH$_3$ | CH$_3$ | CH$_2$ | — | HBr | 199 |
| A23 | 6-CN; H | H | H | CH$_3$ | CH$_3$ | CH$_2$ | — | HBr | 283 |
| A24 | 6-(thien-3-yl); H | H | H | CH$_3$ | CH$_3$ | CH$_2$ | — | HBr | 197 |
| A25 | 6-(3-F—C$_6$H$_4$); H | H | H | CH$_3$ | CH$_3$ | CH$_2$ | — | HBr | 226 |
| A26 | 6-(4-CH$_3$—C$_6$H$_4$); H | H | H | CH$_3$ | CH$_3$ | CH$_2$ | — | HBr | 203 |

TABLE 1-continued

Examples

Formula I

| Example | R1; R1' | R2 | R3 | R4 | R5 | X | Y | Salt | M.p. [° C.] |
|---|---|---|---|---|---|---|---|---|---|
| A27 | 6-(O—C$_6$H$_4$-4-Cl); H | H | H | CH$_3$ | CH$_3$ | CH$_2$ | — | HCl | 249 |
| A28 | 6-O—CH$_2$—CF$_3$; H | H | H | CH$_3$ | CH$_3$ | CH$_2$ | — | HCl | 275 |
| A29 | 6-(4-CF$_3$—C$_6$H$_4$); H | H | H | CH$_3$ | CH$_3$ | CH$_2$ | — | HBr | 200 |
| A30 | 6-(3,5-di-CF$_3$—C$_6$H$_3$); H | H | H | CH$_3$ | CH$_3$ | CH$_2$ | — | HBr | 300 |
| A31 | 6-(3-Cl—C$_6$H$_4$); H | H | H | CH$_3$ | CH$_3$ | CH$_2$ | — | HBr | 209 |
| A32 | 6-(3-OCF$_3$—C$_6$H$_4$); H | H | H | CH$_3$ | CH$_3$ | CH$_2$ | — | HBr | 269 |
| A33 | 6-CH$_2$—CH$_3$; H | H | H | CH$_3$ | CH$_3$ | CH$_2$ | — | HBr | 274 |
| A34 | 6-(4-Cl—C$_6$H$_4$); H | H | H | CH$_3$ | CH$_3$ | CH$_2$ | — | HBr | 181 |
| A35 | 5-C(CH$_3$)$_3$; H | H | H | CH$_3$ | CH$_3$ | CH$_2$ | — | HBr | 278 |
| A36 | 6-(2-CF$_3$—C$_6$H$_4$); H | H | H | CH$_3$ | CH$_3$ | CH$_2$ | — | HBr | 200 |
| A37 | 6-(3-OCH$_3$—C$_6$H$_4$); H | H | H | CH$_3$ | CH$_3$ | CH$_2$ | — | HBr | 156 |
| A38 | 6-(1-naphthyl); H | H | H | CH$_3$ | CH$_3$ | CH$_2$ | — | HBr | 241 |
| A39 | 7-(4-CF$_3$—C$_6$H$_4$); H | H | H | CH$_3$ | CH$_3$ | CH$_2$ | — | HBr | 203 |
| A40 | 5-(4-Cl—C$_6$H$_4$); H | H | H | CH$_3$ | CH$_3$ | CH$_2$ | — | HBr | 212 |
| A41 | 6-OCF$_3$; H | H | H | CH$_3$ | CH$_3$ | CH$_2$ | — | HBr | 162 |
| A42 | 6-(pyrid-3-yl); H | H | H | CH$_3$ | CH$_3$ | CH$_2$ | — | HCl | 254 |
| A43 | 6-OC$_6$H$_5$; H | H | H | CH$_3$ | CH$_3$ | CH$_2$ | — | HCl | 254 |
| A44 | 6-(O—C$_6$H$_4$-3-CH$_3$); H | H | H | CH$_3$ | CH$_3$ | CH$_2$ | — | HCl | 238 |
| A45 | 6-O—CH$_2$—CF$_2$—CF$_2$—CF$_3$; H | H | H | CH$_3$ | CH$_3$ | CH$_2$ | — | HCl | 249 |
| A46 | 6-(O—C$_6$H$_4$-4-SO$_2$CH$_3$); H | H | H | CH$_3$ | CH$_3$ | CH$_2$ | — | — | 153 |
| A47 | 5-SO$_2$—CH$_3$; 6-Cl | H | H | CH$_3$ | CH$_3$ | CH$_2$ | — | — | 157 |
| A48 | 5-SO$_2$—CH$_3$; 6-Cl | H | H | | CH$_2$—CH$_2$ | CH$_2$ | — | — | 182 |
| A49 | 6-O—CH$_2$—CF$_2$—CF$_3$; H | H | H | CH$_3$ | CH$_3$ | CH$_2$ | — | HCl | 245 |
| A50 | 6-CCH; H | H | H | CH$_3$ | CH$_3$ | CH$_2$ | — | HBr | 144 |
| A51 | 6-CH=CH$_2$; H | H | H | CH$_3$ | CH$_3$ | CH$_2$ | — | HBr | >300 |
| A52 | 6-COOH; H | H | H | CH$_3$ | CH$_3$ | CH$_2$ | — | HBr | 286 |
| A53 | 6-CONH$_2$; H | H | H | CH$_3$ | CH$_3$ | CH$_2$ | — | HBr | 184 |
| A54 | 6-CONH$_2$; H | H | H | C(CH$_3$)$_3$ | C(CH$_3$)$_3$ | | — | HBr | 185 |
| A55 | 6-CH$_2$—CH$_3$ | H | H | CH$_3$ | CH$_3$ | CH$_2$ | — | HBr | 274 |
| A56 | 6-(CH$_2$)$_6$—O—C(O)CH$_3$ | H | H | C$_6$H$_5$ | C$_6$H$_5$ | CH$_2$ | — | — | 75 |
| B1 (rac) | 6-Cl; H | H | F | CH$_3$ | CH$_3$ | CH$_2$ | — | — | 190 |
| B1 (+) | 6-Cl; H | H | F | CH$_3$ | CH$_3$ | CH$_2$ | — | — | 176 |
| B1 (−) | 6-Cl; H | H | F | CH$_3$ | CH$_3$ | CH$_2$ | — | — | 177 |
| B2 (rac) | 6-Cl; H | H | F | CH$_3$ | CH$_3$ | CH$_2$ | — | HCl | 205 |
| B2 (−) | 6-Cl; H | H | F | CH$_3$ | CH$_3$ | CH$_2$ | — | HCl | 213 |
| B2 (+) | 6-Cl; H | H | F | CH$_3$ | CH$_3$ | CH$_2$ | — | HCl | 213 |
| B3 | 6-(CH$_2$)$_6$—OH; H | H | F | CH$_3$ | CH$_3$ | CH$_2$ | — | HCl | 183 |
| B4 | 6-Cl; H | H | F | CH$_2$—C$_6$H$_5$ | CH$_2$—C$_6$H$_5$ | CH$_2$ | — | — | 125 |
| B5 | 6-Cl; H | H | COOCH$_3$ | CH$_3$ | CH$_3$ | CH$_2$ | — | HBr | 186 |
| B6 | 6-Cl; H | H | F | CH$_3$ | CH$_3$ | CH$_2$ | — | — | 150 |
| B7 | Cl; H | H | COOH | CH$_3$ | CH$_3$ | CH$_2$ | — | — | 150 |
| C1 (rac) | 6-Cl; H | CH$_3$ | H | CH$_3$ | CH$_3$ | CH$_2$ | — | — | 94–96 |
| C2 | 6-Cl; H | CH$_3$ | H | C$_6$H$_4$-4-Cl | C$_6$H$_4$-4-Cl | CH$_2$ | — | — | 79 |
| C3 | 6-Cl; H | CH$_3$ | H | C$_6$H$_5$ | C$_6$H$_5$ | CH$_2$ | — | — | 64 |
| C4 | 6-Cl; H | CH$_3$ | H | C$_6$H$_4$-4-OCH$_3$ | C$_6$H$_4$-4-OCH$_3$ | CH$_2$ | — | — | 69 |
| C1 (+) | 6-Cl; H | CH$_3$ | H | CH$_3$ | CH$_3$ | CH$_2$ | — | — | 70 |
| C1 (−) | 6-Cl; H | CH$_3$ | H | CH$_3$ | CH$_3$ | CH$_2$ | — | — | 71 |
| C5 | 6-(C$_6$H$_4$-4-CF$_3$); H | CH$_3$ | H | CH$_3$ | CH$_3$ | CH$_2$ | — | — | 101 |
| C6 | 6-Cl; H | CH$_3$ | H | CH$_3$ | CH$_3$ | CH$_2$ | — | HCl | 65–70 |
| C7 | 6-Cl; H | CH$_2$—CH=CH$_2$ | F | CH$_3$ | CH$_3$ | CH$_2$ | — | HCl | 153 |
| D1 | H; H | H | H | CH$_3$ | CH$_3$ | CH(C$_6$H$_5$) | — | HBr | 194 |
| D2 | H; H | H | H | CH$_3$ | CH$_3$ | CH(C$_6$H$_4$-2-Cl) | — | HBr | 158 |
| D3 | H; H | H | H | CH$_3$ | CH$_3$ | S | CH$_2$ | HBr | 220 |
| D4 | H; H | H | H | CH$_2$—CH$_2$ | | S | CH$_2$ | HBr | 261 |
| D5 | H; H | H | H | C(CH$_3$)$_2$—CH$_2$ | | S | CH$_2$ | HBr | 130 (233 (dec)) |
| D6 | H; H | H | H | CH$_2$—CH$_3$ | CH$_2$—CH$_3$ | S | CH$_2$ | HBr | 144 |
| D7 | H; H | H | H | CH$_2$—CH$_2$—CH$_2$ | | S | CH$_2$ | HBr | 171 |

TABLE 1-continued

Examples

Formula I

| Example | R1; R1' | R2 | R3 | R4 | R5 | X | Y | Salt | M.p. [° C.] |
|---|---|---|---|---|---|---|---|---|---|
| D8 | H; H | H | H | $CH_3$ | $CH(CH_3)_2$ | S | $CH_2$ | HBr | 151 |
| D9 | H; H | H | H | $CH_3$ | $CH_2-C_6H_5$ | S | $CH_2$ | HBr | 153 |
| D10 | 5-Cl; H | H | H | $CH_3$ | $CH_3$ | S | $CH_2$ | HBr | 157 |
| D11 | 5-Cl; H | H | H | H | $C(CH_3)_2-CH_2$ | S | $CH_2$ | HBr | 148 |
| D12 | H; H | H | H | H | $C(CH_3)_2-CH_2$ | O | $CH_2$ | HBr | 228 |
| D13 | H; H | H | H | H | $CH_2-CH_2$ | $CH(C_6H_5)$ | $CH_2$ | HBr | 285 |
| D14 | H; H | H | H | $CH_3$ | $CH_3$ | $CH(C_6H_5)$ | $CH_2$ | HBr | 253 |
| D15 | 5-$NO_2$; H | H | H | $CH_3$ | $CH_3$ | O | $CH_2-CH_2$ | — | 175 |
| D16 | 5-$NO_2$; H | H | H | $CH_2-CH_3$ | $CH_2-CH_3$ | O | $CH_2-CH_2$ | — | 126 |
| D17 | 5-Cl; H | H | H | $CH_3$ | $CH_3$ | O | $CH_2$ | — | 129 |
| D18 | S-Cl; H | H | H | $CH_3$ | $CH_3$ | O | $CH_2$ | HCl | 232 |
| D19 | 5-$NO_2$; H | H | H | $CH_3$ | $CH_3$ | O | $CH_2$ | HCl | 210 |
| D20 | H; H | H | H | $CH_3$ | $CH_3$ | O | $CH_2$ | — | 131 |
| D21 | H; H | H | H | $CH_3$ | $CH_3$ | $SO_2$ | $CH_2-CH_2$ | — | 143 |
| D22 | H; H | H | H | $CH_3$ | $CH_3$ | O | $CH_2-CH_2$ | — | 169 |
| D23 | 6-Cl; H | H | H | $CH_3$ | $CH_3$ | O | $CH_2-CH_2$ | — | 134 |
| D24 | H; H | H | H | $CH_3$ | $CH_3$ | $N-SO_2-$ $(C_6H_4-4-CH_3)$ | $CH_2-CH_2$ | — | 164 |
| D25 | 5-NH-C(O)$CH_3$; H | H | H | $CH_3$ | $CH_3$ | O | $CH_2-CH_2$ | HCl | 270 |
| D26 | 5-CN; H | H | H | $CH_3$ | $CH_3$ | O | $CH_2-CH_2$ | — | 169 |
| D27 | 5-$SO_2CH_2CH_2CH_2CH_3$; H | H | H | $CH_3$ | $CH_3$ | O | $CH_2-CH_2$ | — | 172 |
| D28 | 5-$SO_2-C(CH_3)_3$; H | H | H | $CH_3$ | $CH_3$ | O | $CH_2-CH_2$ | HCl | 176 |
| D29 | 5-$SO_2-C_6H_5$; H | H | H | $CH_3$ | $CH_3$ | O | $CH_2-CH_2$ | HCl | 170 |
| D30 | 5-$SO_2-CH_3$; H | H | H | $CH_3$ | $CH_3$ | O | $CH_2-CH_2$ | — | 161 |
| D31 | 5-NH—C(O)$CH_3$; H | H | H | $CH_3$ | $CH_3$ | O | $CH_2-CH_2$ | — | 187 |
| E1 | 6-Cl; H | H | H | $C_6H_4$-4-Cl | $C_6H_4$-4-Cl | $CH_2$ | — | HBr | 257 |
| E2 | 6-Cl; H | H | H | $C_6H_4$-4-$OCH_3$ | $C_6H_4$-4-$OCH_3$ | $CH_2$ | — | HBr | 233 |
| E3 | 6-Cl; H | H | H | $C_6H_5$ | $C_6H_5$ | $CH_2$ | — | HBr | 125 |
| E4 | 6-Cl; H | H | H | $C_6H_3$-5-Cl-2-$CH_3$ | $C_6H_3$-5-Cl—2-$CH_3$ | $CH_2$ | — | HBr | 179 |
| E5 | 6-Cl; H | H | H | $C_6H_3$-2,4-di-F | $C_6H_3$-2,4-di-F | $CH_2$ | — | HBr | 194 |

The compounds of the formula I are distinguished by favorable effects on the lipid metabolism; in particular, they are suitable as anorectics. The compounds can be employed on their own or in combination with further anorectic active compounds (see for example, Rote Liste, Chapter 01—Abmagerungsmittel/Appetitzgüler). The compounds are furthermore suitable for the prophylaxis and for the treatment of type II diabetes.

The efficacy of the compounds was tested as follows:
Biological test model

The anorectic action was tested on male NMRI mice. After withdrawal of feed for 24 hours, the test preparation was administered via a stomach tube. Kept individually and with free access to drinking water, the animals were offered evaporated milk 30 minutes after giving the preparation. The consumption of evaporated milk was determined half-hourly for 7 hours and the general condition of the animals was observed. The measured milk consumption was compared with that of the untreated control animals.

TABLE 2

Anorectic action, measured as the reduction of the cumulated milk consumption of treated animals in comparison with the untreated animals.

Compound/example

Formula I: [structure with R1, R1', R2-O, R4-N, N-R5, S, R3, X, Y groups]

| | Oral dose [mg/kg] | Number of animals/ cumulated milk consumption of the treated animals N/[ml] | Number of animals/ cumulated milk consumption of the untreated control animals N/[ml] | Reduction in the cumulated milk consumption in % of the control |
|---|---|---|---|---|
| Comparison compound: [structure with H, BrH3C, HO, N, CH3, S] | 50 | 6/1.62 | 12/2.61 | 38 |
| Y = direct bond; X = CH₂; R1 = R1' = R2 = R3 = H; R4 = R5 = CH₃; HBr salt | | | | |
| Example A27 | 50 | 5/0.44 | 5/4.04 | 89 |
| Example A28 | 50 | 5/0.06 | 5/4.00 | 98 |
| Example A35 | 50 | 5/2.46 | 5/5.50 | 55 |
| Example A39 | 50 | 5/1.48 | 5/5.42 | 73 |
| Example A41 | 50 | 5/0.84 | 5/3.12 | 73 |
| Example A42 | 50 | 5/0.60 | 5/2.94 | 80 |
| Example A45 | 50 | 5/0.06 | 5/2.78 | 98 |
| Example A50 | 50 | 5/1.56 | 4/3.53 | 56 |
| Example B1 (rac) | 50 | 5/0.06 | 5/2.94 | 98 |
| Example B1 (−) | 50 | 5/0.08 | 5/3.40 | 98 |
| Example B2 (rac) | 50 | 5/0.06 | 5/3.40 | 98 |
| Example B2 (+) | 50 | 10/1.37 | 10/4.56 | 70 |
| Example B2 (−) | 50 | 10/0.22 | 10/4.80 | 95 |
| Example C6 | 50 | 5/0.42 | 5/3.64 | 88 |
| Example D29 | 50 | 5/1.84 | 5/4.74 | 61 |
| Example E2 | 50 | 5/0.34 | 5/2.78 | 88 |

It can be inferred from the table that the compounds of the formula I exhibit a very good anorectic action. The anorectic action is also markedly improved compared with the comparison example.

The preparation of some examples is described in detail below; the other compounds of the formula I were obtained analogously:

EXAMPLE 1 (COMPOUND A4)
5-Methanesulfonyl-3-phenyl-2-phenylimino-2,3,8,8a-tetrahydroindeno[1,2-d]thiazol-3a-ol a) Indan-1-one-6-sulfonyl chloride 5.2 g of sodium nitrite in 11 ml of water are added dropwise at 0–5° C. to a suspension of 10.7 g of commercially obtainable 6-aminoindan-1-one in 100 ml of half-concentrated hydrochloric acid and the mixture is stirred for 15 min. The resulting solution is added dropwise to a mixture of 6.4 g of CuCl₂×2H₂O in 20 ml of water and 195 ml of a saturated solution of SO₂ in glacial acetic acid. After the evolution of nitrogen has subsided, the mixture is stirred at room temp. for 1 hour. By addition of 400 ml of water, the crystallization of the desired product (indan-1-one-6-sulfonyl chloride) is achieved, which is filtered off with suction and washed with a little cold water. It has a melting point of 75° C.

b) Indan-1-one-6-sulfinic acid: 2.1 g of solid NaOH and 18.1 g of NaHSO₃ are dissolved in 53 ml of water. 2N NaOH is added simultaneously and 8 g of indan-1-one-6-sulfonyl chloride are introduced in portions such that the pH remains at 7–7.2. The temp. increases in the course of this to about 35° C. The mixture is stirred at room temp. for 2 hours, carefully acidified with conc. hydrochloric acid and concentrated to dryness, the residue is extracted twice by boiling with about 200 ml of methanol and the filtrate is concentrated again. The residue is triturated with a little acetone, filtered off with suction and dried in vacuo. Indan-1-one-6-sulfinic acid is obtained, which decomposes at 275° C.

c) 6-Methanesulfonyl-indan-1-one: 0.75 g of sodium is dissolved in 75 ml of anhydrous methanol. 5.9 g of indan-1-one-6-sulfinic acid are added in portions and the mixture is stirred at room temp. for 30 min. 7.5 ml of methyl iodide are then added and the mixture is stirred at reflux temp. for 4 hours. After standing overnight, it is concentrated, the residue is extracted by shaking with water and CH₂Cl₂, the org. phase is dried and concentrated, and the residue is crystallized using diisopropyl ether. After filtering off with suction and drying, 6-methanesulfonylindan-1-one of melting point 155° C. is obtained.

d) 2-Bromo-6-methanesulfonylindan-1-one: 3.15 g of 6 methanesulfonylindan-1-one are suspended in 50 ml of glacial acetic acid and treated with 0.4 ml of 48% HBr solution. 0.92 ml of bromine in 10 ml of glacial acetic acid are added at room temp. and the mixture is stirred for 2 hours. It is poured onto ice, and the precipitate formed is filtered off with suction and washed with cold water. The product is purified by column chromatography on $SiO_2$ using dichloromethane. Some dibromo derivative is obtained as the preliminary fraction and 2-bromo-6-methanesulfonylindan-1-one of melting point 120° C. as the main product.

e) 5-Methanesulfonyl-3-phenyl-2-phenylimino-2,3,8,8a-tetrahydro-indeno[1,2-d]thiazol-3a-ol:

1.45 g of 2-bromo-6-methanesulfonylindan-1-one are dissolved in 15 ml of acetone and treated with stirring with 1.25 g of N,N'-diphenylthiourea in 25 ml of acetone. The hydrobromide of 5-methanesulfonyl-3-phenyl-2-phenylimino-2,3,8,8a-tetrahydro-indeno[1,2-d]thiazol-3a-ol crystallizes out of the clear solution after about 2 hours. After standing overnight, it is filtered off with suction and washed with a little acetone. 1.7 g of hydrobromide (m.p. 247° C.) are dissolved in 10 ml of methanol and treated with 0.8 ml of triethylamine. After 15 min, 150 ml of water are added and the mixture is stirred for 30 min with ice-cooling. The product formed is filtered off with suction and washed with a little cold water. 5-Methanesulfonyl-3-phenyl-2-phenylimino-2,3,8,8a-tetrahydroindeno[1,2-d]thiazol-3a-ol of melting point 172° C. is obtained.

EXAMPLE 2 (COMPOUND A9)

3-Ethyl-2-ethylimino-5-(propane-1-sulfonyl)-2,3,8,8a-tetrahydroindeno -[1,2-d]thiazol-3a-ol a) 6-(Propane-1-sulfonyl)indan-1-one:

0.25 g of sodium is dissolved in 50 ml of anhydrous methanol. 1.96 g of indan-1-one-6-sulfinic acid (see above) are added in portions and the mixture is stirred for 30 min at room temp. 1.87 g of 1-iodopropane are then added and the mixture is stirred for 4 hours at reflux temp. For completion of the reaction, the mixture is concentrated in vacuo, treated with 5 ml of iodopropane and 10 ml of toluene and heated to reflux for 2 hours. It is then concentrated, the residue is extracted by shaking with water and $CH_2Cl_2$, the org. phase is dried and concentrated, and the residue is purified by column filtration ($SiO_2$; cyclohexane/ethyl acetate=2/1). 6-(Propane-1-sulfonyl)indan-1-one of melting point 100° C. is obtained.

b) 2-Bromo-6-(propane-1-sulfonyl)indan-1-one: The reaction of 6-(propane-1-sulfonyl)indan-1-one to give 2-bromo-6-(propane-1-sulfonyl)indan-1-one is carried out analogously to the preparation of 2-bromo-6-methanesulfonylindan-1-one. The crude product can be purified by crystallization and washing with low-boiling petroleum ether. 2-Bromo-6-(propane-1-sulfonyl)indan-1-one of melting point 87–89° C. is obtained.

c) 3-Ethyl-2-ethylimino-5-(propane-1-sulfonyl)-2,3,8,8a-tetrahydro-indeno[1,2-d]thiazol-3a-ol: 951 mg of 2-bromo-6-(propane-1-sulfonyl)indan-1-one are dissolved in 20 ml of acetone and treated with 528 mg of N,N'-diethylurea in 10 ml of acetone with stirring. After about 10 min, the hydrobromide of 3-ethyl-2-ethylimino-5-(propane-1-sulfonyl)-2,3,8,8a-tetrahydroindeno[1,2-d]thiazol-3a-ol crystallizes out. The mixture is stirred at room temp. for a further hour, and the precipitate is filtered off with suction and washed with a little acetone. After drying, the hydrobromide of 3-ethyl-2-ethylimino-5-(propane-1-sulfonyl)-2,3,8,8a-tetrahydroindeno[1,2-d]thiazol-3a-ol of melting point 146° C. is obtained. This is dissolved in 10 ml of methanol and treated with 0.4 ml of triethylamine. After 15 min, 50 ml of water are added and the mixture is stirred in an ice bath for 1 hour. The crystallizate formed is filtered off with suction, washed with water and purified by column filtration ($SiO_2$, ethyl acetate/methanol 3/1). 3-Ethyl-2-ethylimino-5-(propane-1-sulfonyl)-2,3,8,8a-tetrahydroindeno[1,2-d]-thiazol-3a-ol of melting point 136° C. is obtained.

The compounds of Examples A1, A2 (use of imidazolidine-2-thione), A3 (use of 5-aminoindan-1-one)), A5, A6, A7, A8, A10, A17 (use of 4-amino-indan-1-one), A 47, A48 (use of 5-chloro-6-nitroindan-1-one) were prepared analogously.

EXAMPLE 3 (COMPOUND A21)

3-Ethyl-2-ethylimino-6-phenyl-2,3,8,8a-tetrahydroindeno [1,2-d]thiazol-3a-ol hydrobromide a) 5-Phenylindan-1-one: 4.22 g of 5-bromoindan-1-one, 2.44 g of phenylboronic acid and 4.24 g of sodium carbonate are suspended in a mixture of 100 ml of toluene with 20 ml of ethanol and 20 ml of water. After the addition of 450 mg of palladium(II) acetate and 1.05 g of triphenylphosphine, the mixture is heated under reflux for 5 h. The ethanol part of the reaction mixture is then removed by distillation in vacuo, and the reaction mixture is treated with 50 ml of 0.5N sodium hydroxide solution and stirred at room temperature for 15 minutes. The organic phase is separated off and the aqueous part is additionally extracted a further two times by shaking with toluene. The combined organic phases are washed with water, then with satd. sodium chloride solution, dried over magnesium sulfate and concentrated in vacuo. The residue is stirred with n-heptane, filtered off with suction, washed with n-pentane and dried in vacuo at room temperature. 5-phenylindan-1-one of melting point 75° C. is obtained.

b) 2-Bromo-5-phenylindan-1-one: 3.19 g of 5-phenylindan-1-one are dissolved in 25 ml of glacial acetic acid. 10 μl of a 48% strength solution of HBr in glacial acetic acid are added and a solution of 0.592 ml of bromine in 5 ml of glacial acetic acid is added dropwise with stirring at room temperature in the course of 15 minutes. The reaction mixture is stirred at room temperature for a further two hours before adding 0.057 ml of bromine, stirred for a further hour, and the reaction mixture is then added to ice water (15 g of water, 45 g of ice, 150 mg of sodium hydrogencarbonate). The deposited precipitate is filtered off with suction and chromatographed on silica gel using toluene/ethyl acetate 10/1. 2-Bromo-5-phenylindan-1-one of melting point 99–100° C. is obtained.

c) 3-Ethyl-2-ethylimino-6-phenyl-2,3,8,8a-tetrahydroindeno[1,2-d]-thiazol-3a-ol hydrobromide 718 mg of 2-bromo-5-phenylindan-1-one are dissolved in 20 ml of dry acetone. A solution of 397 mg of N,N'-diethylthiourea in 10 ml of dry acetone is added dropwise to this solution at 5° C. in the course of 5 minutes. The reaction mixture is stirred at room temperature for 2 hours, and the precipitate is then filtered off with suction and washed with acetone. 3-Ethyl-2-ethylimino-6-phenyl-2,3,8,8a-tetrahydroindeno[1,2-d] thiazol-3a-ol hydrobromide of melting point 140–141° C. (decomposition) is obtained.

Starting from 5-bromoindan-1-one, the compounds A22, A24, A25, A26, A29, A30, A31, A32, A34, A36, A37, A38 were prepared analogously.

EXAMPLE 4 (COMPOUND A39)

3-Methyl-2-methylimino-7-(4-trifluoromethylphenyl)-2,3, 8,8a-tetrahydro-indeno[1,2- d]thiazol-3a-ol hydrobromide a) 4-(4-Trifluoromethylphenyl)indan-1-one: 6.33 g of 4-bromoindan-1-one, 5.7 g of 4-(trifluoromethyl)-phenylboronic acid and 6.36 g of sodium carbonate are suspended in a mixture of 100 ml of toluene with 20 ml of ethanol and 20 ml of water with stirring. 320 mg of palladium(II) acetate and 787 mg of triphenylphosphine are added under a protective gas atmosphere (argon) and the mixture is stirred under reflux for 3 hours. After a further hour, 1.45 g of 4-(trifluoromethyl)phenylboronic acid and 320 mg of palladium(II) acetate are added again and the mixture is boiled for a further 2 hours. The ethanol is removed from the cooled reaction mixture by distillation in vacuo, and the residue is treated with 50 ml of 0.5N sodium hydroxide solution, stirred and filtered. The organic phase of the filtrate is washed a number of times with 50 ml of water in each case and finally with 50 ml of satd. sodium chloride solution, dried over magnesium sulfate and concentrated. The residue is chromatographed on silica gel using n-heptane/ethyl acetate 3/1 and 4-(4-trifluoromethylphenyl)indan-1-one of melting point 81° C. is obtained.

b) 2-Bromo-4-(4-trifluoromethylphenyl)indan-1-one: 2.76 g of 4-(4-trifluoromethylphenyl)indan-1-one are dissolved in 20 ml of glacial acetic acid. 10 μl of a 48% strength solution of hydrobromic acid in glacial acetic acid are added and a solution of 0.516 ml of bromine in 5 ml of glacial acetic acid is then slowly added dropwise. The reaction mixture is stirred at room temperature for 3 hours and then poured into a mixture of 100 ml of water with 100 g of ice and 100 mg of sodium hydrogencarbonate. The aqueous suspension is extracted by shaking with dichloromethane, and the organic phase is washed three times with water, dried over magnesium sulfate, concentrated and chromatographed on silica gel using dichloromethane/n-heptane 3/1. 2-Bromo-4-(4-trifluoromethylphenyl)indan-1-one of melting point 94–97° C. is obtained.

c) 3-Methyl-2-methylimino-7-(4-trifluoromethylphenyl)-2,3,8,8a-tetrahydroindeno[1,2-d]thiazol-3a-ol hydrobromide: 426 mg of 2-bromo-4-(4-trifluoromethylphenyl)indan-1-one and 131 mg of N,N'-dimethylthiourea are mixed together in 10 ml of acetone at room temperature and the mixture is stirred for 4 hours. The deposited precipitate is filtered off with suction, washed with acetone and dried in vacuo. 3-Methyl-2-methylimino-7-(4-trifluoromethylphenyl)-2,3,8,8a-tetrahydroindeno[1,2-d]thiazol-3a-ol hydrobromide of melting point 202–204° C. is obtained.

Starting from 4-bromoindan-1-one, the compound A40 was obtained analogously.

EXAMPLE 5 (COMPOUND A42)

3-Methyl-2-methylimino-6-pyridin-3-yl-2,3,8,8a-tetrahydroindeno[1,2-d]-thiazol-3a-ol hydrochloride a) 5-Pyridin-3-yl-indan-1-one: 13.26 g of 3-bromopyridine are dissolved in 160 ml of diethyl ether and cooled to −60° C. 52 ml of a 1.6 molar solution of n-butyllithium in n-hexane are added dropwise to this solution. The solution is allowed to warm to −30° C. and 9.5 ml of trimethyl borate are added dropwise with stirring at this temperature. The reaction mixture is subsequently heated under reflux for 3 hours, then cooled to 0° C. and treated dropwise with 6.1 ml of 1,3-propanediol. This mixture is stirred at 0° C. for 30 minutes before 5.46 ml of methanesulfonic acid are added dropwise and is stirred for a further 30 minutes. 20 g of Celite are then added, the mixture is warmed to room temperature and filtered, the filtrate is concentrated, the residue is stirred in 700 ml of toluene and filtered again, and the solvent is removed by distillation in vacuo. 4.1 g of the residue (3-[1,3,2] dioxaborinan-2-yl-pyridine) are dissolved in a mixture of 100 ml of toluene with 20 ml of ethanol and 20 ml of water without further purification together with 4.22 g of 5-bromoindan-1-one and 4.24 g of sodium carbonate. The solution is flushed with argon, and 112 mg of palladium(II) acetate and 262 mg of triphenylphosphine are then added. The reaction mixture is refluxed for 4 hours, cooled to room temperature and the ethanol part of the mixture is removed by distillation in vacuo. 50 ml of a 0.5N sodium hydroxide solution are then added with stirring, the organic phase is separated off and the aqueous phase is extracted by shaking with toluene. The combined organic phases are extracted by shaking successively with water and satd. sodium chloride solution, dried over magnesium sulfate, concentrated in vacuo and purified by chromatography on silica gel using ethyl acetate/n-heptane 1/1. 5-Pyridin-3-ylindan-1-one of melting point 103–106° C. is obtained.

b) 2-Chloro-5-pyridin-3-ylindan-1-one: 3.22 g of 5-pyridin-3-ylindan-1-one are dissolved in 160 ml of dichloromethane and treated dropwise with a solution of 1.34 ml of sulfuryl chloride in 40 ml of dichloromethane at 0° C. in the course of 15 minutes. The mixture is stirred at 0° C. for 30 minutes and then at room temperature for 60 minutes before 50 ml of a satd. sodium hydrogencarbonate solution are slowly added. The organic phase is separated off, washed with water, dried over magnesium sulfate, concentrated in vacuo and purified by chromatography on silica gel using dichloromethane/methanol 50/1. 2-Chloro-5-pyridin-3-ylindan-1-one of melting point 103–105° C. is obtained (in addition to 2,2-dichloro-5-pyridin-3-ylindan-1-one of melting point 109° C.).

c) 3-Methyl-2-methylimino-6-pyridin-3-yl-2,3,8,8a-tetrahydroindeno-[1,2-d]thiazol-3a-ol hydrochloride: 366 mg of 2-chloro-5-pyridin-3-ylindan-1-one and 235 mg of N,N'-dimethylthiourea are dissolved in 5 ml of methanol and refluxed for 7 hours. The reaction mixture is cooled and concentrated in vacuo. The residue is treated with 5 ml of acetone, stirred in an ultrasonic bath for 30 minutes and then filtered off with suction. The residue is washed with acetone and dried in vacuo. The hydrochloride of 3-methyl-2-methylimino-6-pyridin-3-yl-2,3,8,8a-tetrahydroindeno-[1,2-d]thiazol-3a-ol having a melting point of 253–255° C. is obtained.

EXAMPLE 6 (COMPOUND A41)

3-Methyl-2-methylimino-6-trifluoromethoxy-2,3,8,8a-tetrahydroindeno-[1,2-d]thiazol-3a-ol hydrobromide a) Methyl 3-trifluoromethoxycinnamate:

9.15 g of 3-trifluoromethoxycinnamic acid are dissolved in 90 ml of methanol. 0.25 ml of conc. sulfuric acid is added and the mixture is refluxed for 5 hours. The cooled solution is carefully treated with 0.9 g of sodium hydrogencarbonate, stirred for 5 minutes and then concentrated in vacuo. The residue is taken up in 250 ml of ethyl acetate, washed twice with 50 ml of water each time and dried over magnesium sulfate. The solution is concentrated in vacuo and the residual pale oil is reacted further without further purification.

b) Methyl 3-(3-trifluoromethoxyphenyl)propionate: 9.6 g of methyl 3-trifluoromethoxycinnamate are dissolved in 200 ml of methanol. 750 mg of palladium on carbon (10% strength) are added and the mixture is hydrogenated at normal pressure. After customary working up, methyl 3-(3-trifluoromethoxyphenyl)propionate is obtained as a yellow oil.

c) 5-Trifluoromethoxyindan-1-one: 9.37 g of methyl 3-(3-trifluoromethoxyphenyl)propionate are dissolved in 50 ml of ethanol with 25 ml of water. 3.74 g of potassium hydroxide are added and the mixture is refluxed for 45 minutes. The cooled solution is concentrated, the residue is treated with 25 ml of water, and conc. hydrochloric acid is added with stirring until the pH is 1. The aqueous reaction mixture is extracted twice by shaking with 75 ml of dichloromethane in each case. The organic phase is washed with water, dried over magnesium sulfate, concentrated and dried in vacuo. 3-(3-trifluoromethoxy-phenyl) propionic acid is obtained as a colorless oil. 6.24 g of the acid are dissolved in 40 ml of toluene, and the solution is treated with 2.1 ml of thionyl chloride and refluxed for 1 hour. The cooled reaction mixture is concentrated, and the residue is taken up in 5 ml of toluene and concentrated again. 3-(3-Trifluoromethoxyphenyl)propionyl chloride is obtained, which is dissolved in 30 ml of dichloromethane without further purification and added dropwise at 0–5° C. with stirring in the course of 15 minutes to a suspension of 5.49 g of anhydrous aluminum trichloride in 40 ml of dichloromethane. The reaction mixture is stirred at 0° C. for one hour and then added to 40 ml of ice water. The organic phase is separated off and the aqueous phase is again extracted by shaking with 40 ml of dichloromethane. The combined organic phases are washed with 40 ml of satd. sodium hydrogencarbonate solution and water, dried over magnesium sulfate, concentrated in vacuo and, for purification, purified by chromatography on silica gel using toluene/ethyl acetate 20/1. 5-Trifluoromethoxyindan-1-one is obtained as a pale yellow oil.

d) 2-Bromo-5-trifluoromethoxyindan-1-one: 5.3 g of 5-trifluoromethoxyindan-1-one are dissolved in 50 ml of glacial acetic acid, treated with 110 μl of hydrobromic acid (48% strength in glacial acetic acid) and treated dropwise at room temperature with a solution of 1.305 ml of bromine in 12 ml of acetic acid. The reaction mixture is stirred at room temperature for 90 minutes, then treated with 70 ml of water and extracted twice by shaking with 100 ml of dichloromethane each time. The organic phases are washed with 50 ml of water, dried over magnesium sulfate, concentrated in vacuo and the residue is chromatographed on silica gel using toluene/ethyl acetate 50/1. 2-Bromo-5-trifluoromethoxyindan-1-one is obtained as a wax.

e) 3-Methyl-2-methylimino-6-trifluoromethoxy-2,3,8,8a-tetrahydroindeno[1,2-d]thiazol-3a-ol hydrobromide: 0.197 g of 2-bromo-5-trifluoromethoxyindan-1-one is stirred at room temperature for 5 hours with 0.104 g of N,N'-dimethylthiourea in 5 ml of acetone. The suspension obtained is additionally stirred at 0° C. for 1 hour and then filtered off with suction; the residue is washed with acetone and dried in vacuo. The hydrobromide of 3-methyl-2-methylimino-6-trifluoromethoxy-2,3,8,8a-tetrahydroindeno[1,2-d]-thiazol-3a-ol melts at 162° C. with decomposition.

EXAMPLE 7 (COMPOUND A35)

5-tert-Butyl-3-methyl-2-methylimino-2,3,8,8a-tetrahydroindeno[1,2-d]-thiazol-3a-ol hydrobromide:

a) Methyl 3-(4-tert-butylphenyl)acrylate: 3-(4-tert-Butylphenyl)acrylic acid is reacted with sulfuric acid in methanol to give methyl 3-(4-tert-butylphenyl)acrylate analogously to Example 6a). The ester has a waxy consistency with a melting point of about 35° C.

b) Methyl 3-(4-tert-butylphenyl)propionate: 10.0 g of the methyl 3-(4-tert-butylphenyl)acrylate are dissolved in 75 ml of absolute methanol. 2.45 g of magnesium turnings are introduced in portions in the course of one hour and the mixture is stirred at room temperature for three hours. 380 mg of magnesium turnings are then added and the mixture is stirred for a further hour. With cooling (ice bath), 90 ml of 2N hydrochloric acid are carefully added dropwise with stirring. The methanol is then removed in vacuo, the residue is extracted twice with 200 ml of dichloromethane in each case, and the dichloromethane phase is washed with water until neutral (2×50 ml), dried over magnesium sulfate and concentrated. Methyl 3-(4-tert-butylphenyl)propionate is obtained as a colorless, waxy compound.

c) 3-(4-tert-Butylphenyl)propionic acid: 9.90 g of methyl 3-(4-tert-butylphenyl)propionate are dissolved in a mixture of 30 ml of ethanol with 15 ml of water, and the solution is treated with 4.46 g of potassium hydroxide, heated under reflux for 45 minutes, then concentrated in vacuo, treated with 30 ml of water and, while cooling with an ice bath, adjusted to pH 1 using conc. hydrochloric acid. The aqueous solution is extracted three times by shaking with 100 ml of dichloromethane in each case, washed with water until neutral, dried over magnesium sulfate and concentrated in vacuo. The residue is stirred with 100 ml of 25% strength acetic acid, cooled to 10° C. and filtered off with suction and dried in vacuo. 3-(4-tert-Butylphenyl)propionic acid is obtained, which is employed in the next stage without further purification.

d) 3-(4-tert-Butylphenyl)propionyl chloride: The acid chloride is prepared as described in Example 6c) and employed in the next stage without further purification.

e) 6-tert-Butylindan-1-one: 6-tert-Butylindan-1-one is prepared from the acid chloride 7d as described in 6c). The 6-tert-butylindan-1-one has a melting point of 94–96° C.

f) 2-Bromo-6-tert-butylindan-1-one: According to the process as is described in 6d), 6-tert-butylindanon-1-one is converted into 2-bromo-6-tert-butylindan-1-one; it has a melting point of 58–61° C.

g) 5-tert-Butyl-3-methyl-2-methylimino-2,3,8,8a-tetrahydroindeno-[1,2-d]thiazol-3a-ol hydrobromide: The reaction of 267 mg of 2-bromo-6-tert-butylindan-1-one with 156 mg of N,N'-dimethylthiourea in 10 ml of acetone yields the hydrobromide of 5-tert-butyl-3-methyl-2-methylimino-2,3,8,8a-tetrahydroindeno[1,2-d]thiazol-3a-ol of melting point 277–279° C.

EXAMPLE 8 (COMPOUND A23)

3a-Hydroxy-3-methyl-2-methylimino-3,3a,8,8a-tetrahydro-2H-indeno-[1,2-d]thiazole-6-carbonitrile hydrobromide a) 1-Oxoindan-5-carbonitrile: 9.5 g of 5-bromoindan-1-one and 4.93 g of CuCN are suspended in 10 ml of dimethylformamide and refluxed for 4 hours. A solution of 18 g of iron(III) chloride in 5 ml of conc. hydrochloric acid is added dropwise with 30 ml of water with stirring to the cooled, dark brown, viscous suspension and it is then stirred at 70° C. for 30 minutes. The reaction mixture is extracted three times by shaking with 50 ml of toluene, and the combined organic phases are extracted by shaking with 50 ml of 2N hydrochloric acid and 50 ml of 2N sodium hydroxide solution and then washed with water until neutral. The toluene extract is dried over magnesium sulfate and concentrated in vacuo, and the residue is recrystallized from n-heptane. 1-Oxoindan-5-carbonitrile of melting point 123–125° C. is obtained.

b) 2-Bromo-1-oxoindan-5-carbonitrile: The bromination of 1-oxoindan-5-carbonitrile is carried out as is described in Example 6d) and yields 2-bromo-1-oxoindan-5-carbonitrile of melting point 115–118° C.

c) 3a-Hydroxy-3-methyl-2-methylimino-3,3a,8,8a-tetrahydro-2H-indeno[1,2-d]thiazole-6-carbonitrile hydrobromide: 236 mg of 2-bromo-1-oxoindan-5-carbonitrile are dissolved in 10 ml of acetone and treated at 0–5° C. with 210 mg of N,N'-dimethylthiourea. The mixture is stirred at room temperature for 3 hours and at 0° C. for 1 hour. The reaction product is filtered off with suction, washed with acetone and dried in vacuo. The hydrobromide of 3a-hydroxy-3-methyl-2-methylimino-3,3a,8,8a-tetrahydro-2H-indeno[1,2-d]thiazole-6-carbonitrile of melting point 282–284° C. (decomposition) is obtained.

The compound A12 was prepared analogously, starting from 6-bromoindan-1-one.

EXAMPLE 9 (COMPOUND A18)

3-Methyl-2-methylimino-5-methylsulfonyl-6-phenylthio-2,3,8,8a-tetrahydro-indeno[1,2-d]thiazol-3a-ol a) 6-Methylsulfonyl-5-phenylthio-1-indanone: 2.55 ml of thiophenol are added dropwise under an argon atmosphere and with stirring to a suspension prepared from 4.9 g of 5-chloro-6-methylsulfonyl-1-indanone, 1.4 g of anhydrous ground potassium carbonate and 50 ml of DMF and the mixture is heated at 80° C. for about 10 hours while maintaining the stirring. After addition of 500 ml of water at room temperature, the crystals are filtered off and purified by dissolution in acetone, treatment with activated carbon and subsequent precipitation with water. Pale yellow crystalline substance, melting point 211–212° C.

b) 2-Bromo-6-methylsulfonyl-5-phenylthio-1-indanone is obtained by dropwise addition of a mixture of 0.39 ml of bromine in 10 ml of glacial acetic acid to a stirred solution of 2.4 g of 6-methylsulfonyl-5-phenylthio-1-indanone, 0.2 ml of a concentrated aqueous hydrobromic acid and 30 ml of glacial acetic acid, followed by pouring of the reaction mixture into a suspension of water and ice and subsequent filtration of the crystalline product. Slightly yellow crystalline substance, melting point 158–160° C.

c) 3-Methyl-2-methylimino-5-methylsulfonyl-6-phenylthio-2,3,8,8a-tetra-hydroindeno[1,2-d]thiazol-3a-ol hydrobromide 0.72 g of N,N'-dimethylthiourea is added to a solution of 2.7 g of 2-bromo-6-methylsulfonyl-5-phenylthio-1-indanone in 30 ml of acetone, the mixture is stirred at room temperature for one hour, and the crystalline compound of melting point 268–270° C. with decomposition is filtered.

d) 3-Methyl-2-methylimino-5-methylsulfonyl-6-phenylthio-2,3,8,8a-tetrahydroindeno[1,2-d]thiazol-3a-ol 3-Methyl-2-methylimino-5-methylsulfonyl-6-phenylthio-2,3,8,8a-tetra-hydroindeno[1,2-d]thiazol-3a-ol hydrobromide is suspended in methanol and treated with a 3-fold molar excess of triethylamine. The resulting solution is filtered and crystallized by trituration with a glass rod. Colorless crystalline compound, melting point with decomposition 142–143° C.

EXAMPLE 10 (COMPOUND A48)

8-Chloro-5a-hydroxy-3,4-dihydro-7-methylsulfonyl-indano[2,1-b]imidazo[1,2-d]thiazolidine hydrobromide a) 5-Chloro-6-nitro-1-indanone: 86 g of 5-chloro-1-indanone are introduced with stirring and external cooling into 540 ml of fuming nitric acid having a density of 1.52 g/ml such that the internal temperature is maintained between −15 and −10° C. The reaction mixture is poured into a stirred water/ice suspension and the crystalline yellow substance is filtered off. Purification by dissolution in a mixture of 2 parts of acetone and 5 parts of ethanol, treatment with activated carbon and extensive removal of the acetone content by distillation under reduced pressure. Melting point 126–128° C.

b) 6-Amino-5-chloro-1-indanone: A solution of 77.5 g of sodium hydrogensulfite in 250 ml of water is added dropwise to a boiling suspension of 30 g of 5-chloro-6-nitro-1-indanone in 400 ml of water in the course of one hour while maintaining the boiling and the mixture is refluxed for a further 2 hours. It is carefully adjusted to pH 1–2 using concentrated hydrochloric acid and heated to boiling for a further hour. After cooling, the crystals are filtered off, washed with water and recrystallized from isopropanol. Colorless to brownish crystalline substance, melting point 210–212° C. with decomposition.

c) 5-Chloro-6-chlorosulfonyl-1-indanone: A solution of 10.4 g of sodium nitrite in 30 ml of water is added dropwise to a suspension of 26.8 g of 6-amino-5-chloro-1-indanone in 200 ml of 20% strength hydrochloric acid with good stirring and cooling, the temperature being kept between 0 and 5° C. In the course of this, a solution is obtained which, after further stirring at 0° C., is added in portions with stirring to a solution of 12.7 g of copper(II) chloride dihydrate, 50 ml of water and 400 ml of sulfur dioxide-saturated glacial acetic acid at 0–5° C. The mixture is stirred for a further hour without external cooling, then 600 ml of water are added and the crystals are filtered off, washed with cold water a number of times on the filter and then dried in vacuo. Colorless crystalline substance; melting point 147–148° C.

d) 5-Chloro-1-indanone-6-sulfinic acid: 13.3 g of 5-chloro-6-chlorosulfonyl-1-indanone are introduced in portions with stirring into a solution of 26 g of sodium hydrogen- sulfite and 3 g of NaOH in 75 ml of water, 2 N sodium hydroxide solution simultaneously being added dropwise from a dropping funnel such that the pH is kept between 7 and 7.5. The mixture is then adjusted to pH 1–2 using concentrated hydrochloric acid, cooled to 0 to −5° C., and the crystals are filtered off and washed with water. Melting point >300° C. with blackening from 170° C.

e) 5-Chloro-6-methylsulfonyl-1-indanone: First 9.2 g of 5-chloro-1-indanone-6-sulfinic acid and then 15 g of methyl iodide are added to a sodium methoxide solution which has been prepared from 150 ml of methanol and 1 g of sodium and the mixture is heated to boiling for 10 hours under the attached high-efficiency condenser. After removing the solvent by distillation, the residue is treated with 200 ml of water, the crystals are filtered off and the product is carefully washed with water. Colorless crystalline substance from methanol after treatment with activated carbon, melting point 197–198° C.

f) 2-Bromo-5-chloro-6-methylsulfonyl-1-indanone: is obtained from 6.8 g of 5-chloro-6-methylsulfonyl-1-indanone and 1.45 g of bromine in glacial acetic acid. Colorless to slightly brownish crystalline substance, melting point 144° C.

g) 8-Chloro-5a-hydroxy-3,4-dihydro-7-methylsulfonyl-indano[2,1-b]-imidazo[1,2-d]thiazolidine hydrobromide A warm solution of 1.02 g of 2-imidazolidinethione in 7.5 ml of dimethylacetamide is added with stirring to a solution of 3.24 g of 2-bromo-5-chloro-6-methylsulfonyl-1-indanone in 50 ml of acetone and the mixture is stirred at room temperature for a further two hours. The colorless crystalline compound is filtered off and washed a number of times with acetone. Decomposition point 135° C.

h) 8-Chloro-5a-hydroxy-3,4-dihydro-7-methylsulfonylindano[2,1-b]-imidazo[1,2-d]thiazolidine is obtained analogously to the procedure indicated in Example 9 from 8-chloro-5a-hydroxy-3,4-dihydro-7-methylsulfonylindano[2, 1-b]imidazo[1,2-d]thiazolidine hydrobromide and triethylamine in methanol. Colorless crystalline substance, decomposition point 192° C.

EXAMPLE 11 (COMPOUND A27)

6-(4-Chlorophenoxy)-3-methyl-2-methylimino-2,3,8,8a-tetrahydroindeno[1,2-d]thiazol-3a-ol hydrochloride a) 5-(4-Chlorophenoxy)-1-indanone: After dissolution in 60 ml of anhydrous dimethylacetamide, 2.82 g of 4-chlorophenol are stirred at room temperature for ½ hour with 8.2 g of anhydrous and ground potassium carbonate. After addition of 1.5 g of 5-fluoroindanone, the mixture is stirred at 120–130° C. for 10 hours and the solvent is removed by distillation under reduced pressure after cooling. The residue is treated with water and extracted a number of times with ethyl acetate. The organic phase is washed with 2 N NaOH and subsequently with water, then stirred for 15 minutes after addition of activated carbon and the solvent is removed by distillation under reduced pressure after drying over anhydrous magnesium sulfate. The partially crystalline dark residue is purified by column chromatography on silica gel using an eluent consisting of equal parts of ethyl acetate and toluene. Brown crystals, melting point 75–80° C.

b) 2-Bromo-5-(4-chlorophenoxy)-1-indanone: Approximately ½ ml of a solution of 0.25 ml of bromine in 5 ml [lacuna] is added dropwise to a solution of 1.3 g of 5-(4-chlorophenoxy)-1-indanone in 30 ml [lacuna] and the mixture is heated slowly until the bromine is decolorized or until evolution of HBr begins. It is then cooled and the remaining amount of bromine is added dropwise at room temperature, the mixture is stirred for a further 2 hours and the solvent is removed by distillation under reduced pressure. The residual dark oil is used without further purification.

c) 6-(4-Chlorophenoxy)-3-methyl-2-methylimino-2,3,8,8a-tetrahydro-indeno[1,2-d]thiazol-3a-ol hydrobromide is obtained by reaction of 1.69 g of 2-bromo-5-(4-chlorophenoxy)-1-indanone and 0.52 g of N,N'-dimethylthiourea in 25 ml of ethyl acetate as a pale yellow to colorless crystalline precipitate. Melting point 252–255° C.

d) 6-(4-Chlorophenoxy)-3-methyl-2-methylimino-2,3,8,8a-tetrahydro-indeno[1,2-d]thiazol-3a-ol is formed by treatment of a solution of 1.5 g of 6-(4-chlorophenoxy)-3-methyl-2-methylimino-2,3,8,8a-tetrahydroindeno[1,2-d]thiazol-3a-ol hydrobromide in 40 ml of methanol with 2.3 ml of triethylamine. The solvent is removed by distillation and the residue is solidified under water. Amorphous solid, melting point 85–90° C.

e) 6-(4-Chlorophenoxy)-3-methyl-2-methylimino-2,3,8,8a-tetrahydro-indeno[1,2-d]thiazol-3a-ol hydrochloride is obtained as a crystalline colorless precipitate by addition of a solution of HCl gas in diethyl ether to a solution of 1.2 g of 6-(4-chlorophenoxy)-3-methyl-2-methylimino-2,3,8,8a-tetrahydroindeno[1,2-d]thiazol-3a-ole in 30 ml of ethyl acetate until there is a strongly acidic reaction. Melting point 247–250° C.

EXAMPLE 12 (COMPOUND A 28)

6-(2,2,2-Trifluoroethoxy)-3-methyl-2-methylimino-2,3,8,8a-tetrahydro-indeno[1,2-d]thiazol-3a-ole hydrobromide a) 5-(2,2,2-Trifluoroethoxy)-1-indanone: 2.2 ml of 2,2,2-trifluoroethanol are added to a stirring mixture of 3.5 g of 5-fluoroindanone, 20 ml of anhydrous dimethylformamide and 4.1 g of anhydrous and ground potassium carbonate and the mixture is stirred at 80° C. for 10 hours. The solvent is removed by distillation under reduced pressure, the residue is dissolved in ethyl acetate and the organic phase is washed a number of times with water. The indanone derivative is obtained as a brownish crystalline solid after chromatography on silica gel using a mixture of equal parts of ethyl acetate and toluene as an eluent. Melting point 93–97° C.

b) 2-Bromo-5-(2,2,2-trifluoroethoxy)-1-indanone: is obtained by reaction of 0.9 g of 5-(2,2,2-trifluoroethoxy)-1-indanone with 0.2 ml of bromine in 25 ml of ethyl acetate. The compound is used further without further purification.

c) 6-(2,2,2-Trifluoroethoxy)-3-methyl-2-methylimino-2,3,8,8a-tetra-hydroindeno[1,2-d]thiazol-3a-ole hydrobromide is obtained by reaction of 1.2 g of 2-bromo-5-(2,2,2-trifluoroethoxy)-1-indanone and 0.4 g of N,N'-dimethylthiourea in 25 ml of ethyl acetate as a pale yellow to colorless crystalline precipitate. Melting point 278–280° C.

d) 6-(2,2,2-Trifluoroethoxy)-3-methyl-2-methylimino-2,3,8,8a-tetra-hydroindeno[1,2-d]thiazol-3a-ole is obtained from 6-(2,2,2-trifluoroethoxy)-3-methyl-2-methylimino-2,3,8,8a-tetrahydroindeno[1,2-d]thiazol-3a-ole hydrobromide and triethylamine. Colorless crystalline solid, melting point 138–140° C.

e) 6-(2,2,2-Trifluoroethoxy)-3-methyl-2-methylimino-2,3,8,8a-tetra-hydroindeno[1,2-d]thiazol-3a-ole hydrochloride is obtained from 6-(2,2,2-trifluoroethoxy)-3-methyl-2-methylimino-2,3,8,8a-tetrahydroindeno[1,2-d]thiazol-3a-ole and a solution of HCl gas in ether. Colorless crystals, melting point 274–276° C.

EXAMPLE 13 (COMPOUND A45)

5-(2,2,3,3,4,4,4-Heptafluorobutoxy)-3-methyl-2-methylimino-2,3,8,8a-tetra-hydroindeno[1,2-d]thiazol-3a-ole hydrochloride a) 5-(2,2,3,3,4,4,4-Heptafluorobutoxy)-1-indanone: is obtained from 6.5 g of 5-fluoroindanone and 35.6 g of anhydrous and ground potassium carbonate in 50 ml of anhydrous dimethylacetamide as a honey-colored oil.

b) 2-Bromo-5-(2,2,3,3,4,4,4-heptafluorobutoxy)-1-indanone: is obtained by reaction of 4.16 g of 5-(2,2,3,3,4,4,4-heptafluorobutoxy)-1-indanone with 0.69 ml of bromine in 110 ml of ethyl acetate. The compound is isolated as a brown oil and is used without further purification.

c) 6-(2,2,3,3,4,4,4-Heptafluorobutoxy)-3-methyl-2-methylimino-2,3,8,8a-tetrahydroindeno[1,2-d]thiazol-3a-ole hydrobromide is obtained by reaction of 1.4 g of 2-bromo-5-(2,2,3,3,4,4,4-heptafluorobutoxy)-1-indanone and 0.36 g of N,N'-dimethylthiourea in 40 ml of ethyl acetate as a pale yellow to colorless crystalline precipitate. Decomposition point 253° C.

d) 6-(2,2,3,3,4,4,4-Heptafluorobutoxy)-3-methyl-2-methylimino-2,3,8,8a-tetrahydroindeno[1,2-d]thiazol-3a-ole is obtained from 6-(2,2,3,3,4,4,4-heptafluorobutoxy)-3-methyl-2-methylimino-2,3,8,8a-tetrahydroindeno[1,2-d]thiazol-3a-ole hydrobromide and triethylamine. Colorless crystalline solid, melting point 138–140° C.

e) 6-(2,2,3,3,4,4,4-Heptafluorobutoxy)-3-methyl-2-methylimino-2,3,8,8a-tetrahydroindeno[1,2-d]thiazol-3a-ole hydrochloride is obtained from 6-(2,2,3,3,4,4,4-heptafluorobutoxy)-3-methyl-2-methylimino-2,3,8,8a-tetrahydroindeno[1,2-d]thiazol-3a-ole and ethereal hydrochloric acid. Colorless crystals, melting point 248–250° C.

EXAMPLE 14 (COMPOUND B1)

6-Chloro-8a-fluoro-3-methyl-2-methylimino-2,3,8,8a-tetrahydroindeno-[1,2-d]thiazol-3a-ole:

a) 5-Chloro-2-fluoroindan-1-one: 25 ml of a 1.6 molar solution of n-butyllithium in n-hexane are slowly added dropwise at a temperature of <–50° C. to a solution of 5.24 ml of diisopropylamine in 60 ml of dry tetrahydrofuran; the mixture is then stirred at –50° C. for a further 10 minutes. A solution of 6.33 g of 5-chloroindan-1-one in 60 ml in dry tetrahydrofuran is then slowly added and the mixture is stirred at –50° C. for a further 20 minutes. Finally, 11.4 g of N-fluorodibenzenesulfimide, dissolved in 60 ml of dry tetrahydrofuran, are added dropwise. The mixture is allowed to warm to 0° C. in the course of 2 hours with stirring, 120 ml of a satd. sodium hydrogencarbonate solution are added dropwise, the tetrahydrofuran is removed by distillation in vacuo and the residue is extracted twice by shaking with 150 ml of ethyl acetate. The organic phase is washed with water and satd. sodium chloride solution, dried over magnesium sulfate and concentrated, and the residue is purified by chromatography on silica gel using diisopropyl ether/n-heptane 1/1. In addition to 5-chloro-2,2-difluoroindan-1-one, 5-chloro-2-fluoroindan-1-one of melting point 102–104° C. is obtained.

b) 5-Chloro-2-bromo-2-fluoroindan-1-one: The bromination of 5-chloro-2-fluoroindan-1-one is carried out in an analogous manner to that described in 6d) and yields 5-chloro-2-bromo-2-fluoroindan-1-one of melting point 104–105° C.

c) 6-Chloro-8a-fluoro-3-methyl-2-methylimino-2,3,8,8a-tetrahydro-indeno[1,2-d]thiazol-3a-ole: 263 mg of 5-chloro-2-bromo-2-fluoroindan-1-one and 156 mg of N,N'-dimethylthiourea are dissolved in 5 ml of acetone and the solution is stirred, first at room temperature for 90 minutes and then at 50° C. for 2 hours. The reaction mixture is cooled and concentrated in vacuo. 5 ml of toluene are added to the residue and the mixture is heated under reflux for 2 hours, cooled, treated with 152 mg of triethylamine and stirred at room temperature for 2 hours. The residue is filtered off with suction, washed with a little water and dried in vacuo. 6-Chloro-8a-fluoro-3-methyl-2-methylimino-2,3,8,8a-tetrahydroindeno[1,2-d]thiazol-3a-ole of melting point 189–190° C. is obtained.

EXAMPLE 15 (COMPOUND B2)

6-Chloro-8a-fluoro-3-methyl-2-methylimino-2,3,8,8a-tetrahydroindeno-[1,2-d]thiazol-3a-ole hydrochloride: 1 g (4.47 mmol) of 6-chloro-8a-fluoro-3-methyl-2-methylimino-2,3,8,8a-tetrahydroindeno[1,2-d]thiazol-3a-ole is dissolved in 120 ml of warm isopropanol and treated with 1.2 g of about 20% strength ethereal HCl solution. After 1 h at room temperature, the reaction mixture is concentrated, and the residue is stirred with acetone, filtered off with suction and dried in vacuo. The hydrochloride of 6-chloro-8a-fluoro-3-methyl-2-methylimino-2,3,8,8a-tetrahydro-indeno[1,2-d]thiazol-3a-ole of melting point 205° C. (dec.) is obtained.

EXAMPLE 16 (COMPOUNDS B1(–) and B1(+))

100 mg of the racemate of the compound B1 are resolved into the enantiomers by means of an HPLC column (CSP Chiralpak AD 250×4.6) using n-hexane/ethanol 10+1. The (–)-rotatory enantiomer B1(–) having a retention time of 7.9 minutes of melting point 175–79° C. (dec.) and the (+)-rotatory enantiomer B1(+) having a retention time of 8.84 minutes of melting point 172–77° C. (dec.) are obtained.

EXAMPLE 17 (COMPOUNDS C1 and C6)

(6-Chloro-3a-methoxy-3-methyl-3,3a,8,8a-tetrahydroindeno[1,2-d]thiazol-2-ylidene)methylamine (hydrochloride):

5 g of the hydrochloride of 6-chloro-3-methyl-2-methylimino-2,3,8,8a-tetrahydroindeno[1,2-d]thiazol-3a-ole are dissolved in 200 ml of methanol and the solution is heated under reflux for three days. The cooled reaction mixture is concentrated in vacuo, and the residue is stirred with 50 ml of acetone and filtered. The filtrate is concentrated, the residue is suspended in 100 ml of ethyl acetate and the suspension is treated with 100 ml of a satd. sodium hydrogencarbonate solution. The organic phase is separated off, washed with water, dried over magnesium sulfate, concentrated and chromatographed on silica gel using ethyl acetate/methanol 9/1. 6-Chloro-3-methyl-2-methylimino-2,3,8,8a-tetrahydroindeno[1,2-d]thiazol-3a-ole of melting point 94–96° C. is obtained.

The hydrochloride of this compound (compound C6) is obtained by dissolving the free base in methyl tert-butyl ether and adding ethereal hydrochloric acid with stirring and cooling with an ice bath until a pH of about 1 is obtained. The reaction mixture is then stirred at room temperature for a further 3 hours, the solvent is removed by distillation, and the residue is treated with acetone and filtered. The filtrate is concentrated in vacuo and the residue is dried in vacuo. The hydrochloride of 6-chloro-3-methyl-2-methylimino-2,3,8,8a-tetrahydroindeno[1,2-d]thiazol-3a-ole of melting point 65–70 ° C. is obtained.

The compounds C2–C5 were prepared analogously.

EXAMPLES 18 a and b (COMPOUND C1(+) and C1(−))

100 mg of the racemate of the compound C1 (free base) are resolved into the enantiomers by means of an HPLC column (CSP Chiralpak AD 250×4.6) using n-hexane/2-propanol 25/1 with 0.1% diethylamine. The (+)-rotatory enantiomer C1(+) having a retention time of 7.38 minutes and a specific rotation of 237.5° (c=10.3 mg/2 ml in trichloromethane) of melting point 70–71° C. and the (−)-rotatory enantiomer C1(−) having a retention time of 8.06 minutes and a specific rotation of −229.1° (c=9.9 mg/2 ml in trichlormethane) of melting point 71–72° C. is obtained.

EXAMPLE 19 (COMPOUND D2)

8-(2-Chlorophenyl)-3-methyl-2-methylimino-2,3,8,8a-tetrahydroindeno-[1,2-d]thiazol-3a-ole hydrobromide a) 2,3-Dibromo-3-(2-chlorophenyl)propionic acid is obtained by dropwise addition of a solution of 7.8 g of bromine to a suspension of 9 g of 2-chlorocinnamic acid in 250 ml of chloroform with irradiation with a 500 W daylight lamp and subsequent evaporation of the solvent. Melting point 183–185° C.

b) 2,3-Dibromo-3-(2-chlorophenyl)propionyl chloride is obtained as an oily amorphous residue by boiling 10 g of 2,3-dibromo-3-(2-chlorophenyl)propionic acid in 70 ml of thionyl chloride under reflux conditions and removing the liquid by distillation.

c) 2-Bromo-3-(2-chlorophenyl)-1-indanone 6.6 g of anhydrous active aluminum chloride are introduced into a mixture of 4.1 g of anhydrous benzene and 30 ml of carbon disulfide under an argon atmosphere and the mixture is then cooled to −20° C. While maintaining the cooling, a solution of 15 g of 2,3-dibromo-3-(2-chlorophenyl)propionyl chloride in 50 ml of carbon disulfide is added dropwise to this suspension, and the mixture is then kept at 0° C. for 5 hours and allowed to stand at a temperature of 4–8° C. in a refrigerator for a further 16 hours. The reaction mixture is poured with stirring into an ice-water mixture which has been rendered strongly acidic with conc. HCl and is extracted with chloroform, and the organic phase is washed with water and then dried over magnesium sulfate. After removing the solvent by distillation, the viscous amorphous residue is taken up with diethyl ether, the mixture is stirred with a sodium bicarbonate alkaline aqueous solution for a number of hours and the organic solvent is removed by distillation after drying over magnesium sulfate. Viscous amorphous substance.

d) 8-(2-Chlorophenyl)-3-methyl-2-methylimino-2,3,8,8a-tetrahydroindeno[1,2-d]thiazol-3a-ole hydrobromide 4 g of 2-bromo-3-(2-chlorophenyl)-1-indanone are treated with 1.2 g of N,N'-dimethylthiourea in ethyl acetate and the mixture is stirred at room temperature for 2 days. Pale yellow crystalline substance, melting point 163° C.

EXAMPLE 20 (COMPOUND D14)

3a-Hydroxy-3-methyl-2-methylimino-8-phenyl-3a,8,9,9a-tetrahydronaphtho[2, 1-b]thiazolidine hydrobromide a) 2-Bromo4-phenyl-1-tetralone is obtained by reaction of 4.43 g of 4-phenyl-1-tetralone and 3.2 g of bromine in HBr-containing ethyl acetate as a viscous amorphous product.

b) 3a-Hydroxy-3-methyl-2-methylimino-8-phenyl-3a,8,9,9a-tetrahydro-naphtho[2,1-b]thiazolidine hydrobromide is obtained by reaction of 26 g of 2-bromo-4-phenyl-1-tetralone and 5 g of N,N'-dimethylthiourea in 60 ml of ethyl acetate as a pale yellow to colorless crystalline precipitate. Melting point 229–231° C. (with decomposition).

The compound D1 was prepared analogously.

EXAMPLE 21 (COMPOUND D16)

1-Ethyl-2-ethylimino-9-nitro-1,2,4,5-tetrahydro-3aH-6-oxa-3-thia-1-aza-benzo[e]azulen-10b-ol a) 4-Phenoxybutyryl chloride: 504.6 g of 4-phenoxybutyric acid are refluxed for 3 hours with 308 ml of thionyl chloride and 1.8 ml of dimethylformamide. The mixture is then distilled in vacuo and 4-phenoxybutyryl chloride of boiling point 145–147° C. is obtained at a pressure of 10–12 mm Hg.

b) 6,7,8,9-Tetrahydrobenzocyclohepten-5-one: 192 g of aluminum(III) chloride are suspended in 1.6 l of dry 1,2-dichloroethane and a solution of 238 g of 4-phenoxyburyryl chloride in 300 ml of 1,2-dichloroethane is slowly added dropwise with stirring at a temperature of −5° C. under an argon protective gas atmosphere in the course of 5.5 hours. The reaction product is subjected to hydrolysis by pouring it into a mixture of 2 l of water with 2 l of conc. hydrochloric acid. The mixture is stirred for 30 minutes, and the precipitate is allowed to settle and is filtered off with suction. The organic phase is separated off and the aqueous phase is extracted three times by shaking with 1,2-dichloroethane. The organic extracts are washed with water, with dil. hydrogencarbonate solution and finally with satd. sodium chloride solution, dried over sodium sulfate and concentrated in vacuo. The residue is distilled in vacuo. 6,7,8,9-tetrahydrobenzocyclohepten-5-one having a melting point of 79–84° C. at a pressure of 0.001 mm Hg is obtained as a clear liquid.

c) 7-Nitro-3,4-dihydro-2H-benzo[b]oxepin-5-one: 25 g of 6,7,8,9-tetrahydrobenzocyclohepten-5-one are dissolved in 280 ml of conc. sulfuric acid at −10° C. With vigorous stirring, a total of 16.75 g of sodium nitrate are introduced little by little at −10° C. The dark reaction mixture is stirred at 0° C. for 45 minutes; in the course of this the residual sodium nitrate slowly goes into solution. The reaction mixture is then added to ice water with stirring and stirred for 30 minutes. The precipitate is filtered off with suction and washed with water until neutral. The air-dry residue is recrystallized from isopropanol for purification. 7-Nitro-3,4-dihydro-2H-benzo[b]oxepin-5-one is obtained, which is immediately processed further.

d) 4-Bromo-7-nitro-3,4-dihydro-2H-benzo[b]oxepin-5-one: 2.07 g of 7-nitro-3,4-dihydro-2H-benzo[b]oxepin-5-one are dissolved in 10 ml of dichloromethane and, while cooling with an ice bath, treated with stirring with 1.7 g of bromine, dissolved in 10 ml of dichloromethane (addition over 3 hours). The reaction mixture is introduced into 30 ml of a saturated sodium hydrogencarbonate solution, the organic phase is separated off and the aqueous phase is extracted a number of times with dichloromethane. The combined organic extracts are washed with satd. sodium chloride solution, dried over sodium sulfate and concentrated, and the residue is recrystallized from butyl acetate and yields 4-bromo-7-nitro-3,4-dihydro-2H-benzo[b]oxepin-5-one of melting point 115–118° C.

e) 1-Ethyl-2-ethylimino-9-nitro-1,2,4,5-tetrahydro-3aH-6-oxa-3-thia-1-azabenzo[e]azulen-10b-ol: 5 g of 4-bromo-7-nitro-3,4-dihydro-2H-benzo[b]oxepin-5-one are heated to reflux for 30 minutes with 2.4 g of N,N'-diethylthiourea in 30 ml of butan-2-one. The precipitate is filtered off with suction, stirred with satd. potassium hydrogencarbonate solution and extracted with ethyl acetate. The organic phase is washed with satd. sodium chloride solution, dried over sodium sulfate and concentrated, and the residue is recrystallized from methanol/water. 1-Ethyl-2-ethylimino-9-nitro-1,2,4,5-tetrahydro-3aH-6-oxa-3-thia-1-azabenzo[e]azulen-10b-ol of melting point 125–127° C. is obtained.

The compounds D12, D15, D17–D20, D22-D23, D26–D31 were prepared analogously, starting from the corresponding benzocyclohexanone or benzocycloheptanone derivatives.

EXAMPLE 22 (COMPOUND D21)

1-Methyl-2-methylimino-6,6-dioxo-1,2,3a,4,5,6-hexahydrodithia-1-aza-benzo[e]azulen-10b-ol a) 4-Phenylsulfanylbutyryl chloride: 54.9 g of 4-phenylsulfanylbutyric acid are dissolved in 280 ml of toluene using 0.5 ml of dimethylformamide. 36.5 ml of oxalyl chloride are added dropwise and the reaction mixture is stirred at room temperature for 2 hours and at 65–70° C. for a further hour. Toluene and excess oxalyl chloride are then removed by distillation in vacuo. The brown, oily residue is distilled in a high vacuum and yields 4-phenylsulfanylbutyryl chloride having a boiling point of 116–119° C. at a pressure of 0.008 mm Hg.

b) 3,4-Dihydro-2H-benzo[b]thiepin-5-one: 38.2 g of anhydrous aluminum(III) chloride are suspended in 260 ml of dichlormethane. A solution of 51.1 g of 4-phenylsulfanylbutyryl chloride in 70 ml of dichloromethane is slowly added with stirring at 0° C. (2 h). The reaction mixture is stirred overnight, and a brown-yellow solution is obtained. This solution is added with vigorous stirring to an ice-cold mixture of 1 l of water with 1 l of conc. hydrochloric acid. After it has been stirred for 30 minutes, the mixture is extracted three times with 200 ml of diethyl ether in each case. The combined organic phases are extracted by shaking with water and satd. sodium chloride solution, dried over sodium sulfate and concentrated in vacuo. The oil obtained is distilled and 3,4-dihydro-2 H-benzo[b]thiepin-5-one having a boiling point of 93–94° C. at a pressure of 0.002 mm Hg is obtained.

c) 1,1-Dioxo-1,2,3,4-tetrahydrobenzo[b]thiepin-5-one: 10 g of 3,4dihydro-2H-benzo[b]thiepin-5-one are dissolved in 125 ml of glacial acetic acid. 11.2 ml of 35% strength hydrogen peroxide are slowly added dropwise at room temperature with stirring. After stirring at room temperature for 2 hours, a further 11 ml of 35% strength hydrogen peroxide are added dropwise. The reaction mixture is then stirred overnight. The solvent is carefully removed in vacuo, and the residue is treated with ice and carefully treated with 1 N potassium hydrogencarbonate solution with stirring. The aqueous suspension is saturated with sodium chloride, and the precipitate is filtered off with suction, washed with water and dried in vacuo. 1,1-Dioxo-1,2,3,4-tetrahydrobenzo[b]thiepin-5-one of melting point 142–146° C. is obtained.

d) 4-Bromo-1,1-dioxo-1,2,3,4-tetrahydrobenzo[b]thiepin-5-one: 9.45 g of 1,1-dioxo-1,2,3,4-tetrahydrobenzo[b]thiepin-5-one are dissolved in 200 ml of glacial acetic acid with stirring. 8.9 g of N-bromosuccinimide are added and the mixture is heated at 75–80° C. for 8 hours. After completion of the reaction, the solvent is removed by evaporation in vacuo, and the oily residue is treated with ice-cold sodium hydrogencarbonate solution with stirring. After stirring for 30 minutes, the residue is filtered off with suction and washed with water. After drying in vacuo, 4-bromo-1,1-dioxo-1,2,3,4-tetrahydro-benzo[b]thiepin-5-one having a melting point of 132–136° C. is obtained.

e) 1-Methyl-2-methylimino-6,6-dioxo-1,2,3a,4,5,6-hexahydro-dithia-1-azabenzo[e]azulen-10b-ol: 4.34 g of 4-bromo-1,1-dioxo-1,2,3,4-tetrahydro-benzo[b]thiepin-5-one are suspended in 15 ml of butan-2-one. The mixture is heated to 60–70° C. and 1.8 g of N,N'-dimethylthiourea are added in portions. The solution is refluxed for 2 hours, then cooled and the precipitate is filtered off with suction and washed with butan-2-one. The residue is stirred with 100 ml of satd. sodium hydrogencarbonate solution and extracted with ethyl acetate. The combined organic phases are washed with satd. sodium chloride solution, dried over sodium sulfate and concentrated in vacuo. The residue is taken up with a little ethyl acetate, filtered off with suction and dried in vacuo. 1-Methyl-2-methylimino-6,6-dioxo-1,2,3a,4,5,6-hexahydrodithia-1-azabenzo[e]azulen-10b-ol of melting point 142–144° C. (decomposition) is obtained.

EXAMPLE 23 (COMPOUND D25)

N-(10b-Hydroxy-1-methyl-2-methylimino-1,2,3a,4,5,10b-hexahydro-6-oxa-3-thia-1-azabenzo[e]azulen-9-yl) acetamide hydrochloride a) N-(5-Oxo-2,3,4,5-tetrahydrobenzo[b]oxepin-7-yl)-acetamide: 16 g of 7-nitro-3,4-dihydro-2H-benzo[b]oxepin-5-one are dissolved in 400 ml of methanol, treated with 270 g of palladium on activated carbon (10% strength) and hydrogenated at normal pressure. After filtration and removal of the solvent in vacuo, the oxygen-sensitive 7-amino-3,4-dihydro-2H-benzo[b]oxepin-5-one is obtained as a yellow oil. This oil is dissolved in 150 ml of dichloromethane; 8 g of triethylamine are added and then, with ice-cooling, 8.1 g of acetic anhydride are slowly added dropwise with vigorous stirring. The reaction mixture is stirred at room temperature for a further hour. The solution is concentrated in vacuo and the residue is taken up with ethyl acetate, washed with water and with satd. sodium chloride solution, dried over sodium sulfate and concentrated again. After crystallization from butyl acetate, the N-(5-oxo-2,3,4,5-tetrahydrobenzo[b]oxepin-7-yl)-acetamide melts at 130–132° C.

b) N-(4-Bromo-5-oxo-2,3,4,5-tetrahydrobenzo[b]oxepin-7-yl)-acetamide: 1 g of N-(5-oxo-2,3,4,5-tetrahydrobenzo[b]oxepin-7-yl)acetamide is dissolved in 6 ml of dichlormethane. 0.8075 g of bromine, dissolved in 5 ml of dichloromethane, is slowly added dropwise at 0° C. with stirring. The reaction mixture is stirred overnight at room temperature, then poured onto an ice-cold satd. sodium hydrogencarbonate solution and extracted a number of times with dichloromethane. The organic phases are washed with water and with satd. sodium chloride solution, dried over sodium sulfate and concentrated in vacuo. The residue is recrystallized from isopropanol and yields N-(4-bromo-5-oxo-2,3,4,5-tetrahydrobenzo[b]oxepin-7-yl)-acetamide having a melting point of 157–160° C.

c) N-(10b-Hydroxy-1-methyl-2-methylimino-1,2,3a,4,5, 10b-hexahydro-6-oxa-3-thia-1-aza-benzo[e]azulen-9-yl)acetamide hydrochloride: 7 g of N-(4-bromo-5-oxo-2,3,4,5-tetrahydrobenzo[b]oxepin-7-yl)-acetamide and 2.5 g of N,N'-dimethylthiourea are refluxed for 4 hours in 60 ml of butan-2-one. The cooled suspension is filtered, and the residue is stirred with 200 ml of satd. potassium hydrogencarbonate solution. A little ethyl acetate is added, the residue is filtered off with suction and washed with water, and N-(10b-hydroxy-1-methyl-2-methylimino-1,2,3a,4,5, 10b-hexahydro-6-oxa-3-thia-1-azabenzo[e]azulen-9-yl)acetamide of melting point 186–188° C. is obtained. The free base is dissolved in 30 ml of 2 N hydrochloric acid. After stirring for about 10 minutes, the hydrochloride of N-(10b-hydroxy-1-methyl-2-methylimino-1,2,3a,4,5, 10b-hexahydro-6-oxa-3-thia-1-azabenzo[e]azulen-9-yl) acetamide precipitates. It melts with decomposition at 270° C.

EXAMPLE 24 (COMPOUND E2)
6-Chloro-3-(4-methoxyphenyl)-2-(4-methoxyphenylimino)-2,3,8,8a-tetra-hydroindeno[1,2-d]thiazol-3a-ole hydrobromide 1 g of 2-bromo-5-chloroindan-1-one and 1.17 g of 1,3-bis(4-methoxy-phenyl)thiourea are suspended in 50 ml of dry dichloromethane and stirred at room temperature for 4 hours and at ice-bath temperature for one hour. The precipitate is filtered off with suction, washed with dichloromethane and dried in vacuo. The hydrobromide of 6-chloro-3-(4-methoxyphenyl)-2-(4-methoxyphenylimino)-2,3,8,8a-tetrahydroindeno[1,2-d]thiazol-3a-ole is obtained, which melts at 230–235° C. with decomposition.

The compounds E1 and E3–E5 were prepared analogously.

German Application 19831878.2 filed Jul. 17, 1998, from which applicants' claim Section 119 priority, is incorporated herein by reference in its entirety.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A polycyclic thiazolidin-2-ylidene amine of the formula I

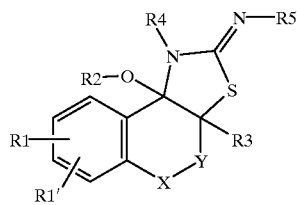

in which
A)
Y is a direct bond, —$CH_2$—, or —$CH_2$—$CH_2$—;
X is $CH_2$, $CH(CH_3)$, $CH(C_2H_5)$, or $CH(C_3H_7)$;
R1 is CN; COOH; COO($C_1$–$C_6$)-alkyl; $CONH_2$; CONH($C_1$–$C_6$)-alkyl; CON(($C_1$–$C_6$)-alkyl)$_2$; ($C_2$–$C_6$)-alkyl; ($C_2$–$C_6$)-alkenyl; ($C_2$–$C_6$)-alkyny; O—$CH_2$—$CF_3$; O—$CH_2$—$CF_2$—$CF_3$; O—($C_4$–$C_6$)-alkyl, where in the alkyl radicals one or more, or all hydrogen(s) may be replaced by fluorine, or one hydrogen may be replaced by OH, OC(O)$CH_3$, O—$CH_2$—Ph, $NH_2$ or N($COOCH_2Ph$)$_2$;
S—($C_1$–$C_6$)-alkyl; S—($CH_2$)$_n$-pheny; SO—($C_1$–$C_6$)-alky; SO—($CH_2$)$_n$-pheny; $SO_2$—($C_1$–$C_6$)-alkyl; $SO_2$—($CH_2$)$_n$-phenyl; where n may be =0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl, or $NH_2$;
$NH_2$; NH—($C_1$–$C_6$)-alkyl; N(($C_1$–$C_6$)-alkyl)$_2$; NH($C_{1-C7}$)-acyl; phenyl; biphenyl; O—($CH_2$)$_n$-phenyl, where n may be =0–6; 1- or 2-naphthyl; 2-, 3- or 4-pyridyl; 2- or 3-furanyl or 2- or 3-thienyl; where the phenyl, biphenyl, naphthyl, pyridyl, furanyl or thienyl rings in each case may be substituted one to 3 times by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl, or $CONH_2$;
1,2,3-triazol-5-yl, where the triazole ring may be substituted in the 1-, 2- or 3-position by methyl or benzyl;
tetrazol-5-yl, where the tetrazole ring may be substituted in the 1- or 2-position by methyl or benzyl;
R1' is H, F, Cl, Br, I, $CH_3$, $CF_3$, O—($C_1$–$C_3$)-alkyl, $NO_2$, $SO_2$—$NH_2$, $SO_2NH$($C_1$–$C_6$)-alkyl, $SO_2$N[($C_1$–$C_6$)-alkyl]$_2$ or R1;
R2 is H, ($C_1$–$C_6$)-alkyl, ($C_3$–$C_6$)-cycloalkyl, ($CH_2$)$_n$-phenyl, ($CH_2$)$_n$-thienyl, ($CH_2$)$_n$-pyridyl, ($CH_2$)$_n$-furyl, C(O)—($CH_2$)$_n$-phenyl, C(O)—($CH_2$)$_n$-thienyl, C(O)—($CH_2$)$_n$-pyridyl, or C(O)—($CH_2$)$_n$-furyl, where n may be =0–5 and in which phenyl, thienyl, pyridyl, furyl in each case may be substituted up to two times by Cl, F, CN, $CF_3$, ($C_1$–$C_3$)-alkyl, OH, O—($C_1$–$C_6$)-alkyl; C(O)—($C_1$–$C_6$)-alkyl, or C(O)—($C_3$–$C_6$)-cycloalkyl;
R3 is H, ($C_1$–$C_6$)-alkyl, F, CN, $N_3$, O—($C_1$–$C_6$)-alkyl, $CH_2$—COO($C_1$–$C_6$ alkyl), $CH_2$—COO($C_3$–$C_8$ cycloalkyl), $CH_2$—COOH, $CH_2$—$CONH_2$, $CH_2$—$CONHCH_3$, $CH_2$—CON($CH_3$)$_2$, ($CH_2$)$_n$-phenyl, ($CH_2$)$_n$-thienyl, ($CH_2$)$_n$-pyridyl, or ($CH_2$)$_n$-furyl, where n may be =0–5 and in which phenyl, thienyl, pyridyl, and furyl in each case may be substituted up to two times by Cl, F, CN, $CF_3$, ($C_1$–$C_3$)-alkyl, OH, O—($C_1$–$C_6$)-alkyl; ($C_2$–$C_6$)-alkynyl, ($C_2$–$C_6$)-alkenyl, C(O)$OCH_3$, C(O)$OCH_2CH_3$, C(O)OH, C(O)$NH_2$, C(O)$NHCH_3$, C(O)N($CH_3$)$_2$, or OC(O)$CH_3$;
R4 is ($C_1$–$C_6$)-alkyl, ($C_3$–$C_6$)-cycloalkyl, ($CH_2$)$_n$-phenyl, ($CH_2$)$_n$-thienyl, ($CH_2$)$_n$-pyridyl, or ($CH_2$)$_n$-furyl, where n may be =0–5 and in which phenyl, thienyl, pyridyl, and furyl in each case may be substituted up to two times by Cl, F, CN, $CF_3$, ($C_1$–$C_3$)-alkyl, OH, or O—($C_1$–$C_6$)-alkyl;
R5 is ($C_1$–$C_6$)-alkyl, ($C_3$–$C_6$)-cycloalkyl, ($CH_2$)$_n$-phenyl, ($CH_2$)$_n$-thienyl, ($CH_2$)$_n$-pyridyl, or ($CH_2$)$_n$-furyl, where n may be =0–5 and in which phenyl, thienyl, pyridyl, or furyl in each case may be substituted up to two times by Cl, F, CN, $CF_3$, ($C_1$–$C_3$)-alkyl, OH, or O—($C_1$–$C_6$)-alkyl;

or

R4 and R5 together form a —CH$_2$—CH$_2$—, —CH$_2$—C(CH$_3$)$_2$—, —CH$_2$—CH$_2$—CH$_2$—, or —CH$_2$—CH$_2$—CH$_2$—CH$_2$— group;

or

B)

Y is a direct bond, —CH$_2$— or —CH$_2$—CH$_2$—;

X is CH$_2$, CH(CH$_3$), CH(C$_2$H$_5$), or CH(C$_3$H$_7$);

R1 and R1' independently of one another are H; F; Cl; Br; I; NO$_2$; CN; COOH; COO(C$_1$–C$_6$)-alkyl; CONH$_2$; CONH(C$_1$–C$_6$)-alkyl; CON[(C$_1$–C$_6$)-alkyl]$_2$; (C$_1$–C$_6$)-alkyl; (C$_2$–C$_6$)-alkenyl; (C$_2$–C$_6$)-alkynyl; O—(C$_1$–C$_6$)-alkyl; O—CH$_2$—CF$_3$; O—CH$_2$—CF$_2$—CF$_3$, or O—(C$_4$–C$_6$)-alkyl; where in the alkyl radicals one or more, or all hydrogen(s) may be replaced by fluorine, or one hydrogen may be replaced by OH, OC(O)CH$_3$, O—CH$_2$-Ph, NH$_2$ or N(COOCH$_2$Ph)$_2$;

S—(C$_1$–C$_6$)-alkyl; S—(CH$_2$)$_n$-phenyl; SO—(C$_1$–C$_6$)-alkyl; SO—(CH$_2$)$_n$-phenyl;

SO$_2$-(C$_1$–C$_6$)-alkyl; or SO$_2$—(CH$_2$)$_n$-phenyl; where n may be =0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl, or NH$_2$;

SO$_2$NH(C$_1$–C$_6$)-alkyl; SO$_2$N[(C$_1$–C$_6$)-alkyl]$_2$; NH$_2$; NH—(C$_1$–C$_6$)-alkyl; N((C$_1$–C$_6$)-alkyl)$_2$; NH(C$_1$–C$_7$)-acyl; phenyl; biphenyl; or O—(CH$_2$)$_n$-phenyl; where n may be =0–6, 1- or 2-naphthyl, 2-, 3- or 4-pyridyl, 2- or 3-furanyl or 2- or 3-thienyl, where the phenyl, biphenyl, naphthyl, pyridyl, furanyl or thienyl rings in each case may be substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl, or CONH$_2$;

1,2,3-triazol-5-yl, where the triazole ring may be substituted in the 1-, 2- or 3-position by methyl or benzyl; tetrazol-5-yl, where the tetrazole ring may be substituted in the 1- or 2-position by methyl or benzyl;

R2 is H, (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(CH$_2$)$_n$-phenyl, C(O)—(CH$_2$)$_n$-thienyl, C(O)—(CH$_2$)$_n$-pyridyl, or C(O)—(CH$_2$)$_n$-furyl, where n may be =0–5 and in which phenyl, thienyl, pyridyl, and furyl in each case may be substituted up to two times by Cl, F, CN, CF$_3$, (C$_1$–C$_3$)-alkyl, OH, O—(C$_1$–C$_6$)-alkyl; C(O)—(C$_1$–C$_6$)-alkyl, or C(O)—(C$_3$–C$_6$)-cycloalkyl;

R3 is (C$_4$–C$_6$)-alkyl, F, CN, N$_3$, O—(C$_1$–C$_6$)-alkyl, CH$_2$—COO(C$_1$–C$_6$ alkyl), CH$_2$—COO(C$_3$–C$_8$ cycloalkyl), CH$_2$—COOH, CH$_2$—CONH$_2$, CH$_2$—CONHCH$_3$, CH$_2$—CON(CH$_3$)$_2$, (CH$_2$)$_n$-phenyl, (CH$_2$)$_n$-thienyl, (CH$_2$)$_n$-pyridyl, or (CH$_2$)$_n$-furyl, where n may be =0–5 and in which phenyl, thienyl, pyridyl, and furyl in each case may be substituted up to two times by Cl, F, CN, CF$_3$, (C$_1$–C$_3$)-alkyl, OH, or O—(C$_1$–C$_6$)-alkyl; (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$, or OC(O)CH$_3$;

R4 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, or (CH$_2$)$_n$-furyl, where n may be =0–5 and in which phenyl, thienyl, pyridyl, and furyl in each case may be substituted up to two times by Cl, F, CN, CF$_3$, (C$_1$–C$_3$)-alkyl, OH, or O—(C$_1$–C$_6$)-alkyl;

R5 is (C$_1$–C$_6$)-alkyl, (C$_3$–C$_6$)-cycloalkyl, (CH$_2$)$_n$-phenyl, (CH$_2$)$_n$-thienyl, (CH$_2$)$_n$-pyridyl, or (CH$_2$)$_n$-furyl, where n may be =0–5 and in which phenyl, thienyl, pyridyl, and furyl in each case may be substituted up to two times by Cl, F, CN, CF$_3$, (C$_1$–C$_3$)-alkyl, OH, or O—(C$_1$–C$_6$)-alkyl;

or

R4 and R5 together form a —CH$_2$—CH$_2$—, —CH$_2$—C(CH$_3$)$_2$—, —CH$_2$—CH$_2$—CH$_2$—, or —CH$_2$—CH$_2$—CH$_2$—CH$_2$— group;

or

C)

Y is a direct bond, —CH$_2$— or —CH$_2$—CH$_2$—;

X is CH$_2$, CH(CH$_3$), CH(C$_2$H$_5$), or CH(C$_3$H$_7$);

R1 and R1' independently of one another are H; F; Cl; Br; I; NO$_2$; CN; COOH; COO(C$_1$–C$_6$)-alkyl; CONH$_2$; CONH(C$_1$–C$_6$)-alkyl; CON[(C$_1$–C$_6$)-alkyl]$_2$; (C$_1$–C$_6$)-alkyl; (C$_2$–C$_6$)-alkenyl; (C$_2$–C$_6$)-alkynyl; O—(C$_1$–C$_6$)-alkyl; O—CH$_2$—CF$_3$; O—CH$_2$—CF$_2$—CF$_3$; or O—(C$_4$–C$_6$)-alkyl, where in the alkyl radicals one or more, or all hydrogen(s) may be replaced by fluorine, or one hydrogen may be replaced by OH, OC(O)CH$_3$, O—CH$_2$—Ph, NH$_2$ or N(COOCH$_2$Ph)$_2$;

S—(C$_1$–C$_6$)-alkyl; S—(CH$_2$)$_n$-phenyl; SO—(C$_1$–C$_6$)-alkyl; SO—(CH$_2$)$_n$-phenyl; SO$_2$—(C$_1$–C$_6$)-alkyl; or SO$_2$—(CH$_2$)$_n$-phenyl; where n may be =0–6 and the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl, or NH$_2$;

SO$_2$—NH$_2$; SO$_2$NH(C$_1$–C$_6$)-alkyl; SO$_2$N[(C$_1$–C$_6$)-alkyl]$_2$; NH$_2$; NH—(C$_1$–C$_6$)-alkyl; N((C$_1$–C$_6$)-alkyl)$_2$; NH(C$_1$–C$_7$)-acyl; phenyl; biphenyl; or O—(CH$_2$)$_n$-phenyl, where n may be =0–6, 1- or 2-naphthyl, 2-, 3- or 4-pyridyl, 2- or 3-furanyl or 2- or 3-thienyl, where the phenyl, biphenyl, naphthyl, pyridyl, furanyl or thienyl rings in each case may be substituted one to 3 times by F, Cl, Br, I, OH, CF$_3$, NO$_2$, CN, OCF$_3$, O—(C$_1$–C$_6$)-alkyl, (C$_1$–C$_6$)-alkyl, NH$_2$, NH(C$_1$–C$_6$)-alkyl, N((C$_1$–C$_6$)-alkyl)$_2$, SO$_2$—CH$_3$, COOH, COO—(C$_1$–C$_6$)-alkyl, or CONH$_2$;

1,2,3-triazol-5-yl, where the triazole ring may be substituted in the 1-, 2- or 3-position by methyl or benzyl; tetrazol-5-yl, where the tetrazole ring may be substituted in the 1- or 2-position by methyl or benzyl;

R2 is (C$_1$–C$_6$)-alkyl, C$_2$–C$_8$alkenyl, C$_2$–C$_8$alkinyl, (C$_3$–C$_6$)-cycloalkyl, (CH$_2$)$_n$-phenyl, (CH$_2$)$_n$-thienyl, (CH$_2$)$_n$-pyridyl, (CH$_2$)$_n$-furyl, C(O)—(CH$_2$)$_n$-phenyl, C(O)—(CH$_2$)$_n$-thienyl, C(O)—(CH$_2$)$_n$-pyridyl, or C(O)—(CH$_2$)$_n$-furyl, where n may be =0–5 and in which phenyl, thienyl, pyridyl, and furyl in each case may be substituted up to two times by Cl, F, CN, CF$_3$, (C$_1$–C$_3$)-alkyl, OH, O—(C$_1$–C$_6$)-alkyl; C(O)—(C$_1$–C$_6$)-alkyl, or C(O)—(C$_3$–C$_6$)-cycloalkyl;

R3 is H, (C$_1$–C$_6$)-alkyl, F, CN, N$_3$, O—(C$_1$–C$_6$)-alkyl, CH$_2$—COO(C$_1$–C$_6$ alkyl), CH$_2$—COO(C$_3$–C$_8$ cycloalkyl), CH$_2$—COOH, CH$_2$—CONH$_2$, CH$_2$—CONHCH$_3$, CH$_2$—CON(CH$_3$)$_2$, (CH$_2$)$_n$-phenyl, (CH$_2$)$_n$-thienyl, (CH$_2$)$_n$-pyridyl, or (CH$_2$)$_n$-furyl, where n may be =0–5 and in which phenyl, thienyl, pyridyl, and furyl in each case may be substituted up to two times by Cl, F, CN, CF$_3$, (C$_1$–C$_3$)-alkyl, OH, O—(C$_1$–C$_6$)-alkyl; (C$_2$–C$_6$)-alkynyl, (C$_2$–C$_6$)-alkenyl, C(O)OCH$_3$, C(O)OCH$_2$CH$_3$, C(O)OH, C(O)NH$_2$, C(O)NHCH$_3$, C(O)N(CH$_3$)$_2$, or OC(O)CH$_3$;

R4 is $(C_1-C_6)$-alkyl, $(C_3-C_6)$-cycloalkyl, $(CH_2)_n$-phenyl, $(CH_2)_n$-thienyl, $(CH_2)_n$-pyridyl, or $(CH_2)_n$-furyl, where n may be =0–5 and in which phenyl, thienyl, pyridyl, and furyl in each case may be substituted up to two times by Cl, F, CN, $CF_3$, $(C_1-C_3)$-alkyl, OH, or O—$(C_1-C_6)$-alkyl;

R5 is $(C_1-C_6)$-alkyl, $(C_3-C_6)$-cycloalkyl, $(CH_2)_n$-phenyl, $(CH_2)_n$-thienyl, $(CH_2)_n$-pyridyl, or $(CH_2)_n$-furyl, where n may be =0–5 and in which phenyl, thienyl, pyridyl, and furyl in each case may be substituted up to two times by Cl, F, CN, $CF_3$, $(C_1-C_3)$-alkyl, OH, or O—$(C_1-C_6)$-alkyl;

or

R4 and R5 together form a —$CH_2$—$CH_2$—, —$CH_2$—$C(CH_3)_2$—, —$CH_2$—$CH_2$—$CH_2$—, or —$CH_2$—$CH_2$—$CH_2$—$CH_2$— group;

or

D)

Y is a direct bond, —$CH_2$— or —$CH_2$—$CH_2$—;

X is CH(phenyl), where the phenyl radical may be substituted by F, Cl, Br or I, O, S, SO, $SO_2$ or N-$R_6$;

R1 and R1' independently of one another are H; F; Cl; Br; I; $NO_2$; CN; COOH; COO$(C_1-C_6)$-alkyl; $CONH_2$; CONH$(C_1-C_6)$-alkyl; CON$[(C_1-C_6)$-alkyl$]_2$; $(C_1-C_6)$-alkyl; $(C_2-C_6)$-alkenyl; $(C_2-C_6)$-alkynyl; O—$(C_1-C_6)$-alkyl; O—$CH_2$—$CF_3$; O—$CH_2$—$CF_2$—$CF_3$; or O—$(C_4-C_6)$-alkyl, where in the alkyl radicals one or more, or all hydrogen(s) may be replaced by fluorine, or one hydrogen may be replaced by OH, OC(O)$CH_3$, O—$CH_2$—Ph, $NH_2$ or N(COO$CH_2$Ph)$_2$;

S—$(C_1-C_6)$-alkyl; S—$(CH_2)_n$-phenyl; SO—$(C_1-C_6)$-alkyl; SO—$(CH_2)_n$-phenyl; $SO_2$—$(C_1-C_6)$-alkyl; or $SO_2$—$(CH_2)_n$-phenyl, where n may be =0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl, or $NH_2$; $SO_2$—$NH_2$; $SO_2NH(C_1-C_6)$-alkyl; $SO_2N[(C_1-C_6)$-alkyl$]_2$; $NH_2$; NH—$(C_1-C_6)$-alkyl; N$((C_1-C_6)$-alkyl$)_2$; NH$(C_1-C_7)$-acyl; phenyl; biphenyl; or O—$(CH_2)_n$-phenyl, where n may be =0–6, 1- or 2-naphthyl, 2-, 3- or 4-pyridyl, 2- or 3-furanyl or 2- or 3-thienyl, where the phenyl, biphenyl, naphthyl, pyridyl, furanyl or thienyl rings in each case may be substituted one to 3 times by F, Cl, Br, I, OH, $CF_3$, $NO_2$, CN, $OCF_3$, O— $(C_1-C_6)$-alkyl, $(C_1-C_6)$-alkyl, $NH_2$, NH$(C_1-C_6)$-alkyl, N$((C_1-C_6)$-alkyl$)_2$, COOH, COO—$(C_1-C_6)$-alkyl, or $CONH_2$; 1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R2 is H, $(C_1-C_6)$-alkyl, $(C_3-C_6)$-cycloalkyl, $(CH_2)_n$-phenyl, $(CH_2)_n$-thienyl, $(CH_2)_n$-pyridyl, $(CH_2)_n$-furyl, C(O)—$(CH_2)_n$-phenyl, C(O)—$(CH_2)_n$-thienyl, C(O)—$(CH_2)_n$-pyridyl, or C(O)—$(CH_2)_n$-furyl, where n may be =0–5 and in which phenyl, thienyl, pyridyl, and furyl in each case may be substituted up to two times by Cl, F, CN, $CF_3$, $(C_1-C_3)$-alkyl, OH, O—$(C_1-C_6)$-alkyl; C(O)—$(C_1-C_6)$-alkyl, or C(O)—$(C_3-C_6)$-cycloalkyl;

R3 is H, $(C_1-C_6)$-alkyl, F, CN, $N_3$, O—$(C_1-C_6)$-alkyl, $CH_2$—COO$(C_1-C_6$ alkyl), $CH_2$—COO$(C_3-C_8$ cycloalkyl), $CH_2$—COOH, $CH_2$—$CONH_2$, $CH_2$—$CONHCH_3$, $CH_2$—CON$(CH_3)_2$, $(CH_2)_n$-phenyl, $(CH_2)_n$-thienyl, $(CH_2)_n$-pyridyl, or $(CH_2)_n$-furyl, where n may be =0–5 and in which phenyl, thienyl, pyridyl, and furyl in each case may be substituted up to two times by Cl, F, CN, $CF_3$, $(C_1-C_3)$-alkyl, OH, O—$(C_1-C_6)$-alkyl; $(C_2-C_6)$-alkynyl, $(C_2-C_6)$-alkenyl, C(O)O$CH_3$, C(O)O$CH_2CH_3$, C(O)OH, C(O)$NH_2$, C(O)NH$CH_3$, C(O)N$(CH_3)_2$, or OC(O)$CH_3$;

R4 is $(C_1-C_6)$-alkyl, $(C_3-C_6)$-cycloalkyl, $(CH_2)_n$-phenyl, $(CH_2)_n$-thienyl, $(CH_2)_n$-pyridyl, or $(CH_2)_n$-furyl, where n may be =0–5 and in which phenyl, thienyl, pyridyl, and furyl in each case may be substituted up to two times by Cl, F, CN, $CF_3$, $(C_1-C_3)$-alkyl, OH, or O—$(C_1-C_6)$-alkyl;

R5 is $(C_1-C_6)$-alkyl, $(C_3-C_6)$-cycloalkyl, $(CH_2)_n$-phenyl, $(CH_2)_n$-thienyl, $(CH_2)_n$-pyridyl, or $(CH_2)_n$-furyl, where n may be =0–5 and in which phenyl, thienyl, pyridyl, and furyl in each case may be substituted up to two times by Cl, F, CN, $CF_3$, $(C_1-C_3)$-alkyl, OH, or O—$(C_1-C_6)$-alkyl;

or

R4 and R5 together form a —$CH_2$—$CH_2$—, —$CH_2$—$C(CH_3)_2$—, —$CH_2$—$CH_2$—$CH_2$—, or —$CH_2$—$CH_2$—$CH_2$—$CH_2$— group;

R6 is $SO_2$—$(C_6H_4$-4-$CH_3)$ or

E)

Y is a direct bond, —$CH_2$— or —$CH_2$—$CH_2$—;

X is $CH_2$, CH$(CH_3)$, CH$(C_2H_5)$, or CH$(C_3H_7)$;

R1 is H, F, Cl, Br, I, $CH_3$, $CF_3$, or O—$(C_1-C_3)$-alkyl;

R1' is H, F, Cl, Br, I, or $NO_2$;

R2 is H;

R3 is H, or $(C_1-C_3)$-alkyl;

R4 is phenyl, where the phenyl radical may be substituted up to two times by F, Cl, Br, I, $(C_1-C_6)$-alkyl, $(C_3-C_6)$-cycloalkyl, O—$(C_1-C_3)$-alkyl, $CF_3$, $OCF_3$, O—$CH_2$-phenyl, COOH, COO$(C_1-C_6)$-alkyl, COO $(C_3-C_6)$-cycloalkyl, or $CONH_2$;

R5 is phenyl, where the phenyl radical may be substituted up to two times by F, Cl, Br, I, $(C_1-C_6)$-alkyl, $(C_3-C_6)$-cycloalkyl, O—$(C_1-C_3)$-alkyl, $CF_3$, $OCF_3$, O—$CH_2$-phenyl, COOH, COO$(C_1-C_6)$-alkyl, COO $(C_3-C_6)$-cycloalkyl, or $CONH_2$;

or a physiologically tolerable salt thereof or a physiologically functional derivative thereof.

2. A compound of the formula I as claimed in claim 1, wherein

A)

Y is a direct bond, or —$CH_2$;

X is $CH_2$, CH$(CH_3)$, CH$(C_2H_5)$, or CH$(C_3H_7)$;

R1 is CN; COOH; COO$(C_1-C_6)$-alkyl; $CONH_2$; CONH$(C_1-C_6)$-alkyl; CON$[(C_1-C_6)$-alkyl$]_2$; $(C_2-C_6)$-alkyl; $(C_2-C_6)$-alkenyl; $(C_2-C_6)$-alkynyl; O—$CH_2$—$CF_3$; O—$CH_2$—$CF_2$—$CF_3$, or O—$(C_4-C_6)$-alkyl, where in the alkyl radicals one or more, or all hydrogen(s) may be replaced by fluorine, or one hydrogen may be replaced by OH, OC(O)$CH_3$, O—$CH_2$—Ph, $NH_2$ or N(COO$CH_2$Ph)$_2$;

S—$(C_1-C_6)$-alkyl; S—$(CH_2)_n$-phenyl; SO—$(C_1-C_6)$-alkyl; or SO—$(CH_2)_n$-phenyl, where the phenyl radical may be substituted up to two times by F, Cl, Br, OH, $CF_3$, $NO_2$, CN, $OCF_3$, O—$(C_1-C_6)$-alkyl, or $(C_1-C_6)$-alkyl; NH—$(C_1-C_6)$-alkyl; N$((C_1-C_6)$-alkyl$)_2$; NH$(C_1-C_7)$-acyl; phenyl; or O—$(CH_2)_n$-phenyl, where n may be =0–6, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted one to 3 times by F, Cl, I, OH, $CF_3$, CN, $OCF_3$, O—$(C_1$–$C_6)$-alkyl, $(C_1$–$C_6)$-alkyl, $NH_2$, $NH(C_1$–$C_6)$-alkyl, $N((C_1$–$C_6)$-alkyl$)_2$, COOH, COO—$(C_1$–$C_6)$-alkyl, or $CONH_2$;

1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R1' is H, F, Cl, Br, I, $CH_3$, $CF_3$, O—$(C_1$–$C_3)$-alkyl, $SO_2$—$NH_2$, $SO_2$, $NH(C_1$–$C_6)$-alkyl, $SO_2N[(C_1$–$C_6)$-alkyl$]_2$ or R1;

R2 is H, $(C_1$–$C_6)$-alkyl, $(CH_2)_n$-phenyl, $(CH_2)_n$-thienyl, $(CH_2)_n$-pyridyl, C(O)—$(CH_2)_n$-phenyl, C(O)—$(CH_2)_n$-thienyl, or C(O)—$(CH_2)_n$-pyridyl, where n may be =0–3 and in which phenyl, thienyl, pyridyl, and furyl in each case may be substituted up to two times by Cl, F, CN, $CF_3$, $(C_1$–$C_3)$-alkyl, OH, or O—$(C_1$–$C_6)$-alkyl;

R3 is H, $(C_1$–$C_6)$-alkyl, F, CN, O—$(C_1$–$C_6)$-alkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1$–$C_3)$-alkyl, OH, O—$(C_1$–$C_6)$-alkyl; $(C_2$–$C_6)$-alkynyl, $(C_2$–$C_6)$-alkenyl, $C(O)OCH_3$, $C(O)OCH_2CH_3$, C(O)OH, $C(O)NH_2$, $C(O)N(CH_3)_2$, or $OC(O)CH_3$;

R4 is $(C_1$–$C_6)$-alkyl, $(C_3$–$C_6)$-cycloalkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1$–$C_3)$-alkyl, OH, or O—$(C_1$–$C_6)$-alkyl;

R5 is $(C_1$–$C_6)$-alkyl, $(C_3$–$C_6)$-cycloalkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1$–$C_3)$-alkyl, OH, or O—$(C_1$–$C_6)$-alkyl;

or

R4 and R5 —together form a —$CH_2$—$CH_2$—, —$CH_2$—$C(CH_3)_2$— or —$CH_2$—$CH_2$—$CH_2$— group;

or

B)

Y is a direct bond, or —$CH_2$—;

X is $CH_2$, $CH(CH_3)$, $CH(C_2H_5)$, or $CH(C_3H_7)$;

R1 and R1' independently of one another are H; F; Cl; Br; I; CN; COOH; $COO(C_1$–$C_6)$-alkyl; $CONH_2$; $CONH(C_1$–$C_6)$-alkyl; $CON[(C_1$–$C_6)$-alkyl$]_2$; $(C_1$–$C_6)$-alkyl; $(C_2$–$C_6)$-alkenyl; $(C_2$–$C_6)$-alkynyl; O—$(C_1$–$C_6)$-alkyl; O—$CH_2$—$CF_3$; O—$CH_2$—$CF_2$—$CF_3$; or O—$(C_4$–$C_6)$-alkyl, where in the alkyl radicals one or more, or all hydrogen(s) may be replaced by fluorine, or one hydrogen may be replaced by OH, $OC(O)CH_3$, O—$CH_2$—Ph, $NH_2$ or $N(COOCH_2Ph)_2$;

S—$(C_1$–$C_6)$-alkyl, S—$(CH_2)_n$-phenyl, SO—$(C_1$–$C_6)$-alkyl, or SO—$(CH_2)_n$-phenyl, where the phenyl radical may be substituted up to two times by F, Cl, Br, OH, $CF_3$, $NO_2$, CN, $OCF_3$, O—$(C_1$–$C_6)$-alkyl, $(C_1$–$C_6)$-alkyl;

$SO_2$—$NH_2$; $SO_2NH(C_1$–$C_6)$-alkyl; $SO_2N[(C_1$–$C_6)$-alkyl$]_2$; NH—$(C_1$–$C_6)$-alkyl; $N((C_1$–$C_6)$-alkyl$)_2$; $NH(C_1$–$C_7)$-acyl; phenyl; or O—$(CH_2)_n$-phenyl, where n may be =0–6, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted one to 3 times by F, Cl, I, OH, $CF_3$, CN, $OCF_3$, O—$(C_1$–$C_6)$-alkyl, $(C_1$–$C_6)$-alkyl, $NH_2$, $NH(C_1$–$C_6)$-alkyl, $N((C_1$–$C_6)$-alkyl$)_2$, COOH, COO—$(C_1$–$C_6)$-alkyl, or $CONH_2$;

1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R2 is H, $(C_1$–$C_6)$-alkyl, $(CH_2)_n$-phenyl, $(CH_2)_n$-thienyl, $(CH_2)_n$-pyridyl, C(O)—$(CH_2)_n$-phenyl, C(O)—$(CH_2)_n$-thienyl, or C(O)—$(CH_2)_n$-pyridyl, where n may be =0–3 and in which phenyl, thienyl, pyridyl, and furyl in each case may be substituted up to two times by Cl, F, CN, $CF_3$, $(C_1$–$C_3)$-alkyl, OH, or O—$(C_1$–$C_6)$-alkyl;

R3 is $(C_4$–$C_6)$-alkyl, F, CN, $N_3$, O—$(C_1$–$C_6)$-alkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1$–$C_3)$-alkyl, OH, O—$(C_1$–$C_6)$-alkyl; $(C_2$–$C_6)$-alkynyl, $(C_2$–$C_6)$-alkenyl, $C(O)OCH_3$, $C(O)OCH_2CH_3$, C(O)OH, $C(O)NH_2$, $C(O)NHCH_3$, $C(O)N(CH_3)_2$, or $OC(O)CH_3$;

R4 is $(C_1$–$C_6)$-alkyl, $(C_3$–$C_6)$-cycloalkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1$–$C_3)$-alkyl, OH, or O—$(C_1$–$C_6)$-alkyl;

R5 is $(C_1$–$C_6)$-alkyl, $(C_3$–$C_6)$-cycloalkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1$–$C_3)$-alkyl, OH, or O—$(C_1$–$C_6)$-alkyl;

or

R4 and R5 together form a —$CH_2$—$CH_2$—, —$CH_2$—$C(CH_3)_2$— or —$CH_2$—$CH_2$—$CH_2$— group;

or

C)

Y is a direct bond, or —$CH_2$—;

X is $CH_2$, $CH(CH_3)$, $CH(C_2H_5)$, or $CH(C_3H_7)$;

R1 and R1' independently of one another are H; F; Cl; Br; I; CN; COOH; $COO(C_1$–$C_6)$-alkyl; $CONH_2$; $CONH(C_1$–$C_6)$-alkyl; $CON[(C_1$–$C_6)$-alkyl$]_2$; $(C_1$–$C_6)$-alkyl; $(C_2$–$C_6)$-alkenyl; $(C_2$–$C_6)$-alkynyl; O—$(C_1$–$C_6)$-alkyl; O—$CH_2$—$CF_3$; O—$CH_2$—$CF_2$—$CF_3$; or O—$(C_4$–$C_6)$-alkyl, where in the alkyl radicals one or more, or all hydrogen(s) may be replaced by fluorine, or one hydrogen may be replaced by OH, $OC(O)CH_3$, O—$CH_2$—Ph, $NH_2$ or $N(COOCH_2Ph)_2$;

S—$(C_1$–$C_6)$-alkyl, S—$(CH_2)_n$-phenyl, $SO_2$—$(C_1$–$C_6)$-alkyl, or $SO_2$—$(CH_2)_n$-phenyl, where n may be =0–6 and the phenyl radical may be substituted up to two times by F, Cl, Br, OH, $CF_3$, $NO_2$, CN, $OCF_3$, O—$(C_1$–$C_6)$-alkyl, $(C_1$–$C_6)$-alkyl;

$SO_2$—$NH_2$; $SO_2NH(C_1$–$C_6)$-alkyl; $SO_2N[(C_1$–$C_6)$-alkyl$]_2$; NH—$(C_1$–$C_6)$-alkyl; $N((C_1$–$C_6)$-alkyl$)_2$; $NH(C_1$–$C_7)$-acyl; phenyl; or O—$(CH_2)_n$-phenyl, where n may be =0–4, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted one to 3 times by F, Cl, I, OH, $CF_3$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, COOH, COO—$(C_1-C_6)$-alkyl, or $CONH_2$;

1,2,3-triazol-5-yl, where the triazole ring may be substituted in the 1-, 2- or 3-position by methyl or benzyl;

etrazol-5-yl, where the tetrazole ring may be substituted in the 1- or 2-position by methyl or benzyl;

R2 is $(C_1-C_6)$-alkyl, $(CH_2)_n$-phenyl, $(CH_2)_n$-thienyl, $(CH_2)_n$-pyridyl, C(O)—$(CH_2)_n$-phenyl, C(O)—$(CH_2)_n$-thienyl, or C(O)—$(CH_2)_n$-pyridyl, where n may be =0–3 and in which phenyl, thienyl, pyridyl, and furyl in each case may be substituted up to two times by Cl, F, CN, $CF_3$, $(C_1-C_3)$-alkyl, OH, or O—$(C_1-C_6)$-alkyl;

R3 is H, $(C_1-C_6)$-alkyl, F, CN, O—$(C_1-C_6)$-alkyl, $(CH_2)_n$-phenyl, $(CH_2)_n$-thienyl, or $(CH_2)_n$-pyridyl, where n may be =0–3 and in which phenyl, thienyl, pyridyl in each case may be substituted up to two times by Cl, F, CN, $CF_3$, $(C_1-C_3)$-alkyl, OH, O—$(C_1-C_6)$-alkyl; $(C_2-C_6)$-alkynyl, $(C_2-C_6)$-alkenyl, $C(O)OCH_3$, $C(O)OCH_2CH_3$, C(O)OH, $C(O)NH_2$, $C(O)N(CH_3)_2$, or $OC(O)CH_3$;

R4 is $(C_1-C_6)$-alkyl, $(C_3-C_6)$-cycloalkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1-C_3)$-alkyl, OH, or O—$(C_1-C_6)$-alkyl;

R5 is $(C_1-C_6)$-alkyl, $(C_3-C_6)$-cycloalkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1-C_3)$-alkyl, OH, or O—$(C_1-C_6)$-alkyl;

or

R4 and R5 together form a —$CH_2$—$CH_2$—, —$CH_2$—C$(CH_3)_2$— or —$CH_2$—$CH_2$—$CH_2$— group;

or

D)

Y is a direct bond, or —$CH_2$—;

X is CH(phenyl), where the phenyl radical may be substituted by F, Cl or Br, O, S, SO, $SO_2$ or N-$R_6$;

R1 and R1' independently of one another are H; F; Cl; Br; I; CN; COOH; COO$(C_1-C_6)$-alkyl; $CONH_2$; $CONH(C_1-C_6)$-alkyl; $CON[(C_1-C_6)$-alkyl$]_2$; $(C_1-C_6)$-alkyl; $(C_2-C_6)$-alkenyl; $(C_2-C_6)$-alkynyl; O—$(C_1-C_6)$-alkyl; O—$CH_2$—$CF_3$; O—$CH_2$—$CF_2$—$CF_3$; or O—$(C_4-C_6)$-alkyl, where in the alkyl radicals one or more, or all hydrogen(s) may be replaced by fluorine, or one hydrogen may be replaced by OH, $OC(O)CH_3$, O—$CH_2$—Ph, $NH_2$ or $N(COOCH_2Ph)_2$;

S—$(C_1-C_6)$-alkyl; S—$(CH_2)_n$-phenyl; $SO_2$—$(C_1-C_6)$-alkyl; or $SO_2$—$(CH_2)_n$-phenyl, where n may be =0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl; $SO_2$—$NH_2$; $SO_2NH(C_1-C_6)$-alkyl; $SO_2N[(C_1-C_6)$-alkyl$]_2$; $NH_2$; NH—$(C_1-C_6)$-alkyl; $N((C_1-C_6)$-alkyl$)_2$; $NH(C_1-C_7)$-acyl; phenyl; or O—$(CH_2)_n$-phenyl, where n may be =0–6, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted one to 3 times by F, Cl, I, OH, $CF_3$, CN, $OCF_3$, O—$(C_1-C_6)$-alkyl, $(C_1-C_6)$-alkyl, $NH_2$, $NH(C_1-C_6)$-alkyl, $N((C_1-C_6)$-alkyl$)_2$, COOH, COO—$(C_1-C_6)$-alkyl, or $CONH_2$;

1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R2 is H, $(C_1-C_6)$-alkyl, $(CH_2)_n$-phenyl, $(CH_2)_n$-thienyl, $(CH_2)_n$-pyridyl, C(O)—$(CH_2)_n$-phenyl, C(O)—$(CH_2)_n$-thienyl, or C(O)—$(CH_2)_n$-pyridyl, where n may be =0–3 and in which phenyl, thienyl, pyridyl, and furyl in each case may be substituted up to two times by Cl, F, CN, $CF_3$, $(C_1-C_3)$-alkyl, OH, or O—$(C_1-C_6)$-alkyl;

R3 is H, $(C_1-C_6)$-alkyl, F, CN, O—$(C_1-C_6)$-alkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1-C_3)$-alkyl, OH, O—$(C_1-C_6)$-alkyl; $(C_2-C_6)$-alkynyl, $(C_2-C_6)$-alkenyl, $C(O)OCH_3$, $C(O)OCH_2CH_3$, C(O)OH, $C(O)NH_2$, $C(O)NHCH_3$, $C(O)N(CH_3)_2$, or $OC(O)CH_3$;

R4 is $(C_1-C_6)$-alkyl, $(C_3-C_6)$-cycloalkyl, $(CH_2)_n$-phenyl, $(CH_2)_n$-thienyl, or $(CH_2)_n$-pyridyl, where n may be =0–3 and in which phenyl, thienyl, and pyridyl in each case may be substituted up to two times by Cl, F, CN, $CF_3$, $(C_1-C_3)$-alkyl, OH, or O—$(C_1-C_6)$-alkyl;

R5 is $(C_1-C_6)$-alkyl, $(C_3-C_6)$-cycloalkyl, $(CH_2)_n$-phenyl, $(CH_2)_n$-thienyl, or $(CH_2)_n$-pyridyl, where n may be =0–3 and in which phenyl, thienyl, pyridyl in each case may be substituted up to two times by Cl, F, CN, $CF_3$, $(C_1-C_3)$-alkyl, OH, or O—$(C_1-C_6)$-alkyl;

or

R4 and R5 together form a —$CH_2$—$CH_2$—, —$CH_2$—C$(CH_3)_2$— or —$CH_2$—$CH_2$—$CH_2$— group;

R6 is $SO_2$—$(C_6H_4$-4-$CH_3)$ or

E)

Y is a direct bond or —$CH_2$—;

X is $CH_2$, $CH(CH_3)$, $CH(C_2H_5)$, or $CH(C_3H_7)$;

R1 is H, F, Cl, Br, I, $CH_3$, $CF_3$, or O—$(C_1-C_3)$-alkyl;

R1' is H, F, Cl, Br, or I;

R2 is H;

R3 is H, or $(C_1-C_3)$-alkyl;

R4 is phenyl, where the phenyl radical may be substituted up to two times by F, Cl, Br, I, $(C_1-C_6)$-alkyl, $(C_3-C_6)$-cycloalkyl, O—$(C_1-C_3)$-alkyl, $CF_3$, $OCF_3$, O—$CH_2$-phenyl, COOH, $COO(C_1-C_6)$-alkyl, or $CONH_2$;

R5 is phenyl, where the phenyl radical may be substituted up to two times by F, Cl, Br, I, $(C_1-C_6)$-alkyl, $(C_3-C_6)$-cycloalkyl, O—$(C_1-C_3)$-alkyl, $CF_3$, $OCF_3$, O—$CH_2$-phenyl, COOH, $COO(C_1-C_6)$-alkyl, or $CONH_2$;

or a physiologically tolerable salt thereof or a physiologically functional derivative thereof.

3. A compound of the formula I, as claimed in claim 1, wherein

A)

Y is a direct bond;

X is $CH_2$, $CH(CH_3)$, $CH(C_2H_5)$, or $CH(C_3H_7)$;

R1 is CN; COOH; $COO(C_1-C_6)$-alkyl; $CONH_2$; $CON[(C_1-C_6)$-alkyl$]_2$; $(C_2-C_6)$-alkyl; $(C_2-C_6)$-alkenyl; $(C_2-C_6)$-alkynyl; O—$CH_2$—$CF_3$; O—$CH_2$—$CF_2$—$CF_3$; or O—$(C_4-C_6)$-alkyl, where in the alkyl radicals one or more, or all hydrogen(s) may be replaced by fluorine, or one hydrogen may be replaced by OH, OC(O)CH$_3$, O—CH$_2$—Ph, NH$_2$ or N(COOCH$_2$Ph)$_2$;

S—(C$_1$–C$_6$)-alkyl; S—(CH$_2$)$_n$-phenyl; SO—(C$_{1-C6}$)-alkyl; or SO—(CH$_2$)$_n$-phenyl, where the phenyl radical may be substituted up to two times by F, Cl, Br, OH, CF$_3$, NO$_2$, CN, OCF$_3$, O—(C$_1$–C$_6$)-alkyl, (C$_1$–C$_6$)-alkyl; NH—(C$_1$–C$_6$)-alkyl; N((C$_1$–C$_6$)-alkyl)$_2$; NH(C$_1$–C$_7$)-acyl; phenyl; or O—(CH$_2$)$_n$-phenyl, where n may be =0–3 6, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted one to 2 times by F, Cl, OH, CF$_3$, CN, OCF$_3$, O—(C$_1$–C$_6$)-alkyl, (C$_1$–C$_6$)-alkyl, COOH, COO—(C$_1$–C$_6$)-alkyl, or CONH$_2$;

1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R1' is H, F, Cl, CH$_3$, CF$_3$, O—(C$_1$–C$_3$)-alkyl, SO$_2$—NH$_2$, SO$_2$NH(C$_1$–C$_6$)-alkyl, SO$_2$N[(C$_1$–C$_6$)-alkyl]$_2$ or R1;

R2 is H; (C$_1$–C$_6$)-alkyl; (CH$_2$)$_n$-phenyl; (CH$_2$)$_n$-pyridyl; C(O)—(CH$_2$)$_n$-phenyl; or C(O)—(CH$_2$)$_n$-pyridyl, where n may be =0–3 and in which phenyl, or pyridyl in each case may be substituted up to two times by Cl, F, CN, CF$_3$, (C$_1$–C$_3$)-alkyl, or O—(C$_1$–C$_6$)-alkyl; C(O)—(C$_1$–C$_6$)-alkyl;

R3 is H, (C$_1$–C$_6$)-alkyl, F, CN, O—(C$_1$–C$_6$)-alkyl, (CH$_2$)$_n$-phenyl, or (CH$_2$)$_n$-pyridyl, where n may be =0–3 and in which phenyl, and pyridyl in each case may be substituted up to two times by Cl, F, CN, CF$_3$, (C$_1$–C$_3$)-alkyl, O—(C$_1$–C$_6$)-alkyl; (C$_2$–C$_6$)-alkynyl, C(O)OCH$_3$, C(O)OCH$_2$CH$_3$, C(O)OH, C(O)NH$_2$, C(O)N(CH$_3$)$_2$, or OC(O)CH$_3$;

R4 is (C$_1$–C$_6$)-alkyl, (C$_3$–C$_6$)-cycloalkyl, (CH$_2$)$_n$-phenyl, or (CH$_2$)$_n$-pyridyl, where n may be =0–3 and in which phenyl and pyridyl in each case may be substituted up to two times by Cl, F, CN, CF$_3$, (C$_1$–C$_3$)-alkyl, or O—(C$_1$–C$_6$)-alkyl;

R5 is (C$_1$–C$_6$)-alkyl, (C$_3$–C$_6$)-cycloalkyl, (CH$_2$)$_n$-phenyl, or (CH$_2$)$_n$-pyridyl, where n may be =0–3 and in which phenyl and pyridyl in each case may be substituted up to two times by Cl, F, CN, CF$_3$, (C$_1$–C$_3$)-alkyl, or O—(C$_1$–C$_6$)-alkyl;

or

R4 and R5 together form a —CH$_2$—CH$_2$—, —CH$_2$—C(CH$_3$)$_2$— or —CH$_2$—CH$_2$—CH$_2$— group;

or

B)
Y is a direct bond, or —CH$_2$—;
X is CH$_2$, CH(CH$_3$), CH(C$_2$H$_5$), or CH(C$_3$H$_7$);
R1 and R1' independently of one another are H; F; Cl; Br; I; CN; COOH; COO(C$_1$–C$_6$)-alkyl; CONH$_2$; CON[(C$_1$–C$_6$)-alkyl]$_2$; (C$_1$–C$_6$)-alkyl; (C$_2$–C$_6$)-alkenyl; (C$_2$–C$_6$)-alkynyl; O—(C$_1$–C$_6$)-alkyl; O—CH$_2$—CF$_3$; O—CH$_2$—CF$_2$—CF$_3$; or O—(C$_4$–C$_6$)-alkyl, where in the alkyl radicals one or more, or all hydrogen(s) may be replaced by fluorine, or one hydrogen may be replaced by OH, OC(O)CH$_3$, O—CH$_2$—Ph, NH$_2$ or N(COOCH$_2$Ph)$_2$;

S—(C$_1$–C$_6$)-alkyl; S—(CH$_2$)$_n$-phenyl; SO—(C$_1$–C$_6$)-alkyl; or SO—(CH$_2$)$_n$-phenyl, where the phenyl radical may be substituted up to two times by F, Cl, OH, CF$_3$, OCF$_3$, O—(C$_1$–C$_6$)-alkyl, or (C$_1$–C$_6$)-alkyl; SO$_2$—NH$_2$; SO$_2$NH(C$_1$–C$_6$)-alkyl; SO$_2$N[(C$_1$–C$_6$)-alkyl]$_2$; N((C$_1$–C$_6$)-alkyl)$_2$; NH(C$_1$–C$_7$)-acyl; phenyl; or O—(CH$_2$)$_n$-phenyl, where n may be =0–3 6, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted one to 3 times by F, Cl, I, OH, CF$_3$, CN, OCF$_3$, O—(C$_1$–C$_6$)-alkyl, (C$_1$–C$_6$)-alkyl, NH$_2$, N((C$_1$–C$_6$)-alkyl)$_2$, COOH, COO—(C$_1$–C$_6$)-alkyl, or CONH$_2$;

1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R2 is H, (C$_1$–C$_6$)-alkyl, (CH$_2$)$_n$-phenyl, (CH$_2$)$_n$-pyridyl, C(O)—(CH$_2$)$_n$-pheny, or C(O)—(CH$_2$)$_n$-pyridyl, where n may be =0–3 and in which phenyl, and pyridyl in each case may be substituted up to two times by Cl, F, CN, CF$_3$, (C$_1$–C$_3$)-alkyl, OH, or O—(C$_1$–C$_6$)-alkyl; C(O)—(C$_1$–C$_6$)-alkyl;

R3 is (C$_4$–C$_6$)-alkyl, F, CN, N$_3$, O—(C$_1$–C$_6$)-alkyl, (CH$_2$)n-phenyl, or (CH$_2$)$_n$-pyridyl, where n may be =0–3 and in which phenyl and pyridyl in each case may be substituted up to two times by Cl, F, CN, CF$_3$, (C$_1$–C$_3$)-alkyl, or O—(C$_1$–C$_6$)-alkyl; (C$_2$–C$_6$)-alkynyl, C(O)OCH$_3$, C(O)OCH$_2$CH$_3$, C(O)OH, C(O)NH$_2$, C(O)NHCH$_3$, C(O)N(CH$_3$)$_2$, OC(O)CH$_3$;

R4 is (C$_1$–C$_6$)-alkyl, (C$_3$–C$_6$)-cycloalkyl, (CH$_2$)$_n$-phenyl, or (CH$_2$)$_n$-pyridyl, where n may be =0–3 and in which phenyl, pyridyl in each case may be substituted up to two times by Cl, F, CN, CF$_3$, (C$_1$–C$_3$)-alkyl, or O—(C$_1$–C$_6$)-alkyl;

R5 is (C$_1$–C$_6$)-alkyl, (C$_3$–C$_6$)-cycloalkyl, (CH$_2$)$_n$-phenyl, or (CH$_2$)$_n$-pyridyl, where n may be =0–3 and in which phenyl and pyridyl in each case may be substituted up to two times by Cl, F, CN, CF$_3$, (C$_1$–C$_3$)-alkyl, or O—(C$_1$–C$_6$)-alkyl;

or

R4 and R5 together form a —CH$_2$—CH$_2$—, —CH$_2$—C(CH$_3$)$_2$— or —CH$_2$—CH$_2$—CH$_2$— group;

or

C)
Y is a direct bond or —CH$_2$—;
X is CH$_2$, CH(CH$_3$), CH(C$_2$H$_5$), or CH(C$_3$H$_7$);
R1 and R1' independently of one another are H; F; Cl; Br; I; CN; COOH; COO(C$_1$–C$_6$)-alkyl; CONH$_2$; CON[(C$_1$–C$_6$)-alkyl]$_2$; (C$_1$–C$_6$)-alkyl; (C$_2$–C$_6$)-alkenyl; (C$_2$–C$_6$)-alkynyl; O—(C$_1$–C$_6$)-alkly; O—CH$_2$—CF$_3$; O—CH$_2$—CF$_2$—CF$_3$; or O—(C$_4$–C$_6$)-alkyl, where in the alkyl radicals one or more, or all hydrogen(s) may be replaced by fluorine, or one hydrogen may be replaced by OH, OC(O)CH$_3$, O—CH$_2$—Ph, NH$_2$ or N(COOCH$_2$Ph)$_2$;

S—(C$_1$–C$_6$)-alkyl; S—(CH$_2$)$_n$-phenyl; SO$_2$—(C$_1$–C$_6$)-alkyl; or SO$_2$—(CH$_2$)$_n$-phenyl, where n may be =0–6 and the phenyl radical may be substituted up to two times by F, Cl, Br, OH, CF$_3$, NO$_2$, OCF$_3$, O—(C$_1$–C$_6$)-alkyl, or (C$_1$–C$_6$)-alkyl; SO$_2$—NH$_2$; SO$_2$NH(C$_1$–C$_6$)-alkyl; SO$_2$N[(C$_1$–C$_6$)-alkyl]$_2$; N((C$_1$–C$_6$)-alkyl)$_2$; NH(C$_1$–C$_7$)-acyl; phenyl; or O—(CH$_2$)$_n$-phenyl, where n may be =0–4, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted one to 3 times by F, Cl, I, OH, CF$_3$, CN, OCF$_3$, O—(C$_1$–C$_6$)-alkyl, $(C_1-C_6)$-alkyl, $NH_2$, $NH(C_1-C_6)$-alkyl, $N((C_1-C_6)$-alkyl$)_2$, COOH, COO—$(C_1-C_6)$-alkyl, or $CONH_2$;

1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R2 is $(C_1-C_6)$-alkyl, $(CH_2)_n$-phenyl, $(CH_2)_n$-thienyl, $(CH_2)_n$-pyridyl, C(O)—$(CH_2)_n$-phenyl, C(O)—$(CH_2)_n$-thienyl, or C(O)—$(CH_2)_n$-pyridyl, where n may be =0–3 and in which phenyl, thienyl, pyridyl, and furyl in each case may be substituted up to two times by Cl, F, CN, $CF_3$, $(C_1-C_3)$-alkyl, OH, O—$(C_1-C_6)$-alkyl; or C(O)—$(C_1-C_6)$-alkyl;

R3 is H, $(C_1-C_6)$-alkyl, F, CN, O—$(C_1-C_6)$-alkyl, $(CH_2)_n$-phenyl, or $(CH_2)_n$-pyridyl, where n may be =0–3 and in which phenyl and pyridyl in each case may be substituted up to two times by Cl, F, CN, $CF_3$, $(C_1-C_3)$-alkyl, O—$(C_1-C_6)$-alkyl; $(C_2-C_6)$-alkynyl, $C(O)OCH_3$, $C(O)OCH_2CH_3$, C(O)OH, $C(O)NH_2$, $C(O)N(CH_3)_2$, or $OC(O)CH_3$;

R4 is $(C_1-C_6)$-alkyl, $(C_3-C_6)$-cycloalkyl, $(CH_2)_n$-phenyl, or $(CH_2)_n$-pyridyl, where n may be =0–3 and in which phenyl and pyridyl in each case may be substituted up to two times by Cl, F, CN, $CF_3$, $(C_1-C_3)$-alkyl, or O—$(C_1-C_6)$-alkyl;

R5 is $(C_1-C_6)$-alkyl, $(C_3-C_6)$-cycloalkyl, $(CH_2)_n$-phenyl, or $(CH_2)_n$-pyridyl, where n may be =0–3 and in which phenyl and pyridyl in each case may be substituted up to two times by Cl, F, CN, $CF_3$, $(C_1-C_3)$-alkyl, or O—$(C_1-C_6)$-alkyl;

or

R4 and R5 together form a —$CH_2$—$CH_2$—, —$CH_2$—$C(CH_3)_2$— or —$CH_2$—$CH_2$—$CH_2$— group;

or

D)

Y is a direct bond or —$CH_2$—;

X is CH(phenyl), where the phenyl radical may be substituted by F or Cl, O, S, $SO_2$ or N—R6;

R1 and R1' independently of one another are H; F; Cl; Br; I; CN; COOH; $COO(C_1-C_6)$-alkyl; $CONH_2$; $CON[(C_1-C_6)$-alkyl$]_2$; $(C_1-C_6)$-alkyl; $(C_2-C_6)$-alkenyl; $(C_2-C_6)$-alkynyl; O—$(C_1-C_6)$-alkyl; O—$CH_2$—$CF_3$; O—$CH_2$—$CF_2$—$CF_3$; or O—$(C_4-C_6)$-alkyl, where in the alkyl radicals one or more, or all hydrogen(s) may be replaced by fluorine, or one hydrogen may be replaced by OH, $OC(O)CH_3$, O—$CH_2$—Ph, $NH_2$ or $N(COOCH_2Ph)_2$;

S—$(C_1-C_6)$-alkyl; S—$(CH_2)_n$-phenyl; $SO_2$—$(C_1-C_6)$-alkyl; or $SO_2$—$(CH_2)_n$-phenyl, where n may be =0–6 and the phenyl radical may be substituted up to two times by F, Cl, Br, OH, $CF_3$, $NO_2$, CN, $OCF_3$, O—$(C_1-C_6)$-alkyl, or $(C_1-C_6)$-alkyl;

$SO_2$—$NH_2$; $SO_2NH(C_1-C_6)$-alkyl; $SO_2N[(C_1-C_6)$-alkyl$]_2$; $NH_2$; $N((C_1-C_6)$-alkyl$)_2$; $NH(C_1-C_7)$-acyl; phenyl; or O—$(CH_2)_n$-phenyl, where n may be =0–6, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted one to 3 times by F, Cl, I, OH, $CF_3$, CN, $OCF_3$, O—$(C_1-C_6)$-alkyl, $(C_1-C_6)$-alkyl, $NH_2$, $N((C_1-C_6)$-alkyl$)_2$, COOH, COO—$(C_1-C_6)$-alkyl, or $CONH_2$;

1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R2 is H, $(C_1-C_6)$-alkyl, $(CH_2)_n$-phenyl, $(CH_2)_n$-thienyl, $(CH_2)_n$-pyridyl, C(O)—$(CH_2)_n$-phenyl, C(O)—$(CH_2)_n$-thienyl, or C(O)—$(CH_2)_n$-pyridyl, where n may be =0–3 and in which phenyl, thienyl, pyridyl, and furyl in each case may be substituted up to two times by Cl, F, CN, $CF_3$, $(C_1-C_3)$-alkyl, OH, O—$(C_1-C_6)$-alkyl; or C(O)—$(C_1-C_6)$-alkyl;

R3 is H, $(C_1-C_6)$-alkyl, F, CN, O—$(C_1-C_6)$-alkyl, $(CH_2)_n$-phenyl, or $(CH_2)_n$-pyridyl, where n may be =0–3 and in which phenyl and pyridyl in each case may be substituted up to two times by Cl, F, CN, $CF_3$, $(C_1-C_3)$-alkyl, O—$(C_1-C_6)$-alkyl; $(C_2-C_6)$-alkynyl, $C(O)OCH_3$, $C(O)OCH_2CH_3$, C(O)OH, $C(O)NH_2$, $C(O)NHCH_3$, $C(O)N(CH_3)_2$, or $OC(O)CH_3$;

R4 is $(C_1-C_6)$-alkyl, $(C_3-C_6)$-cycloalkyl, $(CH_2)_n$-phenyl, or $(CH_2)_n$-pyridyl, where n may be =0–3 and in which phenyl and pyridyl in each case may be substituted up to two times by Cl, F, CN, $CF_3$, $(C_1-C_3)$-alkyl, or O—$(C_1-C_6)$-alkyl;

R5 is $(C_1-C_6)$-alkyl, $(C_3-C_6)$-cycloalkyl, $(CH_2)_n$-phenyl, or $(CH_2)_n$-pyridyl, where n may be =0–3 and in which phenyl and pyridyl in each case may be substituted up to two times by Cl, F, CN, $CF_3$, $(C_1-C_3)$-alkyl, or O—$(C_1-C_6)$-alkyl;

or

R4 and R5 together form a —$CH_2$—$CH_2$—, —$CH_2$—$C(CH_3)_2$— or —$CH_2$—$CH_2$—$CH_2$— group;

R6 is $SO_2$—$(C_6H_4$-4-$CH_3)$ or

E)

Y is a direct bond or —$CH_2$—;

X is $CH_2$, $CH(CH_3)$, $CH(C_2H_5)$, or $CH(C_3H_7)$;

R1 is H, F, Cl, $CH_3$, $CF_3$, or O—$(C_1-C_3)$-alkyl;

R1' is H, F, or Cl;

R2 is H;

R3 is H, or $(C_1-C_3)$-alkyl;

R4 is phenyl, where the phenyl radical may be substituted up to two times by F, Cl, $(C_1-C_6)$-alkyl, $(C_3-C_6)$-cycloalkyl, O—$(C_1-C_3)$-alkyl, $CF_3$, O—$CH_2$-phenyl, COOH, $COO(C_1-C_6)$-alkyl, or $CONH_2$;

R5 is phenyl, where the phenyl radical may be substituted up to two times by F, Cl, $(C_1-C_6)$-alkyl, $(C_3-C_6)$-cycloalkyl, O—$(C_1-C_3)$-alkyl, $CF_3$, O—$CH_2$-phenyl, COOH, $COO(C_1-C_6)$-alkyl, or $CONH_2$;

or a physiologically tolerable salt thereof, or a physiologically functional derivative thereof.

4. A compound of the formula I, as claimed in claim 1, wherein

Y is a direct bond;

X is $CH_2$

R1 and R1' independently of one another are H; F; Cl; CN; COOH; $CONH_2$; $COO(C_1-C_3)$-alkyl; $(C_1-C_6)$-alkyl; $(C_2-C_6)$-alkenyl; or $(C_2-C_6)$-alkynyl, where in the alkyl, alkenyl and alkynyl radicals one hydrogen may be replaced by OH, $OC(O)CH_3$, O—$CH_2$—Ph, $NH_2$ or $N(COOCH_2Ph)_2$;

$OCF_3$; $OCH_2CF_3$; O—$(C_1-C_4)$-alkyl; where in the alkyl radicals one or more, or all hydrogen(s) may be replaced by fluorine, or one hydrogen may be replaced by OH, $OC(O)CH_3$, O—$CH_2$—Ph, $NH_2$ or $N(COOCH_2Ph)_2$;

$SO_2$—$(C_1-C_6)$-alkyl, $SO_2$—$(CH_2)_n$-phenyl, where n may be =0–3 and the phenyl radical may be substituted by F, Cl, OH, $CF_3$, or O—$(C_1-C_4)$-alkyl;

NH—(CO)—($C_1$–$C_3$)-alkyl; $(CH_2)_n$-phenyl, S—$(CH_2)_n$-phenyl, or O—$(CH_2)_n$-phenyl, where n may be =0–3, 1- or 2-naphthyl, 2-, 3- or 4-pyridyl, 2- or 3-furanyl or 2- or 3-thienyl, where the phenyl, naphthyl, pyridyl, furanyl or thienyl rings in each case may be substituted by F, Cl, $CF_3$, ($C_1$–$C_6$)-alkyl, O—($C_1$–$C_6$)-alkyl and where in the alkyl radicals one hydrogen may be replaced by OH, $OC(O)CH_3$, O—$CH_2$—Ph, $NH_2$ or $N(COOCH_2Ph)_2$;

1,2,3-triazol-5-yl, where the triazole ring may be substituted in the 1-, 2- or 3-position by methyl or benzyl;

tetrazol-5-yl, where the tetrazole ring may be substituted in the 1- or 2-position by methyl or benzyl;

R2 is H, ($C_1$–$C_4$)-alkyl, ($C_5$–$C_6$)-cycloalkyl; $(CH_2)_n$-phenyl, where n may be =0–3, C(O)—($C_1$–$C_4$)-alkyl or C(O)-phenyl;

R3 is F, ($C_4$–$C_6$)-alkyl, $CH_2$-phenyl, where phenyl may be substituted up to two times by F, Cl, $CF_3$, O—($C_1$–$C_3$)-alkyl, ($C_1$–$C_3$)-alkyl, COOH, CO—O—($C_1$–$C_3$)-alkyl or $CONH_2$;

R4 is ($C_1$–$C_6$)-alkyl, ($C_3$–$C_6$)-cycloalkyl, $(CH_2)_n$-phenyl, where n may be =0–3 and the phenyl radical may be substituted up to two times by F, Cl, O—($C_1$–$C_4$)-alkyl or OH;

R5 is ($C_1$–$C_6$)-alkyl, ($C_3$–$C_6$)-cycloalkyl, $(CH_2)_n$-phenyl, where n may be =0–3 and the phenyl radical may be substituted up to two times by F, Cl, O—($C_1$–$C_4$)-alkyl or OH;

or a physiologically tolerable salt thereof.

5. A pharmaceutical composition comprising one or more of the compounds as claimed in claim 1.

6. A pharmaceutical composition comprising one or more of the compounds as claimed in claim 1 and one or more anorectic active compounds.

7. A method of treating obesity in a mammal, comprising administering to a mammal in need thereof, a compound as claimed in claim 1.

8. A method for the prophylaxis or treatment of type II diabetes in a mammal comprising administering to a mammal in need thereof, a compound as claimed in claim 1.

9. A process for the production of a pharamaceutical composition comprising one or more of the compounds as claimed in claim 1, which comprises mixing the compound with a pharmaceutically suitable excipient and bringing this mixture into a form suitable for administration.

10. A compound of the formula

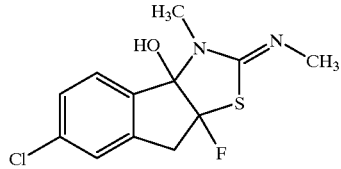

or a physiologically tolerable salt thereof.

11. A compound of the formula

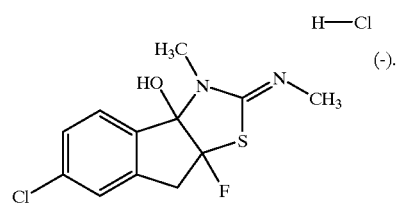

12. A method of treating obesity in a mammal, comprising administering to a mammal in need thereof, a compound as claimed in claim 10.

13. A method for the prophylaxis or treatment of type II diabetes in a mammal comprising administering to a mammal in need thereof, a compound as claimed in claim 10.

14. A method of treating obesity in a mammal, comprising administering to a mammal in need thereof, a compound as claimed in claim 11.

15. A method for the prophylaxis or treatment of type II diabetes in a mammal comprising administering to a mammal in need thereof, a compound as claimed in claim 11.

* * * * *